US009345794B2

(12) United States Patent
Goletz et al.

(10) Patent No.: US 9,345,794 B2
(45) Date of Patent: *May 24, 2016

(54) TUMOR-SPECIFIC RECOGNITION MOLECULES

(71) Applicant: Glycotope GmbH, Berlin (DE)

(72) Inventors: Steffen Goletz, Glienicke-Nordbahn (DE); Antje Danielczyk, Kolberg (DE); Uwe Karsten, Panketal (DE); Peter Ravn, London (GB); Renate Stahn, Berlin (DE); Peter Astrup Christensen, Ålborg (DK)

(73) Assignee: Glycotype GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/102,214

(22) Filed: Dec. 10, 2013

(65) Prior Publication Data

US 2014/0099259 A1 Apr. 10, 2014

Related U.S. Application Data

(63) Continuation of application No. 13/302,698, filed on Nov. 22, 2011, now Pat. No. 8,617,846, which is a continuation of application No. 10/536,834, filed as application No. PCT/DE03/03994 on Dec. 1, 2003, now Pat. No. 8,088,357.

(30) Foreign Application Priority Data

Nov. 29, 2002 (DE) .................................. 102 56 900

(51) Int. Cl.
| | |
|---|---|
| A61K 39/395 | (2006.01) |
| C07K 16/30 | (2006.01) |
| A61K 51/10 | (2006.01) |
| A61K 47/48 | (2006.01) |
| A61K 51/00 | (2006.01) |
| A61K 39/00 | (2006.01) |

(52) U.S. Cl.
CPC ....... *A61K 51/1045* (2013.01); *A61K 47/48569* (2013.01); *A61K 47/48784* (2013.01); *C07K 16/3076* (2013.01); *A61K 2039/505* (2013.01); *C07K 2317/24* (2013.01); *C07K 2317/622* (2013.01); *C07K 2317/626* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,506,343 | A | 4/1996 | Kufe |
| 5,683,674 | A | 11/1997 | Taylor-Papadimitriou et al. |
| 5,739,277 | A | 4/1998 | Presta et al. |
| 5,804,187 | A | 9/1998 | Do Couto et al. |
| 5,902,582 | A | 5/1999 | Hung |
| 6,315,997 | B1 | 11/2001 | Do Couto et al. |
| 2002/0132771 | A1 | 9/2002 | Madiyalakan |
| 2006/0292643 | A1 | 12/2006 | Goletz et al. |

FOREIGN PATENT DOCUMENTS

| | | |
|---|---|---|
| DE | 4329004 A1 | 3/1995 |
| WO | 93/20841 A1 | 10/1993 |
| WO | 01/12217 A1 | 2/2001 |
| WO | 02/44217 | 6/2002 |

OTHER PUBLICATIONS

MSNBC News Services, "Mixed Results on New Cancer Drug", Nov. 9, 2000.
Bagshawe et al., "Antibody-directed enzyme prodrug therapy (ADEPT) for cancer," *Expert Opin. Biol. Ther.* 4(11):1777-1789, Nov. 2004.
Boel et al., "Functional human monoclonal antibodies of all isotypes constructed from phage display library-derived single-chain Fv antibody fragments," *J. Immunol. Methods* 239:153-66, 2000.
Brechbiel et al., "Synthesis of l(p-Isothiocyanatobenzyl) derivatives of DTPA and EDTA. Antibody labeling and tumor-imaging studies," *Inorg. Chem.* 25:2772-2781, 1986.
Burgess et al., "Possible Dissociation of the Heparin-Binding and Mitogenic Activities of the Heparin-Binding (Acidic Fibroblast) Growth Factor-1 from its Receptor Binding Activities by Site Directed Mutagenesis of a Single Lysine Residue," *Journal of Cell Biology* 111:2129-2138, 1990.
Casset et al., "A peptide mimetic of an anti-CD4 monoclonal antibody by rational design," *Biochemical and Biophysical Research Communications* 307I(1):198-205, Jul. 18, 2003.
Chen et al., "Selection and analysis of an optimized anti-VEGF antibody: crystal structure of an affinity-matured Fab in complex with antigen," *Journal of Molecular Biology* 293(4):865-881, Nov. 5, 1999.
Chothia et al., "The predicted structure of immunoglobulin D1.3 and its comparison with the crystal structure," *Science* 233:755-758, 1986.
Chothia et al., "Conformations of immunoglobulin hypervariable regions," *Nature* 342:877-883, 1989.
Chothia et al., "Structural repertoire of the human $V_H$ segments," *J. Mol. Biol.* 227:799-817, 1992.
Chothia et al., "Canonical structures for the hypervariable regions of immunoglobulins," *J. Mol. Biol.* 196:901-917, 1987.
Dai et al., "Effect of Desialylation on Binding, Affinity, and Specificity of 56 Monoclonal Antibodies Against MUC1 Mucin," *Tumor Biology* 19 (Supplemental 19):100-110, 1998.
Dermer, "Another Anniversary of the War on Cancer," *Bio/technology* 12:320, 1994.
Euhus et al., "Appraisal of anti-idiotypic antibodies in the treatment of solid tumors in humans," *Surgery, Gynecology and Obstetrics* 175(1):89-96, Jul. 1992. Abstract Only.
Fiebig et al., "Clonogenic Assay with Established Human Tumor Xenografts: Correlation of In Vitro to In Vivo Activity as a Basis for Anticancer Drug Discovery," *European Journal of Cancer* 40:802-820 2004.
Freshney, "Culture of Animal Cells, A Manual of Basic Technique," Alan R. Liss, Inc., 1983, New York, p. 4.
Goletz et al., "Binding Patterns of 33-TD-4(MUC1) Antibodies Towards Single-Chain Fragments and Peptides Mimicking the Conformation of the MUC1 PDTRP EPITOPE," *Tumor Biology* 21(Supplement 1):142, Sep. 2000.

(Continued)

*Primary Examiner* — Karen Canella
(74) *Attorney, Agent, or Firm* — Seed IP Law Group PLLC

(57) ABSTRACT

The invention relates to recognition molecules which are directed towards tumors and can be used in the diagnosis and therapy of tumor diseases.

22 Claims, 15 Drawing Sheets

(56) References Cited

OTHER PUBLICATIONS

Figure 1B:
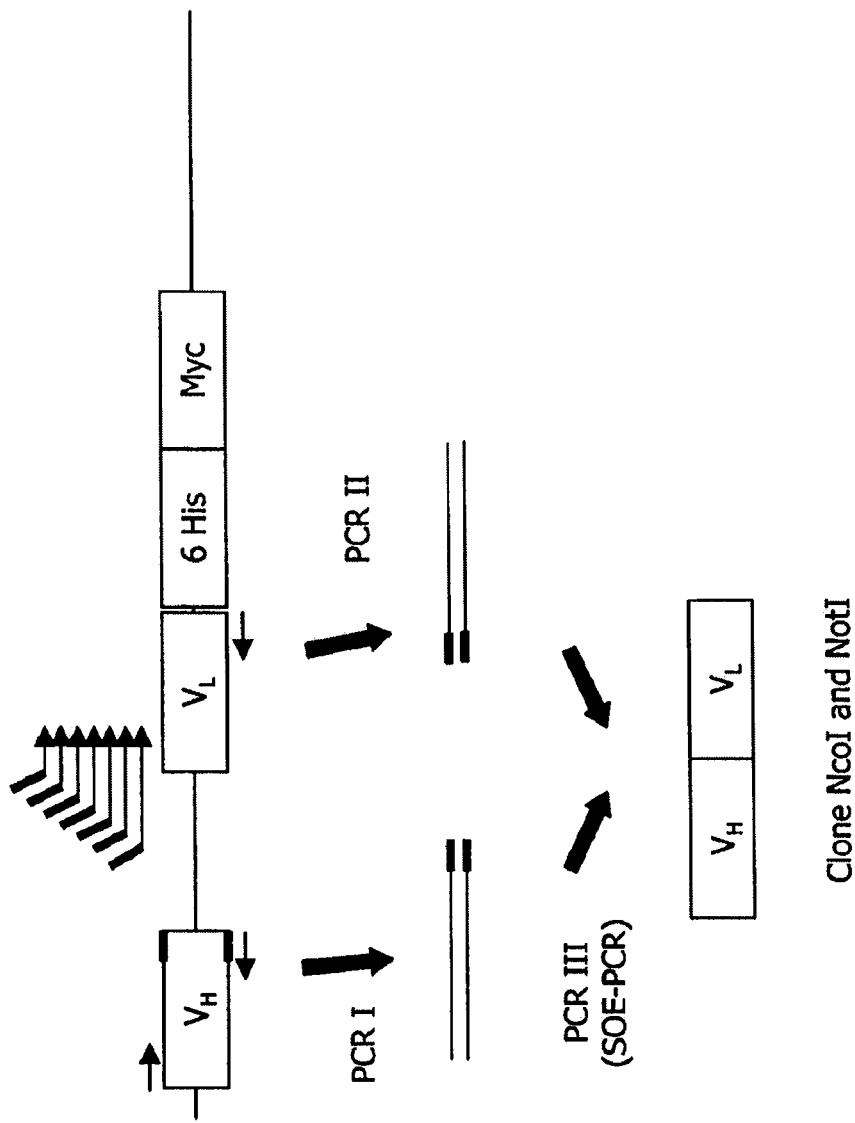

Green et al., "Activation-induced cell death in T cells," *Immunological Reviews* 193:70-81, Jun. 2003.
Gura, "Systems for Identifying New Drugs are Often Faulty," *Science* 278:1041-1042, 1997.
Herrera et al., "Efficiency of erythropoietin's signal peptide for $HIV_{MN}$-1 gp 120 expression," *Biochem. Biophys. Res. Com.* 273:557-559, 2000.
Hinoda et al., "Circulating Tumor-Associated Antigens Detected by Monoclonal Antibodies Against the Polypeptide Core of Mucin: Comparison of Antigen MUSE11 with CA 15-3," *Gastroenterologia Japonica* 27(3):390-395, 1992.
Holm et al., "Functional mapping and single chain construction of the anti-cytokeratin 8 monoclonal antibody TS1," *Molecular Immunology* 44(6):1075-1084, Feb. 2007.
Hosse et al., "A New Generation of Protein Display Scaffolds for Molecular Recognition," *Protein Science* 15:14-27, 2006.
Hsieh et al., "Controlling chemical reactivity with antibodies," *Science* 260(5106):337-339, Apr. 16, 1993.
Hufton et al., "Development and Application of Cytotoxic T Lymphocyte-Associated Antigen 4 as a Protein Scaffold for the Generation of Novel Binding Ligands," *FEBS Letters* 475(3): 225-231, 2002.
Jensen et al., "Functional Improvement of Antibody Fragments Using a Novel Phage Coat Protein III Fusion System," *Biochemical and Biophysical Research Communications* 298:566-573, 2002.
Jeschke et al., "Expression of the Thomsen-Friedenreich antigen and of its putative carrier protein mucin 1 in the human placenta and in trophoblast cells in vitro" *Histochemistry and Cell Biology* 117(3):219-226, Mar. 2002, XP002290192.
Karsten et al., "A New Monoclonal Antibody (A78-G/A7) to the Thomsen—Friedenreich Pan-Tumor Antigen," *Hybridoma* 14(1):37-44, 1995.
Kozak et al., "Nature of the bifunctional chelating agent used for radioimmunotherapy with yttrium-90 monoclonal antibodies: critical factors in determining in vivo survival and organ toxicity," *Cancer Res.* 49: 2639-2644, 1989.
Lazar et al., "Transforming Growth Factor Alpha: Mutation of Aspartic Acid 47 and Leucine 48 Results in Different Biological Activities," *Molecular and Cellular Biology* 8:1247-1252, 1988.
Liao et al., "Design of transgenes for efficient expression of active chimeric proteins on mammalian cells," *Biotechnol. Bioeng.* 73:313-323, 2000.
Libyh et al., "A recombinant human scFv anti-Rh(D) antibody with multiple valences using a C-terminal fragment of C4-binding protein," *Blood* 90(10): 978-83, 1997.
Linardou et al., "Deoxyribonuclease I (DNAseI). A novel approach for targeted cancer therapy," *Cell Biophys.* 24-25:243-248, 1994. Abstract only.
MacCallum et al., "Antibody-antigen interactions: contact analysis and binding site topography," *Journal of Molecular Biology* 262(5):732-745, Oct. 11, 1996.
Martin et al., "Structural families in loops of homologous proteins: automatic classification, modelling and application to antibodies," *J. Mol. Biol.* 263:800-815, 1996.
Matzinger, "Tolerance, danger, and the extended family," *Annual Review in Immunology* 12:991-1045, 1994.
Morrison et al., "Complement activation and Fc receptor binding by IgG," in *Protein Engineering of antibody Molecules for Prophylactic and therapeutic applications in Man*, 1993, Mike Clark (ed.), pp. 101-113.
Nicaise et al., "Affinity Transfer by CDR Grafting on a Nonimmunoglobulin Scaffold," *Protein Science* 13:1882-1891, 2004.

Nuttall et al., "Design and expression of soluble CTLA-4 variable domain as a scaffold for the display of functional polypeptides," *Proteins* 36:217-227, 1999.
Nygren et al., "Scaffolds for engineering novel binding sites in proteins," *Curr. Opin. Struc. Biol.* 7:463-469, 1997.
Panka et al., "Variable region framework differences result in decreased or increased affinity of variant anti-digoxin antibodies," *Proc. Natl. Acad. Sci. USA* 85(9):3080-3084, May 1988.
Pascalis et al., "Grafting of "abbreviated" complementarity-determining regions containing specificity-determining residues essential for ligand contact to engineer a less immunogenic humanized monoclonal antibody," *Journal of Immunology* 169(6):3076-3084, Sep. 15, 2002.
Peach et al., "Complementarity Determining Region 1 (CDRR 1)- and CDR3-analogous Regions in CTLA-4 and CD28 Determine the Binding to B7-1," *Journal of Experimental Medicine* 180(6):2049-2058, Dec. 1, 1994.
Price et al., "Summary report on the ISOBM TD-4 Workshop: analysis of 56 monoclonal antibodies against the MUC1 mucin," *Tumor Biology* 19(Suppl 1):1-20, 1998, XP002071245.
Rittenhouse-Diakun et al., "Development and characterization of monoclonal antibody to T-antigen: (gal beta1-3GalNAc-alpha-O)," *Hybridoma* 17(2):165-173, 1998.
Rooman et al., "Amino acid sequence templates derived from recurrent turn motifs in proteins: critical evaluation of their predictive power," *Protein Eng.* 13:23-27, 1989.
Rudikoff et al., "Single amino acid substitution altering antigen-binding specificity," *Proc. Natl. Acad. Sci. USA* 79(6):1979-1983, Mar. 1982.
Saerens et al., "Identification of a Universal VHH Framework to Graft Non-Canonical Antigen-Binding Loops of Camel Single-Domain Antibodies," *Journal of Molecular Biology* 352(3):597-607, Sep. 2005.
Scheibel et al., "Contribution of N- and C-Terminal Domains to the Function of Hsp90 in *Saccharomyces cerevisiae*," *Molecular Microbiology* 34:701-713, 1999.
Schlom, "Monoclonal Antibodies: They're More and Less Than You Think," in *Molecular Foundations of Oncology*, 1991, Samuel Broder (ed.), pp. 95-134.
Schneider et al., "Overexpression of sialyltransferase CMP-sialic acid: Galbeta1,3GalNAc-R alpha6-Sialyltransferase is related to poor patient survival in human colorectal carcinomas" *Cancer Research* 61(11):4605-4611, Jun. 1, 2001, XP002232470.
Schneider et al., "Thermostability of membrane protein helix-helix interaction elucidated by statistical analysis," *FEBS Lett.* 532(1-2):231-236, Dec. 4, 2002.
Skerra, "Engineered protein scaffolds for molecular recognition." *J. Mol. Recog.* 13:167-187, 2000.
Skerra et al., "Alternative Non-Antibody Scaffolds for Molecular Recognition," *Current Opinion in Biotechnology* 18:295-303, 2007.
Stimmel et al., "Yttrium-90 chelation properties of tetraazatetraacetic acid macrocycles, diethylenetriaminepentaacetic acid analogues, and a novel terpyridine acyclic chelator," *Bioconjug. Chem.* 6:219-225, 1995.
Vajdos et al., "Comprehensive functional maps of the antigen-binding site of an anti-ErbB2 antibody obtained with shotgun scanning mutagenesis," *Journal of Molecular Biology* 320(2):415-428, Jul. 5, 2002.
Wu et al., "Conformation of complementarity determining region L1 loop in murine IgG λ light chain extends the repertoire of canonical forms," *J. Mol. Biol.* 29:597-601, 1993.
Wu et al., "Humanization of a Murine Monoclonal Antibody by Simultaneous Optimization of Framework and CDR Residues," *Journal of Molecular Biology* 294:151-162, 1999.

Fig. 1a

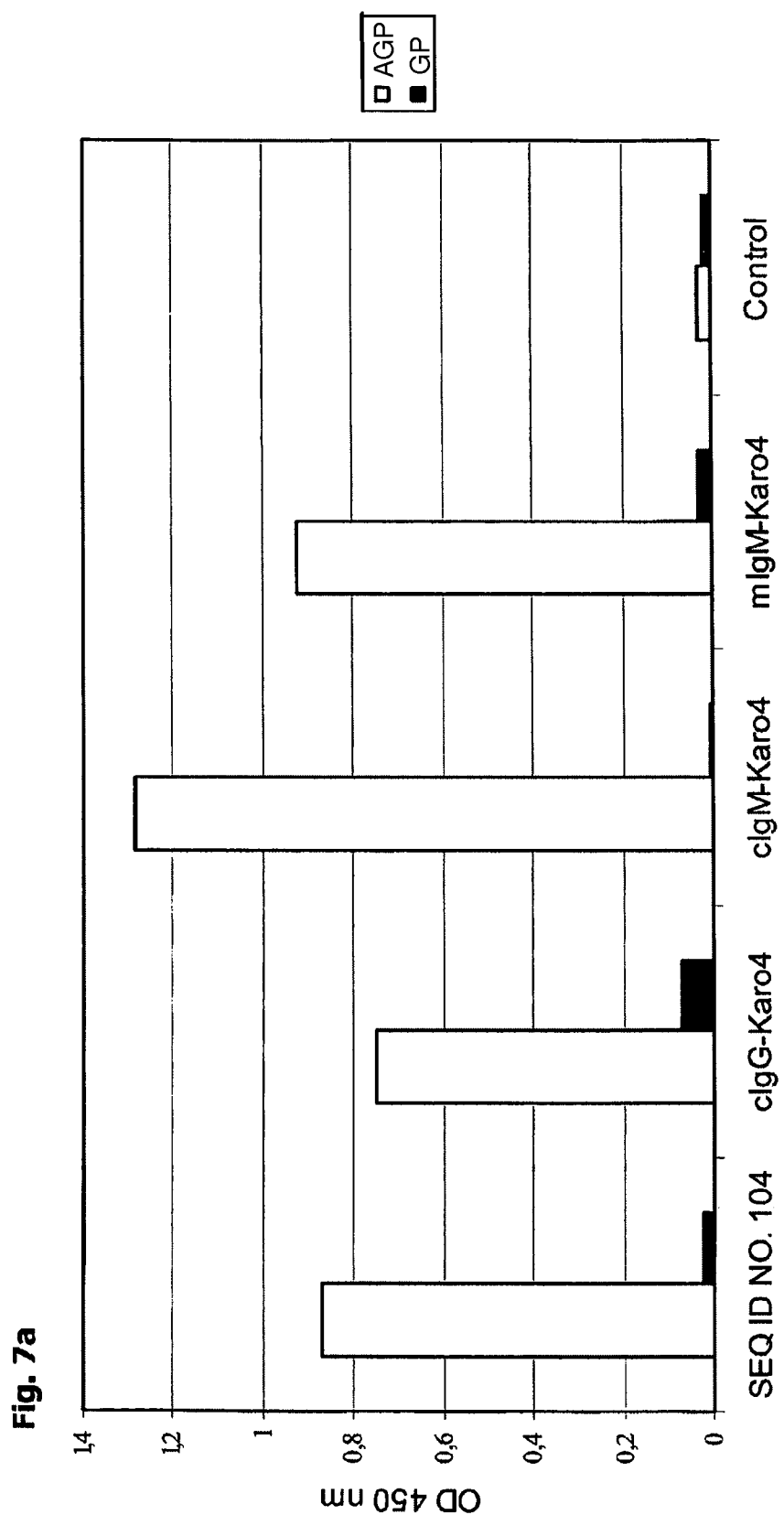

SEQUENCE LISTING

```
<160> NUMBER OF SEQ ID NOS: 152

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Tyr Trp Leu Gly
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Ile Tyr Pro Gly Gly Gly Tyr Thr Asn Tyr Asn Glu Lys Phe Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Ile Tyr Pro Gly Gly Ser Tyr Thr Asn Tyr Asn Glu Lys Phe Lys
1               5                   10                  15

Gly

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Tyr Asp Ala Ala Gly Pro Trp Phe Ala Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Asp Ala Ala Gly Pro Gly Phe Ala Tyr
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Asp Asn His Tyr Phe Asp Tyr
1               5

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Ser Gln Ser Ile Val His Ser Asn Gly Asn Thr Tyr Leu Glu
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Ser Gln Ser Leu Leu His Ser Asn Gly Asn Thr Tyr Leu His
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Ser Ser Gln Ser Leu Leu His Ser Asp Gly Lys Thr Tyr Leu Tyr
1               5                   10                  15

<210> SEQ ID NO 10
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 10

Lys Val Ser Asn Arg Phe Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Val Ser Ser Arg Phe Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Gln Gly Ser His Val Pro Tyr Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gln Ser Thr His Val Pro Tyr Thr
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Tyr Trp Ile Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Tyr Trp Met Gly
1               5
```

```
<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Tyr Trp Trp Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Tyr Trp Val Gly
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Ile Tyr Pro Gly Gly Asp Tyr Thr Asn Tyr Asn Glu Lys Phe Lys
1               5                   10                  15

Gly

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Ile Tyr Pro Gly Gly Asn Tyr Thr Asn Tyr Asn Glu Lys Phe Lys
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Ile Tyr Thr Gly Gly Gly Tyr Thr Asn Tyr Asn Glu Lys Phe Lys
1               5                   10                  15

Gly

<210> SEQ ID NO 21
<211> LENGTH: 17
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 21

Asp Ile Tyr Thr Gly Gly Asp Tyr Thr Asn Tyr Asn Glu Lys Phe Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Ile Tyr Thr Gly Gly Asn Tyr Thr Asn Tyr Asn Glu Lys Phe Lys
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Ile Tyr Thr Gly Gly Ser Tyr Thr Asn Tyr Asn Glu Lys Phe Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Ile Tyr Ala Gly Gly Gly Tyr Thr Asn Tyr Asn Glu Lys Phe Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Ile Tyr Ala Gly Gly Asp Tyr Thr Asn Tyr Asn Glu Lys Phe Lys
1               5                   10                  15

Gly

<210> SEQ ID NO 26
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Ile Tyr Ala Gly Gly Asp Tyr Thr Asn Tyr Asn Glu Lys Phe Lys
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ile Tyr Ala Gly Gly Ser Tyr Thr Asn Tyr Asn Glu Lys Phe Lys
1               5                   10                  15

Gly

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Pro Ser Gln Ser Ile Val His Ser Asn Gly Asn Thr Tyr Leu Glu
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Ser Gln Ser Leu Val His Ser Asn Gly Asn Thr Tyr Leu Glu
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ser Ser Gln Ser Ile Val His Ser Asn Gly Asn Thr Tyr Phe Glu
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 31

Arg Pro Ser Gln Ser Leu Val His Ser Asn Gly Asn Thr Tyr Leu Glu
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Pro Ser Gln Ser Ile Val His Ser Asn Gly Asn Thr Tyr Phe Glu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Ser Gln Ser Leu Val His Ser Asn Gly Asn Thr Tyr Phe Glu
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Pro Ser Gln Ser Leu Leu His Ser Asn Gly Asn Thr Tyr Leu His
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ser Ser Gln Ser Ile Leu His Ser Asn Gly Asn Thr Tyr Leu His
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Ser Gln Ser Leu Leu His Ser Asn Gly Asn Thr Tyr Phe His
1               5                   10                  15

<210> SEQ ID NO 37
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Pro Ser Gln Ser Ile Leu His Ser Asn Gly Asn Thr Tyr Leu His
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Pro Ser Gln Ser Leu Leu His Ser Asn Gly Asn Thr Tyr Phe His
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Ser Gln Ser Ile Leu His Ser Asn Gly Asn Thr Tyr Phe His
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Pro Ser Gln Ser Leu Leu His Ser Asp Gly Lys Thr Tyr Leu Tyr
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Ser Ser Gln Ser Ile Leu His Ser Asp Gly Lys Thr Tyr Leu Tyr
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Ser Ser Gln Ser Leu Leu His Ser Asp Gly Lys Thr Tyr Phe Tyr
```

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Lys Pro Ser Gln Ser Ile Leu His Ser Asp Gly Lys Thr Tyr Leu Tyr
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Lys Pro Ser Gln Ser Leu Leu His Ser Asp Gly Lys Thr Tyr Phe Tyr
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Lys Ser Ser Gln Ser Ile Leu His Ser Asp Gly Lys Thr Tyr Phe Tyr
1               5                   10                  15

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

Thr Thr Val Thr Val Ser Ser
        115

<210> SEQ ID NO 47
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Lys Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Ser Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Asp Asn His Tyr Phe Asp Tyr Trp Gly Gln Gly Thr Thr
            100                 105                 110

Leu Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Lys Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Thr Leu Thr Val Ser Ser
        115

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 49

Glu Val Lys Leu Val Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Ser Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Thr Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Lys Leu Val Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
```

```
                35                  40                  45
Gly Asp Ile Tyr Pro Gly Gly Tyr Thr Asn Tyr Asn Glu Lys Phe
        50                  55                  60
Lys Gly Lys Ala Thr Leu Thr Ala Asp Thr Ser Ser Thr Ala Tyr
65                  70                  75                  80
Met Gln Leu Ser Ser Leu Thr Ser Glu Asp Ser Ala Val Tyr Phe Cys
                85                  90                  95
Ala Tyr Tyr Asp Ala Ala Gly Pro Trp Phe Ala Tyr Trp Gly Gln Gly
            100                 105                 110
Thr Thr Val Thr Val Ser Ser
            115

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Lys Gln Ser Gly Ala Glu Leu Val Arg Pro Gly Thr
1               5                   10                  15
Ser Val Lys Ile Ser Cys Lys Ala Ser Gly Tyr Thr Phe Thr Asn Tyr
                20                  25                  30
Trp Leu Gly Trp Val Lys Gln Arg Pro Gly His Gly Leu Glu Trp Ile
            35                  40                  45
Gly Asp Ile Tyr Pro Gly Gly Tyr Thr Asn Tyr Asn Glu Lys Phe
        50                  55                  60
Lys Gly Lys Ala Thr Leu Thr Ala Asp Thr Ser Ser Thr Ala Tyr
65                  70                  75                  80
Met Gln Leu Ser Ser Leu Thr Ser Glu Asp Ser Ala Val Tyr Phe Cys
                85                  90                  95
Ala Tyr Tyr Asp Ala Ala Gly Pro Trp Phe Ala Tyr Trp Gly Gln Gly
            100                 105                 110
Thr Leu Val Thr Val Ser Ala
            115

<210> SEQ ID NO 53
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Lys Gln Ser Gly Ala Glu Leu Val Arg Pro Gly Thr
1               5                   10                  15
Ser Val Lys Ile Ser Cys Lys Ala Ser Gly Tyr Thr Phe Thr Asn Tyr
                20                  25                  30
Trp Leu Gly Trp Val Lys Gln Arg Pro Gly His Gly Leu Glu Trp Ile
            35                  40                  45
Gly Asp Ile Tyr Pro Gly Gly Tyr Thr Asn Tyr Asn Glu Lys Phe
        50                  55                  60
Lys Gly Lys Ala Thr Leu Thr Ala Asp Thr Ser Ser Thr Ala Tyr
65                  70                  75                  80
Met Gln Leu Ser Ser Leu Thr Ser Glu Asp Ser Ala Val Tyr Phe Cys
```

85                  90                  95

Ala Tyr Tyr Asp Ala Ala Gly Pro Trp Phe Ala Tyr Trp Gly Gln Gly
                100                 105                 110

Thr Thr Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Thr Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
                100                 105                 110

Thr Ser Val Thr Val Ser Ser
        115

<210> SEQ ID NO 55
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Lys Gln Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
                100                 105                 110

Thr Ser Val Thr Val Ser Ser
        115

```
<210> SEQ ID NO 56
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 57
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 58
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Arg Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 59
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Glu Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 60
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Lys Gln Arg Pro Gly Gln Gly Leu Glu Arg Ile
        35                  40                  45

Gly Asp Ile Tyr Pro Gly Gly Tyr Thr Asn Tyr Asn Glu Lys Phe
            50                  55                  60

Lys Gly Lys Ala Thr Leu Thr Ala Asp Thr Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 61
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Leu Gly Trp Val Lys Gln Arg Pro Gly Gln Gly Leu Glu Trp Ile
            35                  40                  45

Gly Asp Ile Tyr Pro Gly Gly Tyr Thr Asn Tyr Asn Glu Lys Phe
            50                  55                  60

Lys Gly Lys Ala Thr Leu Thr Ala Asp Thr Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 62
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Gly Leu Glu Trp Ile
            35                  40                  45

Gly Asp Ile Tyr Pro Gly Gly Tyr Thr Asn Tyr Asn Glu Lys Phe
            50                  55                  60

Lys Gly Lys Ala Thr Leu Thr Ala Asp Thr Ser Thr Ser Thr Ala Tyr
 65                  70                  75                  80

Met Glu Leu Ser Ser Leu Thr Ser Glu Asp Ser Ala Val Tyr Phe Cys
                 85                  90                  95

```
Ala Tyr Tyr Asp Ala Ala Gly Pro Trp Phe Ala Tyr Trp Gly Gln Gly
            100                 105                 110

Thr Thr Val Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Thr Ser Thr Ala Tyr
65                  70                  75                  80

Met Glu Leu Ser Ser Leu Arg Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 64
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Thr Ser Thr Ala Tyr
65                  70                  75                  80

Met Glu Leu Ser Ser Leu Thr Ser Glu Asp Ser Ala Val Tyr Tyr Cys
                85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 65
```

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Val Lys Gln Arg Pro Gly Gln Gly Leu Glu Trp Ile
            35                  40                  45

Gly Asp Ile Tyr Pro Gly Gly Tyr Thr Asn Tyr Asn Glu Lys Phe
        50                  55                  60

Lys Gly Lys Ala Thr Leu Thr Ala Asp Thr Ser Ser Thr Ala Tyr
65                  70                  75                  80

Met Glu Leu Ser Ser Leu Arg Ser Glu Asp Thr Ala Val Tyr Phe Cys
                85                  90                  95

Ala Tyr Tyr Asp Ala Ala Gly Pro Trp Phe Ala Tyr Trp Gly Gln Gly
                100                 105                 110

Thr Leu Val Thr Val Ser Ser
            115

<210> SEQ ID NO 66
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Val Lys Gln Arg Pro Gly Gln Gly Leu Glu Trp Ile
            35                  40                  45

Gly Asp Ile Tyr Pro Gly Gly Tyr Thr Asn Tyr Asn Glu Lys Phe
        50                  55                  60

Lys Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Ala Ala Gly Pro Trp Phe Ala Tyr Trp Gly Gln Gly
                100                 105                 110

Thr Thr Val Thr Val Ser Ser
            115

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67
```

Gln Val Gln Leu Val Gln Ser Gly Ala Glu Val Lys Lys Pro Gly Ala
1               5                   10                  15

Ser Val Lys Val Pro Cys Lys Ala Ser Gly Tyr Thr Phe Thr Asn Tyr
                20                  25                  30

Trp Leu Gly Trp Val Lys Gln Arg Pro Gly Gln Gly Leu Glu Trp Ile
            35                  40                  45

Gly Asp Ile Tyr Pro Gly Gly Tyr Thr Asn Tyr Asn Glu Lys Phe
        50                  55                  60

Lys Gly Lys Ala Thr Leu Thr Ala Asp Thr Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 68
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Val Lys Gln Arg Pro Gly Gln Gly Leu Glu Trp Ile
            35                  40                  45

Gly Asp Ile Tyr Pro Gly Gly Tyr Thr Asn Tyr Asn Glu Lys Phe
        50                  55                  60

Lys Gly Lys Ala Thr Leu Thr Ala Asp Thr Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Ala Ala Gly Pro Trp Phe Ala Tyr Trp Gly Gln Gly
            100                 105                 110

Thr Leu Val Thr Val Ser Ser
        115

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Gly Leu Glu Trp Ile
            35                  40                  45

```
Gly Asp Ile Tyr Pro Gly Gly Gly Tyr Thr Asn Tyr Asn Glu Lys Phe
     50                  55                  60

Lys Gly Lys Ala Thr Leu Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Tyr Tyr Asp Ala Ala Gly Pro Trp Phe Ala Tyr Trp Gly Gln Gly
             100                 105                 110

Thr Leu Val Thr Val Ser Ser
        115
```

<210> SEQ ID NO 70
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Trp Leu Gly Trp Val Arg Gln Ala Pro Gly Gln Gly Leu Glu Trp Ile
         35                  40                  45

Gly Asp Ile Tyr Pro Gly Gly Gly Tyr Thr Asn Tyr Asn Glu Lys Phe
     50                  55                  60

Lys Gly Lys Ala Thr Leu Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Tyr Tyr Asp Ala Ala Gly Pro Trp Phe Ala Tyr Trp Gly Gln Gly
             100                 105                 110

Thr Thr Val Thr Val Ser Ser
        115
```

<210> SEQ ID NO 71
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Trp Leu Gly Trp Val Lys Gln Arg Pro Gly Gln Gly Leu Glu Trp Ile
         35                  40                  45

Gly Asp Ile Tyr Pro Gly Gly Gly Tyr Thr Asn Tyr Asn Glu Lys Phe
     50                  55                  60

Lys Gly Lys Ala Thr Leu Thr Ala Asp Thr Ser Thr Ser Thr Ala Tyr
 65                  70                  75                  80

Met Glu Leu Ser Ser Leu Thr Ser Glu Asp Ser Ala Val Tyr Tyr Cys
                 85                  90                  95
```

Ala Tyr Tyr Asp Ala Ala Gly Pro Trp Phe Ala Tyr Trp Gly Gln Gly
            100                 105                 110

Thr Thr Val Thr Val Ser Ser
        115

<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Lys Gln Arg Pro Gly Gln Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Glu Leu Ser Ser Leu Arg Ser Glu Asp Thr Ala Val Tyr Phe Cys
            85                  90                  95

Ala Tyr Tyr Asp Ala Ala Gly Pro Trp Phe Ala Tyr Trp Gly Gln Gly
            100                 105                 110

Thr Thr Val Thr Val Ser Ser
        115

<210> SEQ ID NO 73
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Tyr Tyr Asp Ala Ala Gly Pro Trp Phe Ala Tyr Trp Gly Gln Gly
            100                 105                 110

Thr Thr Val Thr Val Ser Ser
        115

<210> SEQ ID NO 74
<211> LENGTH: 119

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Thr Ser Thr Ala Tyr
65                  70                  75                  80

Met Glu Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
                100                 105                 110

Thr Thr Val Thr Val Ser Ser
            115

<210> SEQ ID NO 75
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Lys Gln Arg Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Tyr Tyr Asp Ala Ala Gly Pro Trp Phe Ala Tyr Trp Gly Gln Gly
                100                 105                 110

Thr Leu Val Thr Val Ser Ser
            115

<210> SEQ ID NO 76
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Val Gln Ser Gly Ala Glu Val Lys Lys Pro Gly Ala
```

```
                1               5                  10                  15
Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Ala Ala Gly Pro Trp Phe Ala Tyr Trp Gly Gln Gly
                100                 105                 110

Thr Leu Val Thr Val Ser Ser
            115

<210> SEQ ID NO 77
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Val Lys Gln Arg Pro Gly Gln Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Ala Ala Gly Pro Trp Phe Ala Tyr Trp Gly Gln Gly
                100                 105                 110

Thr Leu Val Thr Val Ser Ser
            115

<210> SEQ ID NO 78
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Gly Leu Glu Trp Met
            35                  40                  45

Gly Asp Ile Tyr Pro Gly Gly Gly Tyr Thr Asn Tyr Asn Glu Lys Phe
```

```
                    50                  55                  60
Lys Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Tyr Tyr Asp Ala Ala Gly Pro Trp Phe Ala Tyr Trp Gly Gln Gly
                100                 105                 110

Thr Leu Val Thr Val Ser Ser
            115

<210> SEQ ID NO 79
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Gly Leu Glu Trp Met
            35                  40                  45

Gly Asp Ile Tyr Pro Gly Gly Gly Tyr Thr Asn Tyr Asn Glu Lys Phe
     50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                    85                  90                  95

Ala Tyr Tyr Asp Ala Ala Gly Pro Trp Phe Ala Tyr Trp Gly Gln Gly
                100                 105                 110

Thr Leu Val Thr Val Ser Ser
            115

<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Gln Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                    85                  90                  95

Ser His Val Pro Tyr Thr Phe Gly Gly Gly Thr Lys Leu Glu Ile Lys
```

<210> SEQ ID NO 81
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 81

Asp Ile Val Ile Thr Gln Thr Pro Leu Ser Leu Pro Val Ser Leu Gly
1               5                   10                  15
Asp Gln Ala Ser Ile Ser Cys Arg Ser Ser Gln Ser Leu Leu His Ser
            20                  25                  30
Asn Gly Asn Thr Tyr Leu His Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Tyr Thr Phe Gly Gly Gly Thr Lys Leu Glu Ile Lys
            100                 105                 110
Arg Ala

<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

Asp Ile Gln Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Tyr Thr Phe Gly Gly Gly Thr Lys Leu Glu Leu Lys
            100                 105                 110
Arg Ala

<210> SEQ ID NO 83
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala

<210> SEQ ID NO 84
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Leu Lys
            100                 105                 110

Arg Ala

<210> SEQ ID NO 85
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser

```
                35                  40                  45
Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Tyr Thr Phe Gly Gly Gly Thr Lys Val Glu Ile Lys
                100                 105                 110

Arg Ala

<210> SEQ ID NO 86
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
                35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Tyr Thr Phe Gly Gln Gly Thr Lys Val Glu Ile Lys
                100                 105                 110

Arg Ala

<210> SEQ ID NO 87
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
                35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95
```

```
Ser His Val Pro Tyr Thr Phe Gly Gly Gly Thr Lys Val Glu Ile Lys
            100                 105                 110
Arg Ala

<210> SEQ ID NO 88
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Val Glu Ile Lys
            100                 105                 110
Arg Ala

<210> SEQ ID NO 89
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110
Arg Ala

<210> SEQ ID NO 90
<211> LENGTH: 114
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 90

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Val Glu Ile Lys
            100                 105                 110

Arg Ala

<210> SEQ ID NO 91
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Ala

<210> SEQ ID NO 92
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

-continued

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                 85                  90                  95

Ser His Val Pro Tyr Thr Phe Gly Gln Gly Thr Lys Val Glu Ile Lys
                100                 105                 110

Arg Ala

<210> SEQ ID NO 93
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Val Met Thr Gln Thr Pro Leu Ser Leu Pro Val Thr Pro Gly
1               5                   10                  15

Gln Pro Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                 85                  90                  95

Ser His Val Pro Tyr Thr Phe Gly Gln Gly Thr Lys Val Glu Ile Lys
                100                 105                 110

Arg Ala

<210> SEQ ID NO 94
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                 85                  90                  95

```
Ser His Val Pro Tyr Thr Phe Gly Gln Gly Thr Lys Val Glu Ile Lys
            100                 105                 110

Arg Ala

<210> SEQ ID NO 95
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
            85                  90                  95

Ala Tyr Tyr Asp Ala Ala Gly Pro Gly Phe Ala Tyr Trp Gly Gln Gly
            100                 105                 110

Thr Thr Val Thr Val Ser Ser Ala Ser Ser Gly Gly Gly Gly Ser Gly
            115                 120                 125

Gly Gly Gly Ser Gly Gly Ser Ala Arg Asp Ile Gln Met Thr Gln Thr
        130                 135                 140

Pro Leu Ser Leu Pro Val Ser Leu Gly Asp Gln Ala Ser Ile Ser Cys
145                 150                 155                 160

Arg Ser Ser Gln Ser Ile Val His Ser Asn Gly Asn Thr Tyr Leu Glu
                165                 170                 175

Trp Tyr Leu Gln Lys Pro Gly Gln Ser Pro Lys Leu Leu Ile Tyr Lys
            180                 185                 190

Val Ser Asn Arg Phe Ser Gly Val Pro Asp Arg Phe Ser Gly Ser Gly
        195                 200                 205

Ser Gly Thr Asp Phe Thr Leu Lys Ile Ser Arg Val Glu Ala Glu Asp
    210                 215                 220

Leu Gly Val Tyr Tyr Cys Phe Gln Gly Ser His Val Pro Tyr Thr Phe
225                 230                 235                 240

Gly Gly Gly Thr Lys Leu Glu Ile Lys Arg Ala Ala His His
                245                 250                 255

His His His Gly Ala Ala Glu Gln Lys Leu Ile Ser Glu Glu Asp Leu
            260                 265                 270

Asn Gly Ala Ala
        275

<210> SEQ ID NO 96
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 96

```
Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

Thr Thr Val Thr Val Ser Ser Ala Ser Ser Gly Ser Gly Ser Ser Ala
        115                 120                 125

Asp Ile Gln Met Thr Gln Thr Pro Leu Ser Leu Pro Val Ser Leu Gly
    130                 135                 140

Asp Gln Ala Ser Ile Ser Cys Arg Ser Ser Gln Ser Ile Val His Ser
145                 150                 155                 160

Asn Gly Asn Thr Tyr Leu Glu Trp Tyr Leu Gln Lys Pro Gly Gln Ser
                165                 170                 175

Pro Lys Leu Leu Ile Tyr Lys Val Ser Asn Arg Phe Ser Gly Val Pro
            180                 185                 190

Asp Arg Phe Ser Gly Ser Gly Ser Gly Thr Asp Phe Thr Leu Lys Ile
        195                 200                 205

Ser Arg Val Glu Ala Glu Asp Leu Gly Val Tyr Tyr Cys Phe Gln Gly
    210                 215                 220

Ser His Val Pro Tyr Thr Phe Gly Gly Gly Thr Lys Leu Glu Ile Lys
225                 230                 235                 240

Arg Ala Ala Ala His His His His His His Gly Ala Ala Glu Gln Lys
                245                 250                 255

Leu Ile Ser Glu Glu Asp Leu Asn Gly Ala Ala
            260                 265
```

<210> SEQ ID NO 97
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80
```

```
Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

Thr Thr Val Thr Val Ser Ser Ala Ser Ser Gly Gly Ser Ser Ala Asp
            115                 120                 125

Ile Gln Met Thr Gln Thr Pro Leu Ser Leu Pro Val Ser Leu Gly Asp
        130                 135                 140

Gln Ala Ser Ile Ser Cys Arg Ser Ser Gln Ser Ile Val His Ser Asn
145                 150                 155                 160

Gly Asn Thr Tyr Leu Glu Trp Tyr Leu Gln Lys Pro Gly Gln Ser Pro
                165                 170                 175

Lys Leu Leu Ile Tyr Lys Val Ser Asn Arg Phe Ser Gly Val Pro Asp
            180                 185                 190

Arg Phe Ser Gly Ser Gly Ser Gly Thr Asp Phe Thr Leu Lys Ile Ser
            195                 200                 205

Arg Val Glu Ala Glu Asp Leu Gly Val Tyr Tyr Cys Phe Gln Gly Ser
        210                 215                 220

His Val Pro Tyr Thr Phe Gly Gly Gly Thr Lys Leu Glu Ile Lys Arg
225                 230                 235                 240

Ala Ala Ala His His His His His Gly Ala Ala Glu Gln Lys Leu
                245                 250                 255

Ile Ser Glu Glu Asp Leu Asn Gly Ala Ala
                260                 265

<210> SEQ ID NO 98
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

Thr Thr Val Thr Val Ser Ser Ala Ser Ser Gly Ser Ser Ala Asp Ile
            115                 120                 125

Gln Met Thr Gln Thr Pro Leu Ser Leu Pro Val Ser Leu Gly Asp Gln
        130                 135                 140

Ala Ser Ile Ser Cys Arg Ser Ser Gln Ser Ile Val His Ser Asn Gly
145                 150                 155                 160

Asn Thr Tyr Leu Glu Trp Tyr Leu Gln Lys Pro Gly Gln Ser Pro Lys
```

```
                    165                 170                 175
Leu Leu Ile Tyr Lys Val Ser Asn Arg Phe Ser Gly Val Pro Asp Arg
            180                 185                 190

Phe Ser Gly Ser Gly Ser Gly Thr Asp Phe Thr Leu Lys Ile Ser Arg
            195                 200                 205

Val Glu Ala Glu Asp Leu Gly Val Tyr Tyr Cys Phe Gln Gly Ser His
            210                 215                 220

Val Pro Tyr Thr Phe Gly Gly Gly Thr Lys Leu Glu Ile Lys Arg Ala
225                 230                 235                 240

Ala Ala His His His His His Gly Ala Ala Glu Gln Lys Leu Ile
                245                 250                 255

Ser Glu Glu Asp Leu Asn Gly Ala Ala
            260                 265

<210> SEQ ID NO 99
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

Thr Thr Val Thr Val Ser Ser Ala Ser Ser Ser Ala Asp Ile Gln
        115                 120                 125

Met Thr Gln Thr Pro Leu Ser Leu Pro Val Ser Leu Gly Asp Gln Ala
130                 135                 140

Ser Ile Ser Cys Arg Ser Ser Gln Ser Ile Val His Ser Asn Gly Asn
145                 150                 155                 160

Thr Tyr Leu Glu Trp Tyr Leu Gln Lys Pro Gly Gln Ser Pro Lys Leu
                165                 170                 175

Leu Ile Tyr Lys Val Ser Asn Arg Phe Ser Gly Val Pro Asp Arg Phe
            180                 185                 190

Ser Gly Ser Gly Ser Gly Thr Asp Phe Thr Leu Lys Ile Ser Arg Val
        195                 200                 205

Glu Ala Glu Asp Leu Gly Val Tyr Tyr Cys Phe Gln Gly Ser His Val
    210                 215                 220

Pro Tyr Thr Phe Gly Gly Gly Thr Lys Leu Glu Ile Lys Arg Ala Ala
225                 230                 235                 240

Ala His His His His His Gly Ala Ala Glu Gln Lys Leu Ile Ser
                245                 250                 255
```

```
Glu Glu Asp Leu Asn Gly Ala Ala
            260
```

<210> SEQ ID NO 100
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

Thr Thr Val Thr Val Ser Ser Ala Ser Ser Ala Asp Ile Gln Met
        115                 120                 125

Thr Gln Thr Pro Leu Ser Leu Pro Val Ser Leu Gly Asp Gln Ala Ser
    130                 135                 140

Ile Ser Cys Arg Ser Ser Gln Ser Ile Val His Ser Asn Gly Asn Thr
145                 150                 155                 160

Tyr Leu Glu Trp Tyr Leu Gln Lys Pro Gly Gln Ser Pro Lys Leu Leu
                165                 170                 175

Ile Tyr Lys Val Ser Asn Arg Phe Ser Gly Val Pro Asp Arg Phe Ser
            180                 185                 190

Gly Ser Gly Ser Gly Thr Asp Phe Thr Leu Lys Ile Ser Arg Val Glu
        195                 200                 205

Ala Glu Asp Leu Gly Val Tyr Tyr Cys Phe Gln Gly Ser His Val Pro
    210                 215                 220

Tyr Thr Phe Gly Gly Gly Thr Lys Leu Glu Ile Lys Arg Ala Ala Ala
225                 230                 235                 240

His His His His His His Gly Ala Ala Glu Gln Lys Leu Ile Ser Glu
                245                 250                 255

Glu Asp Leu Asn Gly Ala Ala
            260
```

<210> SEQ ID NO 101
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

```
Gln Val Gln Leu Lys Glu Ser Gly Ala Glu Leu Val Arg Pro Gly Thr
1               5                   10                  15
```

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

Thr Thr Val Thr Val Ser Ser Ala Ser Ser Ala Asp Ile Gln Met Thr
            115                 120                 125

Gln Thr Pro Leu Ser Leu Pro Val Ser Leu Gly Asp Gln Ala Ser Ile
    130                 135                 140

Ser Cys Arg Ser Ser Gln Ser Ile Val His Ser Asn Gly Asn Thr Tyr
145                 150                 155                 160

Leu Glu Trp Tyr Leu Gln Lys Pro Gly Gln Ser Pro Lys Leu Leu Ile
                165                 170                 175

Tyr Lys Val Ser Asn Arg Phe Ser Gly Val Pro Asp Arg Phe Ser Gly
            180                 185                 190

Ser Gly Ser Gly Thr Asp Phe Thr Leu Lys Ile Ser Arg Val Glu Ala
        195                 200                 205

Glu Asp Leu Gly Val Tyr Tyr Cys Phe Gln Gly Ser His Val Pro Tyr
    210                 215                 220

Thr Phe Gly Gly Gly Thr Lys Leu Glu Ile Lys Arg Ala Ala Ala His
225                 230                 235                 240

His His His His His Gly Ala Ala Glu Gln Lys Leu Ile Ser Glu Glu
                245                 250                 255

Asp Leu Asn Gly Ala Ala
            260

<210> SEQ ID NO 102
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

```
Thr Thr Val Thr Val Ser Ser Ala Ser Ala Asp Ile Gln Met Thr Gln
            115                 120                 125

Thr Pro Leu Ser Leu Pro Val Ser Leu Gly Asp Gln Ala Ser Ile Ser
            130                 135                 140

Cys Arg Ser Ser Gln Ser Ile Val His Ser Asn Gly Asn Thr Tyr Leu
145                 150                 155                 160

Glu Trp Tyr Leu Gln Lys Pro Gly Gln Ser Pro Lys Leu Leu Ile Tyr
                165                 170                 175

Lys Val Ser Asn Arg Phe Ser Gly Val Pro Asp Arg Phe Ser Gly Ser
            180                 185                 190

Gly Ser Gly Thr Asp Phe Thr Leu Lys Ile Ser Arg Val Glu Ala Glu
            195                 200                 205

Asp Leu Gly Val Tyr Tyr Cys Phe Gln Gly Ser His Val Pro Tyr Thr
            210                 215                 220

Phe Gly Gly Gly Thr Lys Leu Glu Ile Lys Arg Ala Ala His His
225                 230                 235                 240

His His His His Gly Ala Ala Glu Gln Lys Leu Ile Ser Glu Glu Asp
                245                 250                 255

Leu Asn Gly Ala Ala
            260

<210> SEQ ID NO 103
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

Thr Thr Val Thr Val Ser Ser Ala Ala Asp Ile Gln Met Thr Gln Thr
            115                 120                 125

Pro Leu Ser Leu Pro Val Ser Leu Gly Asp Gln Ala Ser Ile Ser Cys
            130                 135                 140

Arg Ser Ser Gln Ser Ile Val His Ser Asn Gly Asn Thr Tyr Leu Glu
145                 150                 155                 160

Trp Tyr Leu Gln Lys Pro Gly Gln Ser Pro Lys Leu Leu Ile Tyr Lys
                165                 170                 175

Val Ser Asn Arg Phe Ser Gly Val Pro Asp Arg Phe Ser Gly Ser Gly
            180                 185                 190

Ser Gly Thr Asp Phe Thr Leu Lys Ile Ser Arg Val Glu Ala Glu Asp
```

```
                    195                 200                 205
Leu Gly Val Tyr Tyr Cys Phe Gln Gly Ser His Val Pro Tyr Thr Phe
                210                 215                 220
Gly Gly Gly Thr Lys Leu Glu Ile Lys Arg Ala Ala His His His
225                 230                 235                 240
His His His Gly Ala Ala Glu Gln Lys Leu Ile Ser Glu Glu Asp Leu
                245                 250                 255
Asn Gly Ala Ala
            260

<210> SEQ ID NO 104
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Lys Glu Ser Gly Ala Glu Leu Val Arg Pro Gly Thr
1               5                   10                  15
Ser Val Lys Ile Ser Cys Lys Ala Ser Gly Tyr Thr Phe Thr Asn Tyr
                20                  25                  30
Trp Leu Gly Trp Val Lys Gln Arg Pro Gly His Gly Leu Glu Trp Ile
            35                  40                  45
Gly Asp Ile Tyr Pro Gly Gly Tyr Thr Asn Tyr Asn Glu Lys Phe
    50                  55                  60
Lys Gly Lys Ala Thr Leu Thr Ala Asp Thr Ser Ser Thr Ala Tyr
65                  70                  75                  80
Met Gln Leu Ser Ser Leu Thr Ser Glu Asp Ser Ala Val Tyr Phe Cys
                85                  90                  95
Ala Tyr Tyr Asp Ala Ala Gly Pro Gly Phe Ala Tyr Trp Gly Gln Gly
                100                 105                 110
Thr Thr Val Thr Val Ser Ser Ala Asp Ile Gln Met Thr Gln Thr Pro
            115                 120                 125
Leu Ser Leu Pro Val Ser Leu Gly Asp Gln Ala Ser Ile Ser Cys Arg
    130                 135                 140
Ser Ser Gln Ser Ile Val His Ser Asn Gly Asn Thr Tyr Leu Glu Trp
145                 150                 155                 160
Tyr Leu Gln Lys Pro Gly Gln Ser Pro Lys Leu Leu Ile Tyr Lys Val
                165                 170                 175
Ser Asn Arg Phe Ser Gly Val Pro Asp Arg Phe Ser Gly Ser Gly Ser
                180                 185                 190
Gly Thr Asp Phe Thr Leu Lys Ile Ser Arg Val Glu Ala Glu Asp Leu
            195                 200                 205
Gly Val Tyr Tyr Cys Phe Gln Gly Ser His Val Pro Tyr Thr Phe Gly
    210                 215                 220
Gly Gly Thr Lys Leu Glu Ile Lys Arg Ala Ala Ala His His His His
225                 230                 235                 240
His His Gly Ala Ala Glu Gln Lys Leu Ile Ser Glu Glu Asp Leu Asn
                245                 250                 255
Gly Ala Ala

<210> SEQ ID NO 105
<211> LENGTH: 258
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 105

```
Gln Val Gln Leu Lys Glu Ser Gly Ala Glu Leu Val Arg Pro Gly Thr
1               5                   10                  15
Ser Val Lys Ile Ser Cys Lys Ala Ser Gly Tyr Thr Phe Thr Asn Tyr
                20                  25                  30
Trp Leu Gly Trp Val Lys Gln Arg Pro Gly His Gly Leu Glu Trp Ile
            35                  40                  45
Gly Asp Ile Tyr Pro Gly Gly Tyr Thr Asn Tyr Asn Glu Lys Phe
 50                  55                  60
Lys Gly Lys Ala Thr Leu Thr Ala Asp Thr Ser Ser Ser Thr Ala Tyr
65                  70                  75                  80
Met Gln Leu Ser Ser Leu Thr Ser Glu Asp Ser Ala Val Tyr Phe Cys
                85                  90                  95
Ala Tyr Tyr Asp Ala Ala Gly Pro Gly Phe Ala Tyr Trp Gly Gln Gly
                100                 105                 110
Thr Thr Val Thr Val Ser Ser Asp Ile Gln Met Thr Gln Thr Pro Leu
            115                 120                 125
Ser Leu Pro Val Ser Leu Gly Asp Gln Ala Ser Ile Ser Cys Arg Ser
130                 135                 140
Ser Gln Ser Ile Val His Ser Asn Gly Asn Thr Tyr Leu Glu Trp Tyr
145                 150                 155                 160
Leu Gln Lys Pro Gly Gln Ser Pro Lys Leu Leu Ile Tyr Lys Val Ser
                165                 170                 175
Asn Arg Phe Ser Gly Val Pro Asp Arg Phe Ser Gly Ser Gly Ser Gly
            180                 185                 190
Thr Asp Phe Thr Leu Lys Ile Ser Arg Val Glu Ala Glu Asp Leu Gly
        195                 200                 205
Val Tyr Tyr Cys Phe Gln Gly Ser His Val Pro Tyr Thr Phe Gly Gly
210                 215                 220
Gly Thr Lys Leu Glu Ile Lys Arg Ala Ala Ala His His His His
225                 230                 235                 240
His Gly Ala Ala Glu Gln Lys Leu Ile Ser Glu Glu Asp Leu Asn Gly
                245                 250                 255
Ala Ala
```

<210> SEQ ID NO 106
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Gln Val Gln Leu Lys Glu Ser Gly Ala Glu Leu Val Arg Pro Gly Thr
1               5                   10                  15
Ser Val Lys Ile Ser Cys Lys Ala Ser Gly Tyr Thr Phe Thr Asn Tyr
                20                  25                  30
Trp Leu Gly Trp Val Lys Gln Arg Pro Gly His Gly Leu Glu Trp Ile
            35                  40                  45
Gly Asp Ile Tyr Pro Gly Gly Gly Tyr Thr Asn Tyr Asn Glu Lys Phe
 50                  55                  60
```

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Gly Phe Ala Tyr Trp Gly Gln Gly
            100                 105                 110

Thr Thr Val Thr Val Ser Asp Ile Gln Met Thr Gln Thr Pro Leu Ser
            115                 120                 125

Leu Pro Val Ser Leu Gly Asp Gln Ala Ser Ile Ser Cys Arg Ser Ser
130                 135                 140

Gln Ser Ile Val His Ser Asn Gly Asn Thr Tyr Leu Glu Trp Tyr Leu
145                 150                 155                 160

Gln Lys Pro Gly Gln Ser Pro Lys Leu Leu Ile Tyr Lys Val Ser Asn
                165                 170                 175

Arg Phe Ser Gly Val Pro Asp Arg Phe Ser Gly Ser Gly Ser Gly Thr
            180                 185                 190

Asp Phe Thr Leu Lys Ile Ser Arg Val Glu Ala Glu Asp Leu Gly Val
            195                 200                 205

Tyr Tyr Cys Phe Gln Gly Ser His Val Pro Tyr Thr Phe Gly Gly Gly
210                 215                 220

Thr Lys Leu Glu Ile Lys Arg Ala Ala Ala His His His His His His
225                 230                 235                 240

Gly Ala Ala Glu Gln Lys Leu Ile Ser Glu Glu Asp Leu Asn Gly Ala
                245                 250                 255

Ala

<210> SEQ ID NO 107
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Val Ile Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
            165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
            210                 215

<210> SEQ ID NO 108
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
            165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
            210                 215

<210> SEQ ID NO 109
<211> LENGTH: 571
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Lys Gln Ser Gly Ala Glu Leu Val Arg Pro Gly Thr
1               5                   10                  15

-continued

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Ser Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Asp Asn His Tyr Phe Asp Tyr Trp Gly Gln Gly Thr Thr
            100                 105                 110

Leu Thr Val Ser Glu Ser Gln Ser Phe Pro Asn Val Phe Pro Leu Val
        115                 120                 125

Ser Cys Glu Ser Pro Leu Ser Asp Lys Asn Leu Val Ala Met Gly Cys
    130                 135                 140

Leu Ala Arg Asp Phe Leu Pro Ser Thr Ile Ser Phe Thr Trp Asn Tyr
145                 150                 155                 160

Gln Asn Asn Thr Glu Val Ile Gln Gly Ile Arg Thr Phe Pro Thr Leu
                165                 170                 175

Arg Thr Gly Gly Lys Tyr Leu Ala Thr Ser Gln Val Leu Leu Ser Pro
            180                 185                 190

Lys Ser Ile Leu Glu Gly Ser Asp Glu Tyr Leu Val Cys Lys Ile His
        195                 200                 205

Tyr Gly Gly Lys Asn Arg Asp Leu His Val Pro Ile Pro Ala Val Ala
    210                 215                 220

Glu Met Asn Pro Asn Val Asn Val Phe Val Pro Pro Arg Asp Gly Phe
225                 230                 235                 240

Ser Gly Pro Ala Pro Arg Lys Ser Lys Leu Ile Cys Glu Ala Thr Asn
                245                 250                 255

Phe Thr Pro Lys Pro Ile Thr Val Ser Trp Leu Lys Asp Gly Lys Leu
            260                 265                 270

Val Glu Ser Gly Phe Thr Thr Asp Pro Val Thr Ile Glu Asn Lys Gly
        275                 280                 285

Ser Thr Pro Gln Thr Tyr Lys Val Ile Ser Thr Leu Thr Ile Ser Glu
    290                 295                 300

Ile Asp Trp Leu Asn Leu Asn Val Tyr Thr Cys Arg Val Asp His Arg
305                 310                 315                 320

Gly Leu Thr Phe Leu Lys Asn Val Ser Ser Thr Cys Ala Ala Ser Pro
                325                 330                 335

Ser Thr Asp Ile Leu Thr Phe Thr Ile Pro Pro Ser Phe Ala Asp Ile
            340                 345                 350

Phe Leu Ser Lys Ser Ala Asn Leu Thr Cys Leu Val Ser Asn Leu Ala
        355                 360                 365

Thr Tyr Glu Thr Leu Asn Ile Ser Trp Ala Ser Gln Ser Gly Glu Pro
    370                 375                 380

Leu Glu Thr Lys Ile Lys Ile Met Glu Ser His Pro Asn Gly Thr Phe
385                 390                 395                 400

Ser Ala Lys Gly Val Ala Ser Val Cys Val Glu Asp Trp Asn Asn Arg
                405                 410                 415

Lys Glu Phe Val Cys Thr Val Thr His Arg Asp Leu Pro Ser Pro Gln
            420                 425                 430

```
Lys Lys Phe Ile Ser Lys Pro Asn Glu Val His Lys His Pro Pro Ala
            435                 440                 445

Val Tyr Leu Leu Pro Pro Ala Arg Glu Gln Leu Asn Leu Arg Glu Ser
450                 455                 460

Ala Thr Val Thr Cys Leu Val Lys Gly Phe Ser Pro Ala Asp Ile Ser
465                 470                 475                 480

Val Gln Trp Leu Gln Arg Gly Gln Leu Leu Pro Gln Glu Lys Tyr Val
                485                 490                 495

Thr Ser Ala Pro Met Pro Glu Pro Gly Ala Pro Gly Phe Tyr Phe Thr
            500                 505                 510

His Ser Ile Leu Thr Val Thr Glu Glu Glu Trp Asn Ser Gly Glu Thr
        515                 520                 525

Tyr Thr Cys Val Val Gly His Glu Ala Leu Pro His Leu Val Thr Glu
530                 535                 540

Arg Thr Val Asp Lys Ser Thr Gly Lys Pro Thr Leu Tyr Asn Val Ser
545                 550                 555                 560

Leu Ile Met Ser Asp Thr Gly Thr Cys Tyr
                565                 570

<210> SEQ ID NO 110
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Thr Val Thr Val Ser Glu Ser Gln Ser Phe Pro Asn Val Phe Pro
        115                 120                 125

Leu Val Ser Cys Glu Ser Pro Leu Ser Asp Lys Asn Leu Val Ala Met
    130                 135                 140

Gly Cys Leu Ala Arg Asp Phe Leu Pro Ser Thr Ile Ser Phe Thr Trp
145                 150                 155                 160

Asn Tyr Gln Asn Asn Thr Glu Val Ile Gln Gly Ile Arg Thr Phe Pro
                165                 170                 175

Thr Leu Arg Thr Gly Gly Lys Tyr Leu Ala Thr Ser Gln Val Leu Leu
            180                 185                 190

Ser Pro Lys Ser Ile Leu Glu Gly Ser Asp Glu Tyr Leu Val Cys Lys
        195                 200                 205

Ile His Tyr Gly Gly Lys Asn Arg Asp Leu His Val Pro Ile Pro Ala
    210                 215                 220
```

Val Ala Glu Met Asn Pro Asn Val Asn Val Phe Val Pro Pro Arg Asp
225                 230                 235                 240

Gly Phe Ser Gly Pro Ala Pro Arg Lys Ser Lys Leu Ile Cys Glu Ala
                245                 250                 255

Thr Asn Phe Thr Pro Lys Pro Ile Thr Val Ser Trp Leu Lys Asp Gly
            260                 265                 270

Lys Leu Val Glu Ser Gly Phe Thr Thr Asp Pro Val Thr Ile Glu Asn
        275                 280                 285

Lys Gly Ser Thr Pro Gln Thr Tyr Lys Val Ile Ser Thr Leu Thr Ile
    290                 295                 300

Ser Glu Ile Asp Trp Leu Asn Leu Asn Val Tyr Thr Cys Arg Val Asp
305                 310                 315                 320

His Arg Gly Leu Thr Phe Leu Lys Asn Val Ser Ser Thr Cys Ala Ala
                325                 330                 335

Ser Pro Ser Thr Asp Ile Leu Thr Phe Thr Ile Pro Pro Ser Phe Ala
            340                 345                 350

Asp Ile Phe Leu Ser Lys Ser Ala Asn Leu Thr Cys Leu Val Ser Asn
        355                 360                 365

Leu Ala Thr Tyr Glu Thr Leu Asn Ile Ser Trp Ala Ser Gln Ser Gly
    370                 375                 380

Glu Pro Leu Glu Thr Lys Ile Lys Ile Met Glu Ser His Pro Asn Gly
385                 390                 395                 400

Thr Phe Ser Ala Lys Gly Val Ala Ser Val Cys Val Glu Asp Trp Asn
                405                 410                 415

Asn Arg Lys Glu Phe Val Cys Thr Val Thr His Arg Asp Leu Pro Ser
            420                 425                 430

Pro Gln Lys Lys Phe Ile Ser Lys Pro Asn Glu Val His Lys His Pro
        435                 440                 445

Pro Ala Val Tyr Leu Leu Pro Pro Ala Arg Glu Gln Leu Asn Leu Arg
    450                 455                 460

Glu Ser Ala Thr Val Thr Cys Leu Val Lys Gly Phe Ser Pro Ala Asp
465                 470                 475                 480

Ile Ser Val Gln Trp Leu Gln Arg Gly Gln Leu Leu Pro Gln Glu Lys
                485                 490                 495

Tyr Val Thr Ser Ala Pro Met Pro Glu Pro Gly Ala Pro Gly Phe Tyr
            500                 505                 510

Phe Thr His Ser Ile Leu Thr Val Thr Glu Glu Glu Trp Asn Ser Gly
        515                 520                 525

Glu Thr Tyr Thr Cys Val Val Gly His Glu Ala Leu Pro His Leu Val
    530                 535                 540

Thr Glu Arg Thr Val Asp Lys Ser Thr Gly Lys Pro Thr Leu Tyr Asn
545                 550                 555                 560

Val Ser Leu Ile Met Ser Asp Thr Gly Gly Thr Cys Tyr
                565                 570

<210> SEQ ID NO 111
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Lys Glu Ser Gly Ala Glu Leu Val Arg Pro Gly Thr

-continued

```
1               5                   10                  15
Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
                100                 105                 110

Thr Thr Val Thr Val Ser Gly Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430
```

```
Leu His Asn His Tyr Thr Gln Lys Ser Leu Ser Leu Ser Pro Gly Lys
        435                 440                 445
```

<210> SEQ ID NO 112
<211> LENGTH: 571
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Gln Val Gln Leu Lys Glu Ser Gly Ala Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Tyr Tyr Asp Ala Ala Gly Pro Trp Phe Ala Tyr Trp Gly Gln Gly
            100                 105                 110

Thr Thr Val Thr Val Ser Gly Ser Ala Ser Ala Pro Thr Leu Phe Pro
        115                 120                 125

Leu Val Ser Cys Glu Asn Ser Pro Ser Asp Thr Ser Ser Val Ala Val
    130                 135                 140

Gly Cys Leu Ala Gln Asp Phe Leu Pro Asp Ser Ile Thr Leu Ser Trp
145                 150                 155                 160

Lys Tyr Lys Asn Asn Ser Asp Ile Ser Ser Thr Arg Gly Phe Pro Ser
                165                 170                 175

Val Leu Arg Gly Gly Lys Tyr Ala Ala Thr Ser Gln Val Leu Leu Pro
            180                 185                 190

Ser Lys Asp Val Met Gln Gly Thr Asp Glu His Val Val Cys Lys Val
        195                 200                 205

Gln His Pro Asn Gly Asn Lys Glu Lys Asn Val Pro Leu Pro Val Ile
    210                 215                 220

Ala Glu Leu Pro Pro Lys Val Ser Val Phe Val Pro Pro Arg Asp Gly
225                 230                 235                 240

Phe Phe Gly Asn Pro Arg Lys Ser Lys Leu Ile Cys Gln Ala Thr Gly
                245                 250                 255

Phe Ser Pro Arg Gln Ile Gln Val Ser Trp Leu Arg Glu Gly Lys Gln
            260                 265                 270

Val Gly Ser Gly Val Thr Thr Asp Gln Val Gln Ala Glu Ala Lys Glu
        275                 280                 285

Ser Gly Pro Thr Thr Tyr Lys Val Thr Ser Thr Leu Thr Ile Lys Glu
    290                 295                 300

Ser Asp Trp Leu Gly Gln Ser Met Phe Thr Cys Arg Val Asp His Arg
305                 310                 315                 320

Gly Leu Thr Phe Gln Gln Asn Ala Ser Ser Met Cys Val Pro Asp Gln
                325                 330                 335

Asp Thr Ala Ile Arg Val Phe Ala Ile Pro Pro Ser Phe Ala Ser Ile
```

```
                    340                 345                 350
Phe Leu Thr Lys Ser Thr Lys Leu Thr Cys Leu Val Thr Asp Leu Thr
                355                 360                 365

Thr Tyr Asp Ser Val Thr Ile Ser Trp Thr Arg Gln Asn Gly Glu Ala
            370                 375                 380

Val Lys Thr His Thr Asn Ile Ser Glu Ser His Pro Asn Ala Thr Phe
385                 390                 395                 400

Ser Ala Val Gly Glu Ala Ser Ile Cys Glu Asp Asp Trp Asn Ser Gly
                405                 410                 415

Glu Arg Phe Thr Cys Thr Val Thr His Thr Asp Leu Pro Ser Pro Leu
            420                 425                 430

Lys Gln Thr Ile Ser Arg Pro Lys Gly Val Ala Leu His Arg Pro Asp
                435                 440                 445

Val Tyr Leu Leu Pro Pro Ala Arg Glu Gln Leu Asn Leu Arg Glu Ser
            450                 455                 460

Ala Thr Ile Thr Cys Leu Val Thr Gly Phe Ser Pro Ala Asp Val Phe
465                 470                 475                 480

Val Gln Trp Met Gln Arg Gly Gln Pro Leu Ser Pro Glu Lys Tyr Val
                485                 490                 495

Thr Ser Ala Pro Met Pro Glu Pro Gln Ala Pro Gly Arg Tyr Phe Ala
            500                 505                 510

His Ser Ile Leu Thr Val Ser Glu Glu Glu Trp Asn Thr Gly Glu Thr
                515                 520                 525

Tyr Thr Cys Val Val Ala His Glu Ala Leu Pro Asn Arg Val Thr Glu
            530                 535                 540

Arg Thr Val Asp Lys Ser Thr Gly Lys Pro Thr Leu Tyr Asn Val Ser
545                 550                 555                 560

Leu Val Met Ser Asp Thr Ala Gly Thr Cys Tyr
                565                 570

<210> SEQ ID NO 113
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Ile Gln Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 114
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(63)

<400> SEQUENCE: 114 acg gtc acc gtc tcc tca gcc tcg agt ggc tcg ggc tca tct gca gat     48
Thr Val Thr Val Ser Ser Ala Ser Ser Gly Ser Gly Ser Ser Ala Asp
1               5                   10                  15 atc cag atg aca cag                                                 63
Ile Gln Met Thr Gln
            20

<210> SEQ ID NO 115
<211> LENGTH: 21
<212> TYPE: PRT
<213> ORGANISM: Artificial Sequence
<220> FEATURE:
<223> OTHER INFORMATION: Synthetic Construct

<400> SEQUENCE: 115

Thr Val Thr Val Ser Ser Ala Ser Ser Gly Ser Gly Ser Ser Ala Asp
1               5                   10                  15

Ile Gln Met Thr Gln
            20

<210> SEQ ID NO 116
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(60)

<400> SEQUENCE: 116 acg gtc acc gtc tcc tca gcc tcg agt ggc ggc tca tct gca gat atc     48
Thr Val Thr Val Ser Ser Ala Ser Ser Gly Gly Ser Ser Ala Asp Ile
1               5                   10                  15 cag atg aca cag                                                     60
Gln Met Thr Gln
            20
```

```
<210> SEQ ID NO 117
<211> LENGTH: 20
<212> TYPE: PRT
<213> ORGANISM: Artificial Sequence
<220> FEATURE:
<223> OTHER INFORMATION: Synthetic Construct

<400> SEQUENCE: 117

Thr Val Thr Val Ser Ser Ala Ser Ser Gly Gly Ser Ser Ala Asp Ile
1               5                   10                  15

Gln Met Thr Gln
            20

<210> SEQ ID NO 118
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(57)

<400> SEQUENCE: 118 acg gtc acc gtc tcc tca gcc tcg agt ggc tca tct gca gat atc cag      48
Thr Val Thr Val Ser Ser Ala Ser Ser Gly Ser Ser Ala Asp Ile Gln
1               5                   10                  15 atg aca cag                                                          57
Met Thr Gln <210> SEQ ID NO 119
<211> LENGTH: 19
<212> TYPE: PRT
<213> ORGANISM: Artificial Sequence
<220> FEATURE:
<223> OTHER INFORMATION: Synthetic Construct

<400> SEQUENCE: 119

Thr Val Thr Val Ser Ser Ala Ser Ser Gly Ser Ser Ala Asp Ile Gln
1               5                   10                  15

Met Thr Gln

<210> SEQ ID NO 120
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(54)

<400> SEQUENCE: 120 acg gtc acc gtc tcc tca gcc tcg agt tca tct gca gat atc cag atg      48
Thr Val Thr Val Ser Ser Ala Ser Ser Ser Ser Ala Asp Ile Gln Met
1               5                   10                  15 aca cag                                                              54
Thr Gln

<210> SEQ ID NO 121
<211> LENGTH: 18
<212> TYPE: PRT
<213> ORGANISM: Artificial Sequence
<220> FEATURE:
<223> OTHER INFORMATION: Synthetic Construct
```

<400> SEQUENCE: 121

Thr Val Thr Val Ser Ser Ala Ser Ser Ser Ala Asp Ile Gln Met
1               5                   10                  15

Thr Gln

<210> SEQ ID NO 122
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 122 acg gtc acc gtc tcc tca gcc tcg agt tct gca gat atc cag atg aca       48
Thr Val Thr Val Ser Ser Ala Ser Ser Ser Ala Asp Ile Gln Met Thr
1               5                   10                  15 cag                                                                    51
Gln

<210> SEQ ID NO 123
<211> LENGTH: 17
<212> TYPE: PRT
<213> ORGANISM: Artificial Sequence
<220> FEATURE:
<223> OTHER INFORMATION: Synthetic Construct

<400> SEQUENCE: 123

Thr Val Thr Val Ser Ser Ala Ser Ser Ser Ala Asp Ile Gln Met Thr
1               5                   10                  15

Gln

<210> SEQ ID NO 124
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(48)

<400> SEQUENCE: 124 acg gtc acc gtc tcc tca gcc tcg agt gca gat atc cag atg aca cag       48
Thr Val Thr Val Ser Ser Ala Ser Ala Asp Ile Gln Met Thr Gln
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Synthetic Construct

<400> SEQUENCE: 125

Thr Val Thr Val Ser Ser Ala Ser Ser Ala Asp Ile Gln Met Thr Gln
1               5                   10                  15

<210> SEQ ID NO 126
<211> LENGTH: 45
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 126 acg gtc acc gtc tcc tca gcc tcg gcc gat atc cag atg aca cag        45
Thr Val Thr Val Ser Ser Ala Ser Ala Asp Ile Gln Met Thr Gln
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Synthetic Construct

<400> SEQUENCE: 127

Thr Val Thr Val Ser Ser Ala Ser Ala Asp Ile Gln Met Thr Gln
1               5                   10                  15

<210> SEQ ID NO 128
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(42)

<400> SEQUENCE: 128 acg gtc acc gtc tcc tca gcc gcc gat atc cag atg aca cag            42
Thr Val Thr Val Ser Ser Ala Ala Asp Ile Gln Met Thr Gln
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Synthetic Construct

<400> SEQUENCE: 129

Thr Val Thr Val Ser Ser Ala Ala Asp Ile Gln Met Thr Gln
1               5                   10

<210> SEQ ID NO 130
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(39)

<400> SEQUENCE: 130 acg gtc acc gtc tcc tca gcc gat atc cag atg aca cag                39
Thr Val Thr Val Ser Ser Ala Asp Ile Gln Met Thr Gln
1               5                   10

<210> SEQ ID NO 131
<211> LENGTH: 13
```

```
<212> TYPE: PRT
<213> ORGANISM: Artificial Sequence
<220> FEATURE:
<223> OTHER INFORMATION: Synthetic Construct

<400> SEQUENCE: 131

Thr Val Thr Val Ser Ser Ala Asp Ile Gln Met Thr Gln
1               5                   10

<210> SEQ ID NO 132
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 132 acg gtc acc gtc tcc tca gat atc cag atg aca cag          36
Thr Val Thr Val Ser Ser Asp Ile Gln Met Thr Gln
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Synthetic Construct

<400> SEQUENCE: 133

Thr Val Thr Val Ser Ser Asp Ile Gln Met Thr Gln
1               5                   10

<210> SEQ ID NO 134
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 134 acg gtc acc gtc tcc gat atc cag atg aca cag              33
Thr Val Thr Val Ser Asp Ile Gln Met Thr Gln
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic Construct

<400> SEQUENCE: 135

Thr Val Thr Val Ser Asp Ile Gln Met Thr Gln
1               5                   10

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
```

6xHis tag

<400> SEQUENCE: 136

His His His His His His
1               5

<210> SEQ ID NO 137
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
aattggatcc gagcccagac actggac                                      27

<210> SEQ ID NO 138
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
accgtctaga cgcactcatt tacccgg                                      27

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
acctggatcc gctaggaaga aactcaaaac                                   30

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
accgtctaga ccctctaaca ctctcccctg                                   30

<210> SEQ ID NO 141
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
atcgggatcc gatagccatg acagtctg                                     28

<210> SEQ ID NO 142
<211> LENGTH: 26
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 142
agcgtctaga cagggtcagt agcagg                                         26

<210> SEQ ID NO 143
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Glu
<220> FEATURE:
<221> NAME/KEY: MOD_RES
<222> LOCATION: (3)..(3)
<223> OTHER INFORMATION: Gln, Lys or Thr
<220> FEATURE:
<221> NAME/KEY: MOD_RES
<222> LOCATION: (5)..(5)
<223> OTHER INFORMATION: Lys or Val
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (11)..(11)
<223> OTHER INFORMATION: Leu or Val
<220> FEATURE:
<221> NAME/KEY: MOD_RES
<222> LOCATION: (12)..(12)
<223> OTHER INFORMATION: Val or Lys
<220> FEATURE:
<221> NAME/KEY: MOD_RES
<222> LOCATION: (13)..(13)
<223> OTHER INFORMATION: Arg or Lys
<220> FEATURE:
<221> NAME/KEY: MOD_RES
<222> LOCATION: (16)..(16)
<223> OTHER INFORMATION: Thr or Ala
<220> FEATURE:
<221> NAME/KEY: MOD_RES
<222> LOCATION: (20)..(20)
<223> OTHER INFORMATION: Ile or Val
<220> FEATURE:
<221> NAME/KEY: MOD_RES
<222> LOCATION: (21)..(21)
<223> OTHER INFORMATION: Ser or Pro
<220> FEATURE:
<221> NAME/KEY: MOD_RES
<222> LOCATION: (24)..(24)
<223> OTHER INFORMATION: Ala, Val, Ser or Thr
<220> FEATURE:
<221> NAME/KEY: MOD_RES
<222> LOCATION: (27)..(27)
<223> OTHER INFORMATION: Tyr, Phe, Ser or Asp
<220> FEATURE:
<221> NAME/KEY: MOD_RES
<222> LOCATION: (29)..(29)
<223> OTHER INFORMATION: Phe, Leu or Ile

<400> SEQUENCE: 143

Xaa Val Xaa Leu Xaa Xaa Ser Gly Ala Glu Xaa Xaa Xaa Pro Gly Xaa
1               5                   10                  15

Ser Val Lys Xaa Xaa Cys Lys Xaa Ser Gly Xaa Thr Xaa Thr
            20                  25                  30

<210> SEQ ID NO 144
<211> LENGTH: 14
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys or Arg
<220> FEATURE:
<221> NAME/KEY: MOD_RES
<222> LOCATION: (5)..(5)
<223> OTHER INFORMATION: Arg or Ala
<220> FEATURE:
<221> NAME/KEY: MOD_RES
<222> LOCATION: (8)..(8)
<223> OTHER INFORMATION: His or Gln
<220> FEATURE:
<221> NAME/KEY: MOD_RES
<222> LOCATION: (12)..(12)
<223> OTHER INFORMATION: Trp or Arg
<220> FEATURE:
<221> NAME/KEY: MOD_RES
<222> LOCATION: (13)..(13)
<223> OTHER INFORMATION: Ile or Met

<400> SEQUENCE: 144

Trp Val Xaa Gln Xaa Pro Gly Xaa Gly Leu Glu Xaa Xaa Gly
1               5                   10

<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (2)..(2)
<223> OTHER INFORMATION: Ala or Val
<220> FEATURE:
<221> NAME/KEY: MOD_RES
<222> LOCATION: (4)..(4)
<223> OTHER INFORMATION: Leu or Met
<220> FEATURE:
<221> NAME/KEY: MOD_RES
<222> LOCATION: (6)..(6)
<223> OTHER INFORMATION: Ala, Leu or Thr
<220> FEATURE:
<221> NAME/KEY: MOD_RES
<222> LOCATION: (10)..(10)
<223> OTHER INFORMATION: Ser or Thr
<220> FEATURE:
<221> NAME/KEY: MOD_RES
<222> LOCATION: (16)..(16)
<223> OTHER INFORMATION: Gln or Glu
<220> FEATURE:
<221> NAME/KEY: MOD_RES
<222> LOCATION: (19)..(19)
<223> OTHER INFORMATION: Ser or Arg
<220> FEATURE:
<221> NAME/KEY: MOD_RES
<222> LOCATION: (21)..(21)
<223> OTHER INFORMATION: Thr or Arg
<220> FEATURE:
<221> NAME/KEY: MOD_RES
<222> LOCATION: (25)..(25)
<223> OTHER INFORMATION: Ser or Thr
<220> FEATURE:
<221> NAME/KEY: MOD_RES
<222> LOCATION: (29)..(29)
<223> OTHER INFORMATION: Phe or Tyr
<220> FEATURE:
```

```
<221> NAME/KEY: MOD_RES
<222> LOCATION: (32)..(32)
<223> OTHER INFORMATION: Tyr, Lys or Arg

<400> SEQUENCE: 145

Xaa Xaa Thr Xaa Thr Xaa Asp Thr Ser Xaa Ser Thr Ala Tyr Met Xaa
1               5                   10                  15

Leu Ser Xaa Leu Xaa Ser Glu Asp Xaa Ala Val Tyr Xaa Cys Ala Xaa
            20                  25                  30

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Thr, Ser or Leu
<220> FEATURE:
<221> NAME/KEY: MOD_RES
<222> LOCATION: (7)..(7)
<223> OTHER INFORMATION: Val or Leu
<220> FEATURE:
<221> NAME/KEY: MOD_RES
<222> LOCATION: (11)..(11)
<223> OTHER INFORMATION: Ser or Ala

<400> SEQUENCE: 146

Trp Gly Gln Gly Thr Xaa Xaa Thr Val Ser Xaa
1               5                   10

<210> SEQ ID NO 147
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, Val or Leu
<220> FEATURE:
<221> NAME/KEY: MOD_RES
<222> LOCATION: (3)..(3)
<223> OTHER INFORMATION: Gln or Leu
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Leu or Phe
<220> FEATURE:
<221> NAME/KEY: MOD_RES
<222> LOCATION: (17)..(17)
<223> OTHER INFORMATION: Asp or Glu
<220> FEATURE:
<221> NAME/KEY: MOD_RES
<222> LOCATION: (18)..(18)
<223> OTHER INFORMATION: Gln or Pro

<400> SEQUENCE: 147

Asp Xaa Xaa Met Thr Gln Xaa Pro Leu Ser Leu Pro Val Xaa Xaa Gly
1               5                   10                  15
```

```
Xaa Xaa Ala Ser Ile Ser Cys
            20

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys or Gln
<220> FEATURE:
<221> NAME/KEY: MOD_RES
<222> LOCATION: (14)..(14)
<223> OTHER INFORMATION: Ile or Val

<400> SEQUENCE: 148

Trp Tyr Leu Gln Lys Pro Gly Gln Ser Pro Xaa Leu Leu Xaa Tyr
1               5                   10                  15

<210> SEQ ID NO 149
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Leu or Val

<400> SEQUENCE: 149

Gly Val Pro Asp Arg Phe Ser Gly Ser Gly Ser Gly Thr Asp Phe Thr
1               5                   10                  15

Leu Lys Ile Ser Arg Val Glu Ala Glu Asp Xaa Gly Val Tyr Tyr Cys
            20                  25                  30

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly or Gln
<220> FEATURE:
<221> NAME/KEY: MOD_RES
<222> LOCATION: (9)..(9)
<223> OTHER INFORMATION: Ile or Leu

<400> SEQUENCE: 150

Phe Gly Xaa Gly Thr Lys Leu Glu Xaa Lys Arg Ala
1               5                   10

<210> SEQ ID NO 151
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (1)..(1)
<223> OTHER INFORMATION: Gln or Glu
<220> FEATURE:
<221> NAME/KEY: MOD_RES
<222> LOCATION: (3)..(3)
<223> OTHER INFORMATION: Gln, Lys or Thr
<220> FEATURE:
<221> NAME/KEY: MOD_RES
<222> LOCATION: (5)..(5)
<223> OTHER INFORMATION: Lys or Val
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (11)..(11)
<223> OTHER INFORMATION: Leu or Val
<220> FEATURE:
<221> NAME/KEY: MOD_RES
<222> LOCATION: (12)..(12)
<223> OTHER INFORMATION: Val or Lys
<220> FEATURE:
<221> NAME/KEY: MOD_RES
<222> LOCATION: (13)..(13)
<223> OTHER INFORMATION: Arg or Lys
<220> FEATURE:
<221> NAME/KEY: MOD_RES
<222> LOCATION: (16)..(16)
<223> OTHER INFORMATION: Thr or Ala
<220> FEATURE:
<221> NAME/KEY: MOD_RES
<222> LOCATION: (20)..(20)
<223> OTHER INFORMATION: Ile or Val
<220> FEATURE:
<221> NAME/KEY: MOD_RES
<222> LOCATION: (21)..(21)
<223> OTHER INFORMATION: Ser or Pro
<220> FEATURE:
<221> NAME/KEY: MOD_RES
<222> LOCATION: (24)..(24)
<223> OTHER INFORMATION: Ala, Val, Ser or Thr
<220> FEATURE:
<221> NAME/KEY: MOD_RES
<222> LOCATION: (27)..(27)
<223> OTHER INFORMATION: Tyr, Phe, Ser or Asp
<220> FEATURE:
<221> NAME/KEY: MOD_RES
<222> LOCATION: (29)..(29)
<223> OTHER INFORMATION: Phe, Leu, or Ile
<220> FEATURE:
<221> NAME/KEY: MOD_RES
<222> LOCATION: (31)..(31)
<223> OTHER INFORMATION: Asn or any amino acid
<220> FEATURE:
<221> NAME/KEY: MOD_RES
<222> LOCATION: (32)..(32)
<223> OTHER INFORMATION: Tyr or any amino acid
<220> FEATURE:
<221> NAME/KEY: MOD_RES
<222> LOCATION: (33)..(33)
<223> OTHER INFORMATION: Trp or any amino acid
<220> FEATURE:
<221> NAME/KEY: MOD_RES
<222> LOCATION: (34)..(34)
<223> OTHER INFORMATION: Leu or any amino acid
<220> FEATURE:
<221> NAME/KEY: MOD_RES
<222> LOCATION: (35)..(35)
<223> OTHER INFORMATION: Gly or any amino acid
<220> FEATURE:
<221> NAME/KEY: MOD_RES
<222> LOCATION: (38)..(38)
<223> OTHER INFORMATION: Lys or Arg
<220> FEATURE:
<221> NAME/KEY: MOD_RES
<222> LOCATION: (40)..(40)
<223> OTHER INFORMATION: Arg or Ala
<220> FEATURE:
```

```
<221> NAME/KEY: MOD_RES
<222> LOCATION: (43)..(43)
<223> OTHER INFORMATION: His or Gln
<220> FEATURE:
<221> NAME/KEY: MOD_RES
<222> LOCATION: (47)..(47)
<223> OTHER INFORMATION: Trp or Arg
<220> FEATURE:
<221> NAME/KEY: MOD_RES
<222> LOCATION: (48)..(48)
<223> OTHER INFORMATION: Ile or Met
<220> FEATURE:
<221> NAME/KEY: MOD_RES
<222> LOCATION: (50)..(50)
<223> OTHER INFORMATION: Asp or any amino acid
<220> FEATURE:
<221> NAME/KEY: MOD_RES
<222> LOCATION: (51)..(51)
<223> OTHER INFORMATION: Ile or any amino acid
<220> FEATURE:
<221> NAME/KEY: MOD_RES
<222> LOCATION: (52)..(52)
<223> OTHER INFORMATION: Tyr or any amino acid
<220> FEATURE:
<221> NAME/KEY: MOD_RES
<222> LOCATION: (53)..(53)
<223> OTHER INFORMATION: Pro or any amino acid
<220> FEATURE:
<221> NAME/KEY: MOD_RES
<222> LOCATION: (54)..(55)
<223> OTHER INFORMATION: Gly or any amino acid
<220> FEATURE:
<221> NAME/KEY: MOD_RES
<222> LOCATION: (56)..(56)
<223> OTHER INFORMATION: Gly, Ser or any amino acid
<220> FEATURE:
<221> NAME/KEY: MOD_RES
<222> LOCATION: (57)..(57)
<223> OTHER INFORMATION: Tyr or any amino acid
<220> FEATURE:
<221> NAME/KEY: MOD_RES
<222> LOCATION: (58)..(58)
<223> OTHER INFORMATION: Thr or any amino acid
<220> FEATURE:
<221> NAME/KEY: MOD_RES
<222> LOCATION: (59)..(59)
<223> OTHER INFORMATION: Asn or any amino acid
<220> FEATURE:
<221> NAME/KEY: MOD_RES
<222> LOCATION: (60)..(60)
<223> OTHER INFORMATION: Tyr or any amino acid
<220> FEATURE:
<221> NAME/KEY: MOD_RES
<222> LOCATION: (61)..(61)
<223> OTHER INFORMATION: Asn or any amino acid
<220> FEATURE:
<221> NAME/KEY: MOD_RES
<222> LOCATION: (62)..(62)
<223> OTHER INFORMATION: Glu or any amino acid
<220> FEATURE:
<221> NAME/KEY: MOD_RES
<222> LOCATION: (63)..(63)
<223> OTHER INFORMATION: Lys or any amino acid
<220> FEATURE:
<221> NAME/KEY: MOD_RES
<222> LOCATION: (64)..(64)
<223> OTHER INFORMATION: Phe or any amino acid
<220> FEATURE:
<221> NAME/KEY: MOD_RES
<222> LOCATION: (65)..(65)
<223> OTHER INFORMATION: Lys or any amino acid
<220> FEATURE:
<221> NAME/KEY: MOD_RES
<222> LOCATION: (66)..(66)
<223> OTHER INFORMATION: Gly or any amino acid
<220> FEATURE:
<221> NAME/KEY: MOD_RES
<222> LOCATION: (67)..(67)
<223> OTHER INFORMATION: Lys or Arg
```

```
<220> FEATURE:
<221> NAME/KEY: MOD_RES
<222> LOCATION: (68)..(68)
<223> OTHER INFORMATION: Ala or Val
<220> FEATURE:
<221> NAME/KEY: MOD_RES
<222> LOCATION: (70)..(70)
<223> OTHER INFORMATION: Leu or Met
<220> FEATURE:
<221> NAME/KEY: MOD_RES
<222> LOCATION: (72)..(72)
<223> OTHER INFORMATION: Ala, Leu or Thr
<220> FEATURE:
<221> NAME/KEY: MOD_RES
<222> LOCATION: (76)..(76)
<223> OTHER INFORMATION: Ser or Thr
<220> FEATURE:
<221> NAME/KEY: MOD_RES
<222> LOCATION: (82)..(82)
<223> OTHER INFORMATION: Gln or Glu
<220> FEATURE:
<221> NAME/KEY: MOD_RES
<222> LOCATION: (85)..(85)
<223> OTHER INFORMATION: Ser or Arg
<220> FEATURE:
<221> NAME/KEY: MOD_RES
<222> LOCATION: (87)..(87)
<223> OTHER INFORMATION: Thr or Arg
<220> FEATURE:
<221> NAME/KEY: MOD_RES
<222> LOCATION: (91)..(91)
<223> OTHER INFORMATION: Ser or Thr
<220> FEATURE:
<221> NAME/KEY: MOD_RES
<222> LOCATION: (95)..(95)
<223> OTHER INFORMATION: Phe or Tyr
<220> FEATURE:
<221> NAME/KEY: MOD_RES
<222> LOCATION: (98)..(98)
<223> OTHER INFORMATION: Tyr, Lys or Arg
<220> FEATURE:
<221> NAME/KEY: MOD_RES
<222> LOCATION: (99)..(99)
<223> OTHER INFORMATION: Tyr or any amino acid
<220> FEATURE:
<221> NAME/KEY: MOD_RES
<222> LOCATION: (100)..(100)
<223> OTHER INFORMATION: Asp or any amino acid
<220> FEATURE:
<221> NAME/KEY: MOD_RES
<222> LOCATION: (101)..(102)
<223> OTHER INFORMATION: Ala or any amino acid
<220> FEATURE:
<221> NAME/KEY: MOD_RES
<222> LOCATION: (103)..(103)
<223> OTHER INFORMATION: Gly, Asn or any amino acid
<220> FEATURE:
<221> NAME/KEY: MOD_RES
<222> LOCATION: (104)..(104)
<223> OTHER INFORMATION: Pro, His or any amino acid
<220> FEATURE:
<221> NAME/KEY: MOD_RES
<222> LOCATION: (105)..(105)
<223> OTHER INFORMATION: Trp, Gly, Tyr or any amino acid
<220> FEATURE:
<221> NAME/KEY: MOD_RES
<222> LOCATION: (106)..(106)
<223> OTHER INFORMATION: Phe or any amino acid
<220> FEATURE:
<221> NAME/KEY: MOD_RES
<222> LOCATION: (107)..(107)
<223> OTHER INFORMATION: Ala, Asp or any amino acid
<220> FEATURE:
<221> NAME/KEY: MOD_RES
<222> LOCATION: (108)..(108)
<223> OTHER INFORMATION: Tyr or any amino acid
<220> FEATURE:
<221> NAME/KEY: MOD_RES
<222> LOCATION: (114)..(114)
```

```
<223> OTHER INFORMATION: Thr, Ser or Leu
<220> FEATURE:
<221> NAME/KEY: MOD_RES
<222> LOCATION: (115)..(115)
<223> OTHER INFORMATION: Val or Leu
<220> FEATURE:
<221> NAME/KEY: MOD_RES
<222> LOCATION: (119)..(119)
<223> OTHER INFORMATION: Ser or Ala

<400> SEQUENCE: 151

Xaa Val Xaa Leu Xaa Xaa Ser Gly Ala Glu Xaa Xaa Xaa Pro Gly Xaa
 1               5                  10                  15

Ser Val Lys Xaa Xaa Cys Lys Xaa Ser Gly Xaa Thr Xaa Thr Xaa Xaa
             20                  25                  30

Xaa Xaa Xaa Trp Val Xaa Gln Xaa Pro Gly Xaa Gly Leu Glu Xaa Xaa
         35                  40                  45

Gly Xaa Xaa Xaa Xaa Xaa Xaa Xaa Xaa Xaa Xaa Xaa Xaa Xaa Xaa Xaa
     50                  55                  60

Xaa Xaa Xaa Xaa Thr Xaa Thr Xaa Asp Thr Ser Xaa Ser Thr Ala Tyr
65                  70                  75                  80

Met Xaa Leu Ser Xaa Leu Xaa Ser Glu Asp Xaa Ala Val Tyr Xaa Cys
                 85                  90                  95

Ala Xaa Xaa Xaa Xaa Xaa Xaa Xaa Xaa Xaa Xaa Trp Gly Gln Gly
            100                 105                 110

Thr Xaa Xaa Thr Val Ser Xaa
        115

<210> SEQ ID NO 152
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ile, Val, or Leu
<220> FEATURE:
<221> NAME/KEY: MOD_RES
<222> LOCATION: (3)..(3)
<223> OTHER INFORMATION: Gln or Leu
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Leu or Pro
<220> FEATURE:
<221> NAME/KEY: MOD_RES
<222> LOCATION: (17)..(17)
<223> OTHER INFORMATION: Asp or Glu
<220> FEATURE:
<221> NAME/KEY: MOD_RES
<222> LOCATION: (18)..(18)
<223> OTHER INFORMATION: Gln or Pro
<220> FEATURE:
<221> NAME/KEY: MOD_RES
<222> LOCATION: (24)..(24)
<223> OTHER INFORMATION: Arg, Lys or any amino acid
<220> FEATURE:
<221> NAME/KEY: MOD_RES
<222> LOCATION: (25)..(26)
```

```
<223> OTHER INFORMATION: Ser or any amino acid
<220> FEATURE:
<221> NAME/KEY: MOD_RES
<222> LOCATION: (27)..(27)
<223> OTHER INFORMATION: Gln or any amino acid
<220> FEATURE:
<221> NAME/KEY: MOD_RES
<222> LOCATION: (28)..(28)
<223> OTHER INFORMATION: Ser or any amino acid
<220> FEATURE:
<221> NAME/KEY: MOD_RES
<222> LOCATION: (29)..(29)
<223> OTHER INFORMATION: Ile, Leu or any amino acid
<220> FEATURE:
<221> NAME/KEY: MOD_RES
<222> LOCATION: (30)..(30)
<223> OTHER INFORMATION: Val, Leu or any amino acid
<220> FEATURE:
<221> NAME/KEY: MOD_RES
<222> LOCATION: (31)..(31)
<223> OTHER INFORMATION: His or any amino acid
<220> FEATURE:
<221> NAME/KEY: MOD_RES
<222> LOCATION: (32)..(32)
<223> OTHER INFORMATION: Ser or any amino acid
<220> FEATURE:
<221> NAME/KEY: MOD_RES
<222> LOCATION: (33)..(33)
<223> OTHER INFORMATION: Asn, Asp or any amino acid
<220> FEATURE:
<221> NAME/KEY: MOD_RES
<222> LOCATION: (34)..(34)
<223> OTHER INFORMATION: Gly or any amino acid
<220> FEATURE:
<221> NAME/KEY: MOD_RES
<222> LOCATION: (35)..(35)
<223> OTHER INFORMATION: Asn, Lys or any amino acid
<220> FEATURE:
<221> NAME/KEY: MOD_RES
<222> LOCATION: (36)..(36)
<223> OTHER INFORMATION: Thr or any amino acid
<220> FEATURE:
<221> NAME/KEY: MOD_RES
<222> LOCATION: (37)..(37)
<223> OTHER INFORMATION: Tyr or any amino acid
<220> FEATURE:
<221> NAME/KEY: MOD_RES
<222> LOCATION: (38)..(38)
<223> OTHER INFORMATION: Leu or any amino acid
<220> FEATURE:
<221> NAME/KEY: MOD_RES
<222> LOCATION: (39)..(39)
<223> OTHER INFORMATION: Glu, His, Tyr or any amino acid
<220> FEATURE:
<221> NAME/KEY: MOD_RES
<222> LOCATION: (50)..(50)
<223> OTHER INFORMATION: Lys or Gln
<220> FEATURE:
<221> NAME/KEY: MOD_RES
<222> LOCATION: (53)..(53)
<223> OTHER INFORMATION: Ile or Val
<220> FEATURE:
<221> NAME/KEY: MOD_RES
<222> LOCATION: (55)..(55)
<223> OTHER INFORMATION: Lys, Glu or any amino acid
<220> FEATURE:
<221> NAME/KEY: MOD_RES
<222> LOCATION: (56)..(56)
<223> OTHER INFORMATION: Val or any amino acid
<220> FEATURE:
<221> NAME/KEY: MOD_RES
<222> LOCATION: (57)..(57)
<223> OTHER INFORMATION: Ser or any amino acid
<220> FEATURE:
<221> NAME/KEY: MOD_RES
<222> LOCATION: (58)..(58)
<223> OTHER INFORMATION: Asn, Ser or any amino acid
<220> FEATURE:
<221> NAME/KEY: MOD_RES
```

```
<222> LOCATION: (59)..(59)
<223> OTHER INFORMATION: Arg or any amino acid
<220> FEATURE:
<221> NAME/KEY: MOD_RES
<222> LOCATION: (60)..(60)
<223> OTHER INFORMATION: Phe or any amino acid
<220> FEATURE:
<221> NAME/KEY: MOD_RES
<222> LOCATION: (61)..(61)
<223> OTHER INFORMATION: Ser or any amino acid
<220> FEATURE:
<221> NAME/KEY: MOD_RES
<222> LOCATION: (88)..(88)
<223> OTHER INFORMATION: Leu or Val
<220> FEATURE:
<221> NAME/KEY: MOD_RES
<222> LOCATION: (94)..(94)
<223> OTHER INFORMATION: Phe, Ser or any amino acid
<220> FEATURE:
<221> NAME/KEY: MOD_RES
<222> LOCATION: (95)..(95)
<223> OTHER INFORMATION: Gln or any amino acid
<220> FEATURE:
<221> NAME/KEY: MOD_RES
<222> LOCATION: (96)..(96)
<223> OTHER INFORMATION: Gly, Ser or any amino acid
<220> FEATURE:
<221> NAME/KEY: MOD_RES
<222> LOCATION: (97)..(97)
<223> OTHER INFORMATION: Ser, Thr or any amino acid
<220> FEATURE:
<221> NAME/KEY: MOD_RES
<222> LOCATION: (98)..(98)
<223> OTHER INFORMATION: His or any amino acid
<220> FEATURE:
<221> NAME/KEY: MOD_RES
<222> LOCATION: (99)..(99)
<223> OTHER INFORMATION: Val or any amino acid
<220> FEATURE:
<221> NAME/KEY: MOD_RES
<222> LOCATION: (100)..(100)
<223> OTHER INFORMATION: Pro or any amino acid
<220> FEATURE:
<221> NAME/KEY: MOD_RES
<222> LOCATION: (101)..(101)
<223> OTHER INFORMATION: Tyr or any amino acid
<220> FEATURE:
<221> NAME/KEY: MOD_RES
<222> LOCATION: (102)..(102)
<223> OTHER INFORMATION: Thr or any amino acid
<220> FEATURE:
<221> NAME/KEY: MOD_RES
<222> LOCATION: (105)..(105)
<223> OTHER INFORMATION: Gly or Gln
<220> FEATURE:
<221> NAME/KEY: MOD_RES
<222> LOCATION: (111)..(111)
<223> OTHER INFORMATION: Ile or Leu

<400> SEQUENCE: 152

Asp Xaa Xaa Met Thr Gln Xaa Pro Leu Ser Leu Pro Val Xaa Xaa Gly
1               5                   10                  15

Xaa Xaa Ala Ser Ile Ser Cys Xaa Xaa Xaa Xaa Xaa Xaa Xaa Xaa Xaa
            20                  25                  30

Xaa Xaa Xaa Xaa Xaa Xaa Xaa Trp Tyr Leu Gln Lys Pro Gly Gln Ser
        35                  40                  45

Pro Xaa Leu Leu Xaa Tyr Xaa Xaa Xaa Xaa Xaa Xaa Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Xaa Xaa Xaa
                85                  90                  95
```

```
Xaa Xaa Xaa Xaa Xaa Xaa Phe Gly Xaa Gly Thr Lys Leu Glu Xaa Lys
            100                 105                 110
Arg Ala
```

TUMOR-SPECIFIC RECOGNITION MOLECULES

CROSS-REFERENCE TO RELATED APPLICATIONS

This application is a continuation of U.S. application Ser. No. 13/302,698, which has a filing date of Nov. 22, 2011, now allowed, which is a continuation of U.S. patent application Ser. No. 10/536,834, which has a filing date of Mar. 20, 2006, now issued on Jan. 3, 2012 as U.S. Pat. No. 8,088,357, and which is a national stage application filed under 35 U.S.C. §371 of International Patent Application No. PCT/DE2003/003994, accorded an international filing date of Dec. 1, 2003, which claims the benefit of priority to German (DE) Patent Application Serial No. 102 56 900.2, filed Nov. 29, 2002.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 400086_401C2_SEQUENCE_LISTING.txt. The text file is 145 KB, was created on Nov. 17, 2013, and is being submitted electronically via EFS-Web.

The invention relates to recognition molecules which are directed towards tumors and can be used in the diagnosis and therapy of tumor diseases.

Tumor diseases or cancerous diseases are oncotic diseases which can be described by a locally confined increase of tissue volume. In a broader sense, any localized swelling as a result of oedemas, acute and/or chronic inflammations, an aneurysmatic expansion or even organ swelling caused by inflammation is a tumor. More strictly speaking, especially formation of new tissue such as tumescence, blastomas and/or neoplasias in the form of a spontaneous, variably disinhibited, autonomous and irreversible excessive growth of autologous tissue, normally associated with more or less distinct loss of specific cells and tissue functions, is understood to be a tumor disease. Tumors can be systematized according to their biological behavior, but also into a histogenetic taxonomy, or according to clinical or pathological findings.

Specifically in the clinical sector it may be necessary to recognize tumors as early as possible and in a selective fashion as well, because early recognition and the treatment or removal that follows will ensure successful treatment of the swelling without deformation of the affected organ structures or gene sections, thereby also preventing formation of metastases. In subsequent examinations following a cancer treatment even slightest metastases must also be detected at an early stage in order to optimize further aftercare. In many sectors of occupational medicine and health care it is also necessary to determine whether a tissue or an organ has potential susceptibility to cancer before the organ or tissue has already undergone degeneration or transformation.

The oldest and—at the same time—simplest method of tumor recognition sometimes used successfully even today is palpation and visual observation. Thus, for example, mammary carcinomas or prostate carcinomas are palpable as nodes. Indications of skin cancer as a result of conspicuous birthmarks can be detected optically by physicians or patients themselves. Other optical procedures are imaging methods, for example, wherein images of the body are recorded by means of apparatus, in which images a tumor can be recognized. These methods include e.g., X-ray irradiation, as well as computer tomography (CT). In these procedures the body is screened with high-energy radiation, and the degenerate tissue structures can be recognized as a result of the transparency change for such radiation compared to healthy tissue. Frequently, contrast media are used in such methods, which are injected into the corresponding regions, increasing the absorption. In addition, cancer diagnosis is possible by means of ultrasound or by using radiolabeled antibodies, in which case the tumor-typical antigens will bind to the organs to be examined, so that the tumors can be recognized in the imaging procedure. In addition to imaging methods, laboratory investigations are another important means of early detection of cancer, where samples of urine, blood or tissue are examined for abnormal features. For example, this might be an altered composition of such samples, but also, appearance of substances normally not occurring or only in small quantities. These substances are generally referred to as tumor markers. They are either produced by the tumor tissue itself or formed as a body response to the tumor. In addition to substances, cellular changes whose qualitative or quantitative analysis allows a statement as to the presence, course or prognosis of malignant diseases are also referred to as tumor markers. Most tumor markers are physiologically occurring or modified substances which can be detected in urine, serum or other body fluids at higher or lower concentrations compared to physiological conditions or normal genotypical/phenotypical expression, or in or on tumor cells, said substances being synthesized and/or secreted by the tumor tissue and subsequently liberated by tumor decay or formed in response of the organism to a tumor. A wide variety of tumor markers has been described, the use of which is considered reasonable especially in colon cancer, breast cancer, ovary cancer, prostate and testicle cancers and in small-cell lung carcinoma. Such cancer markers include e.g., CEA, CA 15-3, CA 125, α-fetoprotein, HCG, prostate-specific antigen, neuron-specific enolase, CA 19-9 and SCC.

By an increase in serum or in tissues or by their presence as modified proteins, lipids and/or carbohydrates, the above-mentioned markers, on the one hand, indicate e.g., (i) inflammatory diseases, intestinal polyps, viral inflammations and, on the other hand, especially (ii) cirrhoses, degenerations, tumors and metastases. A major part of these markers consists of molecules comprising both protein and carbohydrate structures, and possibly lipids. The lower the protein level and thus, the higher the carbohydrate or lipid level of these markers, the more difficult is detection thereof using e.g., recognition molecules such as antibodies. Up to now, various antibodies to carbohydrate structures have been produced by immunization of mice using the hybridoma technology.

Cancer diagnostics using recognition molecules involves several disadvantages. Thus, certain tumor markers may also be present in non-cancerogenic diseases, so that the recognition molecules employed indicate a positive reaction. Furthermore, non-interaction of recognition molecules does not indicate the absence of a tumor disease. Another drawback is that well-known recognition substances are normally non-specific. That is, positive detection rarely indicates a specific type of tumor disease. In addition, another and crucial drawback of well-known recognition molecules is their limited usability in monitoring the development of tumors, e.g., subsequent to surgery. As a rule, the use of well-known tumor markers therefore is not possible in early recognition or in aftercare, especially in prophylaxis.

In addition to the above general disadvantages, there are some specific drawbacks in recognition molecules directed towards carbohydrate structures. Immunization with carbohydrate antigens usually results in a primary IgM response only, or immune response is completely absent because many carbohydrate structures are also autoantigens. Carbohydrates are T cell-independent antigens incapable of inducing class switching and associated maturing by somatic mutations, which is why the antibody response is usually restricted to the IgM class. Therefore, due to the generally weak interaction and necessary multivalence, it is difficult to produce high-affinity antibodies. One problem with antibodies to carbohydrate structures not only is low affinity, but also the specificity. In particular, production of specific antibodies to short uncharged carbohydrate structures is extremely difficult, and in many cases a certain specificity is only achieved when the carbohydrate structure is localized on a specific carrier. Thus, for example, the JAA/F11 antibody which is directed towards Galβ1→3GalNAc not only recognizes this antigen, but also GlcNAcβ1→6Galβ1→3(GlcNAcβ1→6)GalNAc and—although with lower avidity—Galβ1-3GlcNAc. More recent ways of obtaining recognition molecules using various forms of combined techniques, such as phage display technology, neither solve the above-mentioned disadvantages. The problem of weak recognition molecule-carbohydrate interaction remains in this latter case as well. In this context, particular attention should be given to the fact that the primary IgM antibodies which are the most frequent ones obtained by immunization are too large in size for therapeutic use. Another disadvantage of well-known recognition molecules for tumor markers is that they do not make the tumor recognizable until it has already reached a critical size. That is to say, early stages of tumor growth cannot be determined with well-known recognition molecules directed towards tumor markers.

Another drawback of well-known recognition substances is that "functional" use thereof is not possible. "Functional" means that the recognition molecules bind to the tumor markers not only in such a way that the latter are detected, but that they interact with the tumor cell via markers in such a way that the tumor cell is impaired in its growth. Such recognition molecules may specifically interact with particular tumor markers, which are immobilized e.g., on the surface of tumor cells, in such a way that the tumor characterized by the tumor markers is given a therapeutic treatment. On the one hand, these functionally active recognition molecules are capable of detecting tumor cell-associated tumor markers and, at the same time, prevent the tumor cell from further growth or formation of metastases as a result of binding to this tumor-specific structure. Disadvantageously, well-known recognition molecules are capable of affecting tumor growth only in rare cases. As a rule, additional substances restricting or inhibiting tumor growth therefore must be coupled to the antibody, so that the latter represents the "shuttle" of said substance rather than the agent of treatment.

The object of the invention is therefore to provide recognition molecules which, on the one hand, allow easy, reliable and efficient detection of tumors and, in addition, can be used in the prophylaxis, therapy and/or aftercare of tumors.

The invention solves the above technical problem by providing recognition molecules comprising an amino acid sequence which contains the amino acid sequence SEQ ID No. 1 and the amino acid sequence SEQ ID No. 2 or 3 and the amino acid sequences SEQ ID No. 4, 5 or 6, said recognition molecules specifically binding the core 1 antigen.

Mutatis mutandis, the definitions of terms given below also apply to statements given above, those given here and hereinafter.

According to the invention, the term recognition molecule is understood to concern a molecule which, especially under stringent conditions, specifically binds the core 1 carbohydrate structure.

According to the invention, core 1 is understood to be the carbohydrate structure Galβ1-3GalNAc which can be present as α-anomer (Galβ1-3GalNAcα) or β-anomer (Galβ1-3GalNAcβ). Preferred in this context is the α-anomeric variant. However, the recognition molecules according to the invention can also bind the α-anomer Galβ1-3GalNAcα alone or both anomers Galβ1-3GalNAcα and Galβ1-3GalNAcβ in the same way.

According to the invention, specific binding towards core 1 is understood to be binding that recognizes core 1 only, preferably the α-anomer, or recognizes core 1 and core 2 (Galβ1-3(GlcNAcβ1-6)GalNAcα). The recognition molecules do not exhibit any cross-reactivity with other derivatives and anomers of carbohydrate structures such as given in Example 7. The recognition molecules of the invention do not interact with Galα1-3GalNAcα, Galα1-3GalNAcβ, GalNAcα, Neu5Acα2-3Galβ1-3GalNAcα, Galβ1-3(Neu5Acα2-6)GalNAcα, GlcNAcβ1-2Galβ1-3GalNAcα, GlcNAcα1-3Galβ1-3GalNAcα, GalNAcα1-3Galβ and 3'-O-Su-Galβ1-3GalNAcα under the conditions described in Example 7. In particular, determination is effected by means of specificity tests using well-defined synthetic carbohydrate structures.

In a preferred embodiment a recognition molecule of the invention specifically binding the core 1 antigen comprises:

a) a first amino acid sequence which contains the amino acid sequence SEQ ID No. 1 and the amino acid sequence SEQ ID No. 2 or 3 and the amino acid sequence SEQ ID No. 4 or 5 or 6; and b) a second amino acid sequence which contains the amino acid sequence SEQ ID No. 7 or 8 or 9 and the amino acid sequence SEQ ID No. 10 or 11 and the amino acid sequence SEQ ID No. 12 or 13.

The first and the second amino acid sequence can be present on one or more and preferably two polypeptides.

The core 1-binding recognition molecules according to the invention are characterized in that a defined set of single amino acid sequences is included therein. The amino acid sequence of said recognition molecules includes one or two triplets of defined sequences. These sequences represent the binding domains and define the specificity of the recognition molecules. The 1-triplet recognition molecule contains the amino acid sequence SEQ ID NO. 1, the amino acid sequence SEQ ID NO. 2 or 3 and the amino acid sequence SEQ ID NO. 4 or 5 or 6. Core 1-specific recognition molecules defined by two triplets contain the amino acid sequence SEQ ID NO. 1, the amino acid sequence SEQ ID NO. 2 or 3 and the amino acid sequence SEQ ID NO. 4 or 5 or 6 for the first triplet, and the amino acid sequence SEQ ID NO. 7 or 8 or 9, the amino acid sequence SEQ ID NO. 10 or 11 and the amino acid sequence SEQ ID NO. 12 or 13 for the second triplet. The first and the second triplet can be present either on one or on more polypeptide chains which, in the latter case, together form the binding recognition molecule. Further, in the meaning of the invention, these triplets are referred to as triplet sequence 1 for the first amino acid sequence being included and as triplet sequence 2 for the second amino acid sequence being included; see definition a) and b) of the description above. According to the invention, the recognition molecule can be an antibody, particularly a murine, chimeric or human IgG or IgM, an scFv structure or other.

Another embodiment of the invention relates to recognition molecules wherein at least one amino acid sequence of SEQ ID Nos. 1 to 13 has been modified by mutation, deletion and/or insertion, but wherein the property of binding specificity towards core 1 continues to exist. Advantageously, this is utilized to improve the recognition molecules, e.g., with respect to affinity, solubility and/or producibility.

In a preferred embodiment, modification of a recognition molecule is effected by one or more mutations in one or more amino acid sequences selected from SEQ ID Nos. 1 to 13, wherein single amino acids are replaced by amino acids having analogous physicochemical properties which, advantageously, do not fundamentally change the three-dimensional structure of the binding domain in the recognition molecules, so that the core 1 specificity of the recognition molecules is retained. Amino acids having analogous physicochemical properties in the meaning of the invention can be summarized into 6 separate groups and are illustrated in Table 1.

TABLE 1

Amino acids with analogous physicochemical properties regardless of molecular size

| Property or functional group | Amino acid |
| --- | --- |
| aliphatic | glycine |
|  | alanine |
|  | valine |
|  | leucine |
|  | isoleucine |
| hydroxy group | serine |
|  | threonine |
| carboxyl group | aspartic acid |
|  | glutamic acid |
| amide group | asparagine |
|  | glutamine |
| amino group | lysine |
|  | arginine |
| aromatic | phenylalanine |
|  | tyrosine |
|  | tryptophan |

In another preferred embodiment of the recognition molecules of the invention specifically binding core 1, at least one amino acid sequence of amino acid sequences SEQ ID Nos. 1, 2, 3, 7, 8 and/or 9 is replaced by canonical structure variants or equivalent structures having the amino acid sequences SEQ ID Nos. 14 to 45, with SEQ ID NO. 1 being replaced by a sequence of sequences SEQ ID Nos. 14 to 17 (CDRH1), SEQ ID NO. 2 or 3 by a sequence of sequences SEQ ID Nos. 18 to 27 (CDRH2), and SEQ ID NO. 7 or 8 or 9 by a sequence of sequences SEQ ID Nos. 28 to 45 (CDRL1).

The general relationship between an amino acid sequence and the tertiary structure of loops formed by these sequences is well-known to those skilled in the art and has been investigated in detail [Rooman et al., 1989; Martin, Thornton, 1996].

Immunoglobulins represent a unique example. By analyzing the loop conformations of the hypervariable regions (complementarity determining regions, CDRs) in the light and heavy chains of antibody molecules, so-called canonical classes have been defined [Chothia, Lesk, 1987; Chothia et al., 1986, 1989, 1992; Wu, Cygler, 1993]. On this basis, the canonical structure variants SEQ ID Nos. 14 to 45 of SEQ ID Nos. of 1, 2, 3, 7, 8 and 9 have been derived.

The amino acid sequences SEQ ID Nos. 1 to 13 or their modifications in a core 1-specific recognition molecule in the meaning of the invention form spatial structures, e.g., so-called loops which are characterized by possessing a definable tertiary structure and/or quaternary structure. The binding region of a recognition molecule with the core 1 antigen is formed by amino acid residues which are provided by up to six variable loops on the surface of the molecule and specifically interact with core 1.

In another embodiment of the invention, recognition molecules specifically binding core 1 are provided, wherein at least one sequence of the triplet sequences is omitted, which is not immediately involved in the interaction with the core 1 antigen.

In another embodiment the recognition molecules comprise at least one of the amino acid sequences SEQ ID Nos. 1 to 13 or the above-described variants thereof in duplicate or multiplicity, and such doubles may also be present in the form of variants of the same amino acid sequence. All recognition molecules described in this section advantageously recognize the core 1 antigen in a specific manner. For easier comprehension, the above recognition molecules as well, which, strictly speaking, do not bear any triplet sequences as a result of omitting or multiplying sequences, will nevertheless be referred to as triplet sequence 1 or triplet sequence 2 hereinafter.

In another embodiment the recognition molecules of the invention specifically binding the core 1 antigen comprise amino acid sequences having a homology of at least 60%, preferably 70%, more preferably 80%, especially preferably 90%, with respect to the sequences SEQ ID Nos. 1 to 13.

Furthermore, the recognition molecules in the meaning of the invention may comprise framework sequences which separate the comprising amino acid sequences, i.e., amino acid sequence SEQ ID NO. 1 and amino acid sequence SEQ ID NO. 2 or 3 and amino acid sequence SEQ ID No. 4 or 5 or 6, or the above-described variants thereof, and framework sequences which separate the amino acid sequence SEQ ID No. 7 or 8 or 9 and the amino acid sequence SEQ ID No. 10 or 11 and the amino acid sequence SEQ ID No. 12 or 13, or the above-described variants thereof. The first and the second amino acid sequence can be present on one or more and preferably two polypeptide chains. In the meaning of the invention, such framework sequences are also referred to as spacers and may vary in length and sequence. This expressly includes those recognition molecules wherein not all of the amino acid sequences SEQ ID Nos. 1 to 13 or the above-described variants thereof are separated by spacers. Moreover, the recognition molecules preferably have additional flanking amino acid sequences likewise referred to as framework sequences in the meaning of the invention.

More specifically, the framework sequences have the function of forming the above-described amino acid sequences responsible for or involved in core 1-specific binding of the recognition molecules into a suitable configuration and spatial structure so as to allow binding to core 1. It can be envisaged that the amino acid sequences SEQ ID NO. 1 to NO. 13 without at least one additional amino acid sequence as framework sequence are incapable of binding the core 1 antigen in a specific fashion in the meaning of the invention. Moreover, the framework sequences may provide the recognition molecules with e.g., the required biological and chemical stability, so that the spatial structure can be built up effectively and maintained for function and use in a suitable functional form which includes core 1 binding.

In a preferred embodiment the triplet sequences are introduced in existing proteins by replacement of amino acid sequences and/or by addition, the existing protein sequences serving as framework sequences in the meaning of the invention, or framework sequences being taken from suitable proteins. For example, such framework sequences can be modified by means of mutations, deletions or insertions. Methods of molecular biology, biochemistry and protein engineering per se known to those skilled in the art can be employed for this purpose. Preferred proteins for this purpose are proteins of the immunoglobulin superfamily, protease inhibitors, lectins, helix bundle proteins and lipocalins, such as disclosed in: Nygren and Uhlen, 1997; Nuttall S D et al., 1999; and Skerra, 2000.

In another preferred embodiment the framework sequences are antibody framework sequences from one or various species or amino acid sequences mimicking the consensus sequence of framework sequences of murine, human antibodies and/or antibodies of other mammals. A consensus sequence is an idealized sequence wherein the most frequently occurring amino acid is representative in each position when comparing a large number of existing sequences, e.g., from antibody data bases. The recognition molecules preferred herein are characterized in that the framework sequences for the first triplet sequence 1 comprising the amino acid sequence SEQ ID NO. 1, the amino acid sequence SEQ ID NO. 2 or 3 and the amino acid sequence SEQ ID NO. 4 or 5 or 6, or the above-described variants, are antibody framework sequences of the variable heavy chain, $V_H$, in the literature also referred to as framework sequences, and the framework sequences for the triplet sequence 2 comprising the amino acid sequence SEQ ID NO. 7 or 8 or 9, the amino acid sequence SEQ ID NO. 10 or 11 and the amino acid sequence SEQ ID NO. 12 or 13, or the above-described variants thereof, are antibody framework sequences of the variable light chain, $V_L$.

Also preferred are antibody framework sequences of antibodies from mammals, with antibody framework sequences of human and/or murine origin being particularly preferred. The framework sequences can be combined from antibody framework sequences of various species. Such antibody framework sequences are well-known to those skilled in the art and can be obtained from various data bases such as the Kabat data base (immuno.bme.nwu.edu) or the National Center for Biotechnology Information data base (ncbi.nlm.nih.gov). Likewise, these antibody framework structures can be extended by additional amino acids and/or modified by one or more mutations, e.g., deletions and/or insertions, with specific binding to core 1 being retained.

When combining the triplet sequences with antibody framework sequences in a preferred variant of the invention, the recognition molecule represents a variable chain of an antibody or a structure derived therefrom.

Particularly preferred antibody framework sequences as framework sequences in the meaning of the invention are the amino acid sequences corresponding to FRH1, FRH2, FRH3 and FHR4 in Table 2 for the variable heavy chain and the amino acid sequences corresponding to FRL1, FRL2, FRL3 and FRL4 in Table 2 for the variable light chain, the amino acid sequences of the triplet sequences 1 and 2 with SEQ ID Nos. 1 to 13 corresponding to the corresponding CDR regions of the antibodies. The variable heavy ($V_H$) and light ($V_L$) antibody chains, respectively, are composed as follows: $V_H$: FRH1-CDRH1-FRH2-CDRH2-FRH3-CDRH3-FRH4, and $V_L$: FRL1-CDRL1-FRL2-CDRL2-FRL3-CDRL3-FRL4. Table 2 illustrates the positions in detail. The positions of the individual amino acids or amino acid sequences correspond to the numbering of amino acids in antibody molecules according to Kabat.

TABLE 2

(FRH1-4 disclosed as SEQ ID NO: 151 and FRL1-4 disclosed as SEQ ID NO: 152)

| Name | Position range | Pos. | Amino acid or amino acid sequence |
|---|---|---|---|
| FRH1 | 1 to 30 (SEQ ID NO: 143) | 1 | Q or E |
| | | 2 | V |
| | | 3 | Q, K or T |
| | | 4 | L |
| | | 5 | K or V |
| | | 6 | E or Q |
| | | 7 | S |
| | | 8 | G |
| | | 9 | A |
| | | 10 | E |
| | | 11 | L or V |
| | | 12 | V or K |
| | | 13 | R or K |
| | | 14 | P |
| | | 15 | G |
| | | 16 | T or A |
| | | 17 | S |
| | | 18 | V |
| | | 19 | K |
| | | 20 | I or V |
| | | 21 | S or P |
| | | 22 | C |
| | | 23 | K |
| | | 24 | A, V, S or T |
| | | 25 | S |
| | | 26 | G |
| | | 27 | Y, F, S or D |
| | | 28 | T |
| | | 29 | F, L or I |
| | | 30 | T |
| CDRH1 | 31 to 35 | | SEQ ID NO. 1 and variants |
| FRH2 | 36 to 49 (SEQ ID NO: 144) | 36 | W |
| | | 37 | V |
| | | 38 | K or R |
| | | 39 | Q |
| | | 40 | R or A |
| | | 41 | P |
| | | 42 | G |
| | | 43 | H or Q |
| | | 44 | G |
| | | 45 | L |
| | | 46 | E |
| | | 47 | W or R |
| | | 48 | I or M |
| | | 49 | G |
| CDRH2 | 50 to 65, with position 52a introduced in addition | | SEQ ID NO. 2 or 3 and variants |
| FRH3 | 66 to 94 (SEQ ID NO: 145) | 66 | K or R |
| | | 67 | A or V |
| | | 68 | T |
| | | 69 | L or M |
| | | 70 | T |
| | | 71 | A, L or T |
| | | 72 | D |
| | | 73 | T |
| | | 74 | S |
| | | 75 | S or T |
| | | 76 | S |
| | | 77 | T |
| | | 78 | A |
| | | 79 | Y |
| | | 80 | M |
| | | 81 | Q or E |
| | | 82 | L |
| | | 82a | S |
| | | 82b | S or R |
| | | 82c | L |
| | | 83 | T or R |
| | | 84 | S |
| | | 85 | E |
| | | 86 | D |
| | | 87 | S or T |
| | | 88 | A |

TABLE 2-continued (FRH1-4 disclosed as SEQ ID NO: 151 and
FRL1-4 disclosed as SEQ ID NO: 152)

| Name | Position range | Pos. | Amino acid or amino acid sequence |
|---|---|---|---|
| | | 89 | V |
| | | 90 | Y |
| | | 91 | F or Y |
| | | 92 | C |
| | | 93 | A |
| | | 94 | Y, K or R |
| CDRH3 | 95 to 102, with positions 100a and 100b introduced in addition | | SEQ ID NO. 4, 5 or 6 and variants |
| FRH4 | 103 to 113 (SEQ ID NO: 146) | 103 | W |
| | | 104 | G |
| | | 105 | Q |
| | | 106 | G |
| | | 107 | T |
| | | 108 | T, S or L |
| | | 109 | V or L |
| | | 110 | T |
| | | 111 | V |
| | | 112 | S |
| | | 113 | S or A |
| FRL1 | 1 to 23 (SEQ ID NO: 147) | 1 | D |
| | | 2 | I, V or L |
| | | 3 | Q or L |
| | | 4 | M |
| | | 5 | T |
| | | 6 | Q |
| | | 7 | T or S |
| | | 8 | P |
| | | 9 | L |
| | | 10 | S |
| | | 11 | L |
| | | 12 | P |
| | | 13 | V |
| | | 14 | S or T |
| | | 15 | L or P |
| | | 16 | G |
| | | 17 | D or E |
| | | 18 | Q or P |
| | | 19 | A |
| | | 20 | S |
| | | 21 | I |
| | | 22 | S |
| | | 23 | C |
| CDRL1 | 22 to 34, with positions 27a, 27b, 27c, 27d and 27e introduced in addition | | SEQ ID NO. 7, 8 or 9 and variants |
| FRL2 | 35 to 49 (SEQ ID NO: 148) | 35 | W |
| | | 36 | Y |
| | | 37 | L |
| | | 38 | Q |
| | | 39 | K |
| | | 40 | P |
| | | 41 | G |
| | | 42 | Q |
| | | 43 | S |
| | | 44 | P |
| | | 45 | K or Q |
| | | 46 | L |
| | | 47 | L |
| | | 48 | I or V |
| | | 49 | Y |
| CDRL2 | 50 to 56 | | SEQ ID NO. 10 or 11 and variants |
| FRL3 | 57 to 88 (SEQ ID NO: 149) | 57 | G |
| | | 58 | V |
| | | 59 | P |
| | | 60 | D |
| | | 61 | R |
| | | 62 | F |
| | | 63 | S |
| | | 64 | G |
| | | 65 | S |
| | | 66 | G |
| | | 67 | S |
| | | 68 | G |
| | | 69 | T |
| | | 70 | D |
| | | 71 | F |
| | | 72 | T |
| | | 73 | L |
| | | 74 | K |
| | | 75 | I |
| | | 76 | S |
| | | 77 | R |
| | | 78 | V |
| | | 79 | E |
| | | 80 | A |
| | | 81 | E |
| | | 82 | D |
| | | 83 | L or V |
| | | 84 | G |
| | | 85 | V |
| | | 86 | Y |
| | | 87 | Y |
| | | 88 | C |
| CDRL3 | 89 to 97 | | SEQ ID NO. 12 or 13 and variants |
| FRL4 | 98 to 108 (SEQ ID NO: 150) | 98 | F |
| | | 99 | G |
| | | 100 | G or Q |
| | | 101 | G |
| | | 102 | T |
| | | 103 | K |
| | | 104 | L |
| | | 105 | E |
| | | 106 | I or L |
| | | 106a | K |
| | | 107 | R |
| | | 108 | A |

The amino acid sequences SEQ ID Nos. 46 to 79 correspond to amino acid sequences with preferred framework sequences for the variable heavy chain. The amino acid sequences SEQ ID Nos. 80 to 94 correspond to amino acid sequences with preferred framework sequences for the variable light chain.

The techniques and methods to be used in the production of these sequences are well-known to those skilled in the art, and a person skilled in the art will be able to select suitable framework sequences and/or mutations.

In the meaning of the invention, core 1-specific recognition molecules can be present in different formats. The basic structure of the recognition molecule is one (or more) polypeptide chain(s) comprising the above-described inventive triplet sequence 1 or triplet sequences 1 and 2 and framework sequences. For example, the amino acid sequence of the variable heavy chain is linked with the framework sequences and triplet sequences 1 and the amino acid sequence of the variable light chain is linked with the framework sequences and the triplet sequences 2 in a non-covalent or covalent fashion and can be situated on one or more polypeptide chains. A plurality of polypeptide chains can be present in covalently linked—e.g., via disulfide bridges—or non-covalently linked form as recognition molecule.

In particular, the various inventive formats of recognition molecules include linking of said triplet sequences with amino acid sequences beyond the framework sequences described above. In a preferred variant the recognition molecules according to the invention comprise further accessory sequences apart from the triplet sequences and framework sequences. More specifically, accessory sequences are amino acid sequences which primarily are not involved in the spatial configuration of the triplet sequences, such as in the form of framework sequences, but may have an advantageous influence thereon as a result of secondary or tertiary interactions. For example, accessory sequences in the form of constant domains of an antibody will stabilize the antibody, causing dimerization, thereby effecting improved binding of the antibody, or, for instance, fusion of an scFv with a domain of a bacteriophage coat protein causes an activity increase of scFv binding as disclosed in Jensen K B et al., 2002, for example.

Figure 3:
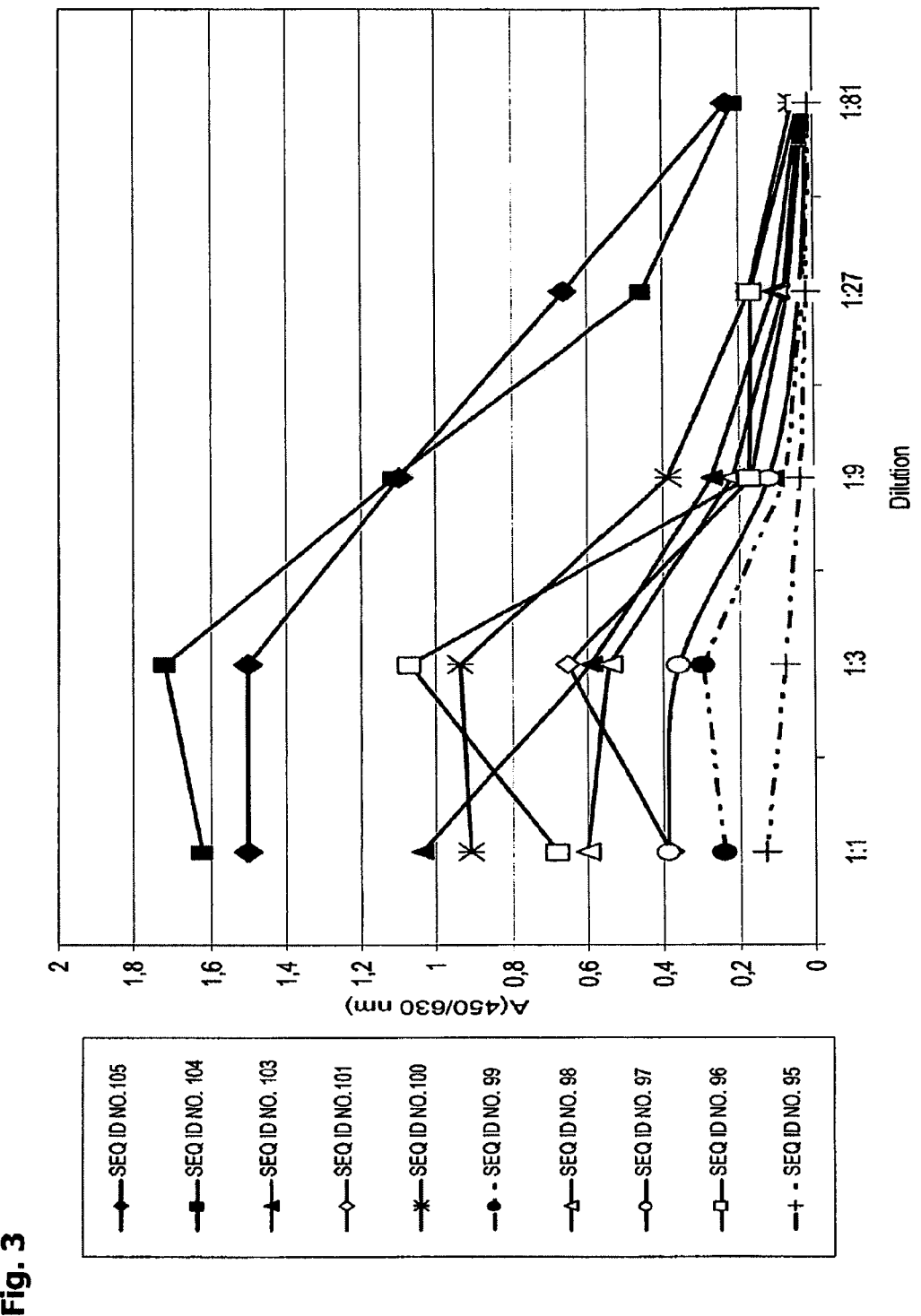

In a preferred embodiment the recognition molecules comprise amino acid sequences with framework sequences on an antibody basis and further accessory sequences in addition to the triplet sequences. In particular, the accessory sequences assume at least one of the following functions:

a) linking a triplet sequence with its correspondingly suited framework sequences with at least one other triplet sequence with its correspondingly suited framework sequences in order to create or improve binding capability;

b) stabilization of domains, e.g., by means of a linker between two protein domains or amino acid sequences, which undergo interaction with others in the same or in a second chain;

c) effector functions for immunological purposes, e.g., by fusion with the Fc portion of antibodies, chemokines, cytokines, growth factors or parts thereof, or antibodies having a different specificity, or fragments thereof, for the recruitment of cells of the immune system, e.g., macrophages or parts of the complement system;

d) fusion with tags, e.g., multimerization sequences—for example, μ-tail sequence from IgM or association domain from p53 or MBL—for multimerization of the core 1-binding portions for multivalent binding or for purification of recognition molecules, e.g., His-tag, or for detection, e.g., myc-tag, or for labeling or chelating of recognition molecules e.g., by high-lysine sequences.

Suitable structures are well-known to those skilled in the art or can be derived from the prior art by logical deduction.

Further preferred embodiments are recognition molecules according to the invention comprising the following formats: single-chain antibody fragment (scFv), Fv fragment, Fab fragment, $F(ab)_2$ fragment, multibody (dia-, tria-, tetrabody), immunoglobulin of the IgG, IgM, IgA, IgE, IgD isotypes or subclasses thereof, e.g., IgG1, or immunoglobulin-derived recognition molecules comprising at least one constant domain.

In a preferred embodiment the recognition molecules of the invention are composed of a heavy and a light polypeptide chain, each of the amino acid sequences of the heavy and light chains comprising one of the above-described triplet structures representing the CDR regions of the antibody, the corresponding antibody framework sequences representing the framework sequences of the antibody, and accessory sequences comprising at least one of the constant domains of the antibody isotype. The two chains can form covalent bonds with each other. The constant regions and variable regions may include sequences of antibodies from one or more species. Portions of constant domains or complete constant domains can be deleted or mutated in order to e.g., modify the effector function of accessory sequences, e.g., to prevent or improve binding to Fc receptors. In a preferred embodiment the recognition molecule is a murine, chimerized, humanized or human antibody or antibody fragment. For example, chimerization is effected by linking the variable antibody domains with constant antibody domains or fragments of a constant domain of antibodies from different species. Preferred are sequences of constant domains of human antibodies.

The antibody framework sequences can be selected in such a way that the sequences are largely homologous to human antibody sequences. Selection as to the species origin of the framework sequences will also depend on the use. Thus, for therapeutic use in particular fields, highest possible levels of human framework sequences are preferred, particularly in those cases where human anti-mouse antibody response (HAMA) is to be avoided. In other therapeutic fields, a xeno-portion is advantageous because it effects additional stimulation of the immune system. A combination of both is particularly suitable in some cases, especially in those cases where a xeno-portion is advantageous in initial immunization and a species-compatible, i.e., a human portion, is advantageous in later uses.

Homology to human consensus sequences is preferred, with HuHI being preferred for the variable heavy chain, and HuKII being preferred for the variable light chain. Particularly preferred is homology to human germ line sequences which are known to those skilled in the art and can be obtained from the V BASE data base (mrc-cpe.cam.ac.uk), for example.

The techniques and methods to be used in the production of these sequences are well-known to those skilled in the art, and a person skilled in the art will also be able to select suitable human sequences and/or perform optionally required mutations of said sequences.

In another embodiment the triplet sequences generally corresponding to the binding loops (CDR regions) and preferably having high homologies to the corresponding sequence regions in the human germ line sequence are additionally adapted thereto step by step, using simple mutations, without impairing the specific binding to core 1. Recognition molecules having these sequences will be referred to as partially human antibodies or antibody fragments herein. For example, preferred humanized sequences are represented by the sequences SEQ ID Nos. 56 to 79 and SEQ ID Nos. 85 to 94, respectively.

In another preferred embodiment, specific amino acids of antibody framework sequences of a species are replaced by others in order to generate less immunogenic regions in general. This involves technologies per se known to those skilled in the art, e.g., technologies of humanization, e.g., CDR grafting, resurfacing, chain shuffling with mutations and deimmunization by mutation or deletion of human MHC epitopes.

In a preferred embodiment, this involves an IgM-derived recognition molecule having the corresponding constant domains of an IgM, preferably human sequences. In the meaning of the invention, immunoglobulins are composed of a heavy chain and a light chain of an antibody, and 2 light chains and 2 heavy chains preferably represent a unit. Immunoglobulins of the IgM type usually consist of 5 such units additionally linked via the J chain to form disulfide bridges.

In a particularly preferred embodiment the J chain is absent, with multimerization of the subunits likewise taking place, in which case hexa- and pentameric structures can be present.

In a preferred embodiment of such recognition molecules, single-chain antibody fragments are involved, comprising a triplet structure 1 with the corresponding antibody framework sequences described above, which represent the CDR regions of the antibody and framework sequences of the variable domain of the heavy chain of antibodies, and a triplet structure 2 with the corresponding antibody framework sequences described above, which represent the CDR regions of the antibody and framework sequences of the variable domain of the light chain of antibodies, which are covalently linked in the form of a fusion protein. Here, the sequences are linked directly or via a linker. Preferred in this case are scFv formats with no linker or with a linker 1 to 9 amino acids in length. The scFv antibodies form multimeric structures (for example, dia-, tria-, tetrabodies) which, in the meaning of the invention, are also referred to as multibodies and exhibit higher avidity to the core 1 antigen as a result of multivalence. Core 1-specific recognition molecules in an scFv format were constructed with varying linker lengths (SEQ ID Nos. 95 to 106) and their binding characteristics investigated in an ELISA. Step-by-step linker length reduction resulted in an increase of binding to asialoglycophorin, which is a core 1-bearing glycoprotein, as illustrated in FIG. 3. The variants having SEQ ID Nos. 104 and 105 exhibited the best binding properties. These multivalent constructs in a dia-/triabody format are particularly preferred embodiments of the invention, being advantageous in tumor therapy as a result of improved pharmacokinetic properties.

In another preferred embodiment the recognition molecules are fused, chemically coupled, covalently or non-covalently associated with (i) immunoglobulin domains of various species, (ii) enzyme molecules, (iii) interaction domains, (iv) signal sequences, (v) fluorescent dyes, (vi) toxins, (vii) catalytic antibodies, (viii) one or more antibodies or antibody fragments with different specificity, (ix) cytolytic components, (x) immunomodulators, (xi) immunoeffectors, (xii) MHC class I or class II antigens, (xiii) chelating agents for radioactive labeling, (xiv) radioisotopes, (xv) liposomes, (xvi) transmembrane domains, (xvii) viruses and/or cells. In particular, the recognition molecules can also be fused with a tag allowing detection of the recognition molecule and purification thereof, such as myc-tag or His-tag. Technologies for the production of these constructs are well-known to those skilled in the art, and a person skilled in the art will be able to select suitable sequences and components and link them with the recognition molecules of the invention in a suitable manner.

In another preferred embodiment the above-described recognition molecules based on antibodies or antibody fragments are fused with peptides or proteins not derived from immunoglobulins. For example, the multimerization domain of a non-immunoglobulin molecule is fused with an scFv, especially the C-terminal end of the α-chain of the C4 binding protein, as described in Tonye Libyh M. et al., 1997, thereby constructing a multivalent recognition molecule.

In another embodiment, an scFv is fused with a transmembrane domain of a non-immunoglobulin molecule, e.g., with the transmembrane domain of c-erb B2, h-PDGFR, human transferrin receptor, or human asialoglycoprotein receptor (Liao et al., 2000), thereby enabling expression of binding molecules on the surface of cells.

Another preferred embodiment of the invention comprises recognition molecules according to the invention, additionally comprising amino acid sequences specifically binding to macrophages or other immunoeffector cells. For example, the recognition molecules of the invention further comprise an antibody binding site against CD64, and, in the form of a bispecific antibody or antibody fragment (diabodies), binding of macrophages to core 1-positive tumor cells takes place, resulting in combating and/or destruction thereof.

A preferred embodiment of the invention relates to radiolabeled core 1-specific recognition molecules. One preferred form involves recognition molecules based on antibodies or antibody fragments. Another preferred embodiment involves radiolabeled recognition molecules of the invention in single-chain format (including the form of dia-, tria-, tetrabodies).

Other preferred forms are radiolabeled single-chain antibody fragments and complete immunoglobulins, e.g., inventive chimeric or humanized IgG or IgM antibodies or humanized antibody fragments. It goes without saying that the invention is not restricted to these antibodies, said radioactive labels and formats of antibodies.

Antibody fragments such as the preferred multivalent scFv fragments, especially with no or very short linker, offer an advantage in the targeting of solid tumors compared to intact monoclonal antibodies. With intact antibodies exhibiting specific accumulation within the tumor area in biodistribution studies, an inhomogeneous antibody distribution with primary accumulation in the peripheral regions is noted when precisely investigating the tumor. Due to tumor necroses, inhomogeneous antigen distribution and increased interstitial tissue pressure, it is not possible to reach central portions of the tumor with such antibody constructs. In contrast, smaller antibody fragments show rapid tumor labeling, penetrate deeper into the tumor, and also, are removed relatively rapidly from the bloodstream. However, the dissociation constant of monovalent antibody fragments such as Fabs or scFv frequently is excessively small, resulting in a short residence time on the tumor cells. For this reason, multivalent antibody constructs such as multibodies (diabodies, tria-/tetrabodies), $F(ab')_2$ and other minibodies (multivalent antibody constructs consisting of binding domain and multimerization sequence, e.g., scFv and CH3 domain of an IgG) offer many advantages in tumor therapy. Multivalent constructs in a dia-/triabody format are preferred embodiments of the invention, they are advantageous in tumor therapy as a result of improved pharmacokinetic properties and have been further developed for use in tumor therapy. They can be used as vehicles for specific accumulation of e.g., cytotoxic substances such as chemotherapeutic agents or radionuclides in a tumor. By suitably selecting the radionuclides, it is possible to destroy tumor cells over a distance of several cell diameters, so that even antigen-negative tumor cells in a tumor area can be covered and poor penetration of antibodies into solid tumors can be compensated at least in part.

A particularly preferred embodiment of the invention involves radiolabeled multibodies—specifically as set forth in detail in Example 9—which combine particularly advantageous pharmacokinetic properties and, in combination, have improved tumor retention, tumor penetration, serum half-life and serum to tumor distribution ratio compared to complete immunoglobulins and scFv. Further advantages are high avidity and bacterial expression, allowing low-cost production of such recognition molecules. Advantageously, this specific format of recognition molecules according to the invention is therefore suitable for use preferably in the treatment of small primary tumors, metastases and minimal residual diseases.

A preferred embodiment of the invention involves non-radiolabeled recognition molecules. One preferred form involves recognition molecules based on antibodies or antibody fragments.

A particularly preferred embodiment involves chimeric and humanized immunoglobulins based on IgM molecules for the inhibition of liver metastasization and control of residual tumor cells.

Other preferred embodiments are toxin- or cytostatic agent-coupled chimeric or humanized IgG- and IgM-based recognition molecules of the invention and, in particular, multibodies (dia-, tria-, tetrabodies) having particularly advantageous pharmacokinetic properties as set forth above.

Another preferred embodiment involves liposomes which are loaded with e.g., toxins or cytostatic agents and bear recognition molecules of the invention on the surface thereof.

A person skilled in the art will be able to select suitable radioisotopes, toxins and cytostatic agents. Suitable techniques, methods, dosages and formulations are well-known to those skilled in the art.

Another preferred embodiment of the invention involves effector cells of the immune system having recognition molecules of the invention bound on the surface thereof, which direct/address the effector cells to core 1-bearing tumor cells, thereby mediating control and/or destruction thereof. Preferred effector cells are macrophages, dendritic cells and NK cells obtained from the patient and coupled ex vivo with the recognition molecules. Also preferred are cell lines of these types of cells. Linking is effected e.g., by means of bispecific recognition molecules which, in addition to core 1-specific components, comprise amino acids which mediate binding to the effector cells. For example, these are bispecific antibodies, complement components or constant domains of antibodies.

Another preferred embodiment involves macrophages from a patient which, following collection, are coupled with a bispecific antibody, e.g., in the form of a complete antibody, preferably chemically coupled Fab fragments or, more preferably, diabodies which, on the one hand, recognize CD64 and, on the other hand, are core 1-specific according to the invention. These macrophages, which bear the bispecific recognition molecules via CD64 specificity, are re-administered to the patient in a suitable formulation in order to combat the core 1-positive tumor. The techniques used to this end, as well as suitable methods, dosages and formulations are well-known to those skilled in the art. Another preferred embodiment involves macrophages from a patient which, following collection, are coupled with a core 1-specific antibody or antibody fragment of the invention comprising the constant portion of an antibody which binds to macrophages via the per se known Fc receptors. The recognition molecules can bind to the macrophages either as complete antibodies, preferably chimeric or humanized IgG or IgM, or as antibody fragment, e.g., scFv, Fab or multibodies in the form of a fusion protein or chemically coupled with a portion of the constant domain of antibodies, which portion is well-known to those skilled in the art. The macrophages bearing the recognition molecules are re-administered to the patient in a suitable formulation in order to combat the core 1-positive tumor. The techniques used to this end, as well as suitable methods, dosages and formulations are well-known to those skilled in the art.

Another preferred embodiment involves cell lines or cells from the body, such as the above-described effector cells which are transfected with molecules comprising the core 1-specific recognition molecules of the invention and additional elements causing expression and anchoring in the membrane, e.g., transmembrane domain, and mediating activation of the effector cells upon contact with a core 1-bearing tumor cell. The appropriate elements are well-known to those skilled in the art. For example, a dendritic cell line is transfected with a vector comprising a recognition molecule which comprises an inventive scFv or multibody and a transmembrane domain and an activating domain. In another example, macrophages are virally transfected to this end. The effector cells bearing the recognition molecules are re-administered to the patient in a suitable formulation in order to combat the core 1-positive tumor. The techniques used to this end, as well as suitable methods, dosages and formulations are well-known to those skilled in the art.

The invention also relates to nucleic acid molecules comprising one or more genetic sequences which encode at least one of the above-described recognition molecules and/or constructs according to the invention. Owing to the degenerate genetic code, said nucleic acid molecules may have highly varying sequences. The selection of the codon also depends on the cell used to produce the recognition molecules, because different codons frequently are preferred in different cells from different organisms, and there may be a strong influence on the expression rate; for example, the arginine codons AGA and AGG preferably utilized in eukaryotic genes are rarely seen in bacteria where the codons CGC and CGU are clearly more frequent. In preferred embodiments the nucleic acid molecule of the invention is a genomic DNA, a cDNA and/or an RNA. The criteria of selecting suitable codons and the production of a suitable nucleic acid molecule are well-known to those skilled in the art.

Furthermore, the invention relates to vectors for the expression of recognition molecules, specifically in cells. In the meaning of the invention, a vector is understood to be a nucleic acid molecule according to the invention, which serves to express the recognition molecule and comprises a nucleic acid sequence which includes one or more genetic sequences encoding at least one of the above-described recognition molecules and which, in particular, includes at least one promoter effecting expression of the recognition molecule. Of course, vectors may comprise additional elements well-known to those skilled in the art, which are used e.g., in the propagation of vectors for the production in suitable cells and in cloning. The nucleic acid sequences can be present on one or more vectors; in a preferred embodiment, for example, the heavy chain of an immunoglobulin of the invention is encoded by one and the light chain by another vector. In another preferred embodiment of the invention the variable domain of the light chain and the variable domain of the heavy chain are encoded as fusion protein on the same vector under one promoter. Furthermore, in the meaning of the invention, nucleic acid sequences encoding portions of a recognition molecule can be expressed by different promoters well-known to those skilled in the art. In another embodiment, said different nucleic acid sequences can be present on one common vector. Each sequence can be expressed by its own—same or different—promoter, or the sequences can be present in a bicistronic vector under a promoter. In a preferred fashion, different expression rates of the components of recognition molecules are achieved by said different promoters, improving formation of the overall recognition molecule as compared to equal expression rate of different components. It is also preferred to use promoters which can be induced so as to improve expression of the recognition molecule. In a particularly preferred fashion the vectors also comprise the regulatory elements well-known to those skilled in the art, e.g., enhancers increasing expression of the recognition molecule or components thereof, e.g., the CMV enhancer or immunoglobulin enhancer sequences. The nucleic acid molecules and vectors preferably comprise additional nucleic acid sequences which are used as signal sequences for the secretion of recognition molecules or components thereof and are per se known to those skilled in the art, e.g., PelB, OmpA or MalE for prokaryotic cell systems, or the signal peptide of the T cell receptor, of immunoglobulin chains, of t-PA or EPO for eukaryotic cell systems [Boel et al., 2000; Herrera et al., 2000]. In an advantageous fashion, this facilitates the purification and/or improves the yield of recognition molecules. The methods for the production of the above-described nucleic acids and vectors, suitable promoters, enhancers and vector constructs, as well as the criteria for the selection thereof are well-known to those skilled in the art and will be explained in detail in the examples.

In a specific embodiment of the invention the vector according to the invention also comprises nucleic acid sequences encoding viral proteins. The virus itself will be referred to as one particular form of a vector, the genetic material of which comprises a nucleic acid sequence encoding a recognition molecule according to the invention. In a preferred form the recognition molecule is a fusion protein with a virus coat protein or components thereof, making it possible that not only the genetic material comprises the nucleic acid sequence of the recognition molecule, but also that the recognition molecule itself is present on the surface of the virus in a binding-active state, e.g., an scFv recognition molecule of the invention as a fusion protein with a coat protein of adenoviruses, poxviruses or vaccinia viruses suitable for gene-therapeutic uses. This mediates addressing the virus to a core 1-expressing tumor cell, so that expression of the recognition molecule in the tumor cell takes place. This can be utilized in the expression of the recognition molecule in vivo in the organism or in vitro in a cell culture. In a preferred fashion, well-known systems are employed which use a helper virus for replication so as to ensure the safety of a gene-therapeutic method comprising said vector. Methods for the production of the above-described viral vectors, for the infection and expression of recognition molecules are well-known to those skilled in the art.

In another specific embodiment the vector of the invention comprises a fusion protein of a recognition molecule according to the invention and a protein or peptide specifically binding to a virus. Advantageously, the recognition molecules obtained can be used to address the virus to a core 1-expressing cell. Thus, for example, transfer of the genetic material can be mediated via infections, thereby allowing expression of specific molecules—encoded by the genetic material of the virus—in cells in vivo in the organism in the form of a gene therapy or in vitro in a cell culture.

Furthermore, the invention relates to a method of obtaining said recognition molecules, comprising the incorporation of one or more vectors of the invention, which include one or more nucleic acid molecules of the invention, in a suitable host cell, culturing said host cell under suitable conditions, and providing one or more recognition molecules from the cells or from the culture medium. In the meaning of the invention, the term "incorporation of vectors" represents technologies per se known to those skilled in the art, by means of which said vector is introduced in a host cell, e.g., electroporation, transfection using cationic lipids or infection, remaining therein in a transient or stable fashion. In the meaning of the invention, the term "providing one or more recognition molecules" represents technologies per se known to those skilled in the art, by means of which the recognition molecules expressed during the culturing process are obtained from the culture supernatant and/or from the cells, e.g., various protein-chemical purification steps, e.g., fractionating, concentrating, precipitating and/or chromatography. The techniques and procedures to be used in this method are well-known to those skilled in the art, and a person skilled in the art will also be able to select suitable host cells and culturing conditions, as well as methods for the provision from cells and/or culture supernatants. For example, as set forth above, a person skilled in the art will select nucleic acid sequences with suitable codons and promoter sequences adapted to the host cell so as to obtain highest possible expression of active recognition molecules. In a preferred embodiment a person skilled in the art will use e.g., affinity-chromatographic steps, e.g., chromatography on protein A or protein G or protein L, or e.g., metal ion affinity chromatography via an additionally introduced His-tag. This will be illustrated in more detail in the examples.

Apart from the steps explicitly mentioned above, the term "obtaining" also comprises additional steps such as pretreatment of the starting material or further treatments of the final product. Pretreatment procedures are per se known to those skilled in the art. In addition to the provision procedures described above, procedures of further treatment also comprise e.g., final composing and/or formulating the recognition molecule obtained by means of the production procedure into suitable forms of use and/or administration. The type of said forms of use and/or administration, e.g., solution, lyophilizate or tablet, will depend on the intended application. It is well-known to those skilled in the art which administration form is suitable for which purpose. Depending on the administration form, the recognition molecule produced using the method according to the invention can be present together with auxiliary agents, carriers or other active substances. Auxiliary agents are preferably adjuvants, other active substances, preferably immunostimulatory molecules such as interleukins. The recognition molecule produced using the method of the invention can also be chemically modified in further treatment steps. Preferably, the recognition molecule is suitably linked with one or more additional molecules, i.e., by chemical or physical interaction. As additional molecules in the meaning of the invention, other proteins or peptides are preferably used, which are covalently or non-covalently linked with the recognition molecule produced by means of the method according to the invention, e.g., in order to produce bispecific recognition molecules by linking a recognition molecule of the invention which specifically recognizes the core 1 antigen with a second molecule which e.g., specifically binds an immunoeffector cell (for example, macrophage, NK cells, dendritic cells), or e.g., a linkage with interleukins (for example, IL-2, IL-7, IL-12, IL-15), chemokines or growth factors, and by virtue of the effect of these molecules via binding of the recognition molecule of the invention, immunoeffectors are directed to the core 1-positive tumor cells, combating and/or destroying same, for example. As described above, said additional molecules or components thereof can also be part of the recognition molecule itself, in which case they would not be linked by means of the herein-described chemical or physical methods following expression of the recognition molecule. In the meaning of the invention, "immunoeffectors" are understood to be those components of the invention capable of directly or indirectly effecting control and/or destruction of core 1-positive tumor cells, e.g., immunoeffector cells such as macrophages, NK cells, dendritic cells, or effector molecules such as proteins or peptides of the complement system. Suitable as additional molecules within the scope of the method according to the invention are, in particular, substances developing a therapeutic or diagnostic effect, e.g., radioisotopes or toxins. These substances are linked with the recognition molecules using per se known procedures; for example, radioisotopes are either directly incorporated (for example, iodine) or bound via a covalently coupled chelating agent (for example, yttrium, indium, bismuth). The steps of the procedure of further treatment are well-known to those skilled in the art.

The cells used according to the invention to express the recognition molecules can be prokaryotic or eukaryotic cells, e.g., bacterial, yeast (preferably S. cerevisiae or P. pastoris), insect (D. melanogaster), plant, mammal cells (preferably hamster, mouse or human cell lines) or organisms such as transgenic animals and plants. Preferably, E. coli is used for expression of the recognition molecules of the invention in a prokaryotic system, and the mammal cell lines NS0, SP2/0, CHO-K1, CHOdhfr-, COS-1, COS-7, HEK293, K562, Namalwa or Percy 6 for expression in a eukaryotic system.

Furthermore, the present invention relates to host cells produced using the method described above, by means of which host cells recognition molecules of the invention can be produced. Of course, the host cells can be part of a clone or represent the clone themselves. The invention also relates to organisms comprising the host cells of the invention. Techniques to be used and methods of producing such organisms are well-known to those skilled in the art.

The invention also relates to compositions for therapeutic, prophylactic or diagnostic purposes, comprising at least one recognition molecule of the invention in a suitable, especially pharmaceutically suitable form or composition. More specifically, the pharmaceutical composition comprises additional materials and substances, e.g., medical and/or pharmaceutical-technical adjuvants. In the meaning of the invention, pharmaceutical compositions used for therapeutic and prophylactic purposes, as well as pharmaceutical compositions used as in vivo diagnostic agent will be regarded as drugs. In another preferred embodiment, compositions for ex vivo diagnostics are concerned, which may contain additional materials and substances. This embodiment will be illustrated in more detail in the description of diagnostic agents.

According to the invention, "drugs or pharmaceutical compositions"—used in a synonymous fashion herein—are substances and formulations of substances intended to cure, alleviate or avoid diseases, illness, physical defects or pathological affection by application on or in the human body. According to the invention, medical adjuvants are substances used as active ingredients in the production of drugs. Pharmaceutical-technical adjuvants serve to suitably formulate the drug or pharmaceutical composition and, if required during the production process only, can even be removed thereafter, or they can be part of the pharmaceutical composition as pharmaceutically tolerable carriers. Examples of pharmaceutically tolerable carriers will be given below. Drug formulation or formulation of the pharmaceutical composition is optionally effected in combination with a pharmaceutically tolerable carrier and/or diluent. Examples of suitable pharmaceutically tolerable carriers are well-known to those skilled in the art and include phosphate-buffered saline, water, emulsions such as oil/water emulsions, various types of detergents, sterile solutions, and so forth. Drugs or pharmaceutical compositions comprising such carriers can be formulated by means of well-known conventional methods. These drugs or pharmaceutical compositions can be administered to an individual at a suitable dose, e.g., in a range of from 1 µg to 10 g of recognition molecules per day and patient. Doses of from 1 mg to 1 g are preferred. Administration can be effected on various routes, e.g., intravenous, intraperitoneal, intrarectal, intragastrointestinal, intranodal, intramuscular, local, e.g., intratumoral, but also subcutaneous, intradermal or on the skin or via mucosa. Administration of nucleic acids can also be effected in the form of a gene therapy, e.g., by means of viral vectors described above. The kind of dosage and route of administration can be determined by the attending physician according to clinical factors. As is familiar to those skilled in the art, the kind of dosage will depend on various factors, such as size, body surface, age, sex, or general health condition of the patient, but also on the particular agent being administered, the time period and type of administration, and on other medications possibly administered in parallel.

More specifically, the pharmaceutical compositions or drugs comprise a pharmacological substance which includes one or more recognition molecules of the invention or/and nucleic acid molecules encoding same, in a suitable solution or administration form. Administration thereof can be effected either alone or together with appropriate adjuvants described in connection with drugs or pharmaceutical compositions, or in combination with one or more adjuvants, e.g., QS-21, GPI-0100 or other saponines, water-oil emulsions such as Montanide adjuvants, polylysine, polyarginine compounds, DNA compounds such as CpG, Detox, bacterial vaccines such as typhoid vaccines or BCG vaccines and/or other suitable material enhancing the effect, preferably immunostimulatory molecules such as interleukins, e.g., IL-2, IL-12, IL-4 and/or growth factors such as GM-CSF. They are mixed with the recognition molecules of the invention according to well-known methods and administered in suitable formulations and dosages. Formulations, dosages and suitable components are well-known to those skilled in the art.

Obviously, the pharmaceutical composition or drug can also be a combination of two or more of the inventive pharmaceutical compositions or drugs, as well as a combination with other drugs, tumor vaccines or tumor treatments, such as antibody therapies, chemotherapies or radiotherapies, suitably administered or applied at the same time or separately in time. The production of the drugs or pharmaceutical compositions proceeds according to per se known methods.

In particular, the drugs or pharmaceutical compositions can be used in the treatment of core 1-positive tumor diseases such as mammary carcinomas, cervical carcinomas, ovarian carcinomas, colon carcinomas, gastrointestinal carcinomas, pancreas carcinomas, lung carcinomas, prostate carcinomas. Such tumor diseases may also include core 1- and/or core 2-positive tumor diseases. For example, the treatment is directed against primary tumors, minimal residual tumor diseases, relapses and/or metastases. The treatment of the tumors can also be effected as an adjuvant treatment. The drugs can also be used in the prophylaxis of core 1-positive tumor diseases. For example, prophylactic use is directed to the prophylaxis of tumors and metastases. The tumor agents are administered in a suitable form according to well-known methods. A preferred variant is injection or administration of the drugs intravenously, locally in body cavities, e.g., intraperitoneal, intrarectal, intragastrointestinal routes, locally, e.g., directly in a tumor, in organs or lymphatic vessels (intranodal), but also subcutaneously, intradermally or on the skin, and intramuscularly. In a preferred fashion, types of administration can also be combined, in which case administration can be effected on different days of treatment or on one day of treatment. According to the invention, it is also possible to combine two or more of the inventive drugs or pharmaceutical compositions or one or more drugs of the invention with one or more drugs or tumor treatments, such as antibody therapies, chemotherapies or radiotherapies, suitably administered or applied at the same time or separately in time.

The present invention also relates to a method for the production of a drug or a pharmaceutical composition, comprising the steps of producing recognition molecules and further comprising the step of formulating the recognition molecules of the invention into a pharmaceutically tolerable form. The recognition molecules preferred to this end are described above as further embodiments of the treatment of tumor diseases and prophylaxis, as well as under in vivo diagnostic agents below.

Hence, the recognition molecules of the invention and the substances and compositions produced using the method according to the invention can be used in a preferred fashion in prophylaxis, diagnosis, follow-up and/or treatment of tumor diseases. Furthermore, it is preferred to use the recognition molecules, vectors and/or the drug or pharmaceutical composition in the prophylaxis and/or treatment of cancer diseases, including tumors and metastases.

In a preferred embodiment the cancerous disease or tumor being treated or prevented is selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immunosuppression-related malignancies and/or tumor metastases.

More specifically, the tumors may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma); histiocytic functional disorder; leukemia (e.g., in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Leydig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phylloides; hemangiosarcoma; lymphangiosarcoma; myxosarcoma, ovarian carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia.

In another preferred embodiment the cancerous disease or tumor being treated or prevented is selected from the group of cancerous diseases or tumor diseases comprising cells including the core 1 in the definition according to the invention, selected from the group of: tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs, comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarian carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, Hodgkin's disease, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppression-related malignancy comprising AIDS-related malignancies such as Kaposi sarcoma, AIDS-associated lymphomas, AIDS-associated lymphomas of the central nervous system, AIDS-associated Hodgkin disease, and AIDS-associated anogenital tumors, transplantation-related malignancy, metastasized tumors comprising brain metastases, lung metastases, liver metastases, bone metastases, pleural and pericardial metastases, and malignant ascites.

In another preferred embodiment the cancerous disease or tumor being treated or prevented is selected from the group comprising cancerous diseases or tumor diseases such as mammary carcinomas, gastrointestinal tumors, including colon carcinomas, stomach carcinomas, pancreas carcinomas, colon cancer, small intestine cancer, ovarian carcinomas, cervical carcinomas, lung cancer, prostate cancer, renal cell carcinomas and/or liver metastases.

The recognition molecules of the invention can be directly employed in the treatment or prophylaxis of tumor diseases or coupled with additional effector structures. According to the invention, "effector structures" are understood to be chemical or biochemical compounds, molecules or atoms which directly or indirectly cause destruction or damage, including e.g., growth reduction or growth inhibition, of tumor cells. For example, these include radioisotopes, toxins, cytostatic agents and other effector molecules such as cytokines and chemokines or other structures representing effectors themselves or being coupled to said effector molecules, e.g., liposomes loaded with toxins or cytostatic agents, which bear the recognition molecules according to the invention. In the latter example of liposomes, particularly those effector structures are concerned which, in addition to the recognition molecule for tumor specificity, bear molecules responsible for reception of effector structures or components thereof in cells, such as antibodies against receptors causing receptor-mediated endocytosis. In such cases, the recognition molecules preferably comprise a transmembrane domain allowing their insertion in the liposomal membrane, or, in another preferred embodiment the recognition molecules are chemically coupled on the liposome surface. The techniques used to this end are well-known to those skilled in the art, including production of the liposomes. Linking of the recognition molecules with other effector structures also proceeds according to per se known methods. As already set forth above, linking can be effected e.g., directly by covalent or non-covalent loading, by chemical coupling, which may require an additional chemical or biological molecule, e.g., a chelating agent or linker, or in the form of fusion proteins or peptides via fusion. The recognition molecules are employed in the treatment of tumor diseases with core 1-bearing tumors and/or—for a subgroup of recognition molecules of the invention described above for their specificity for core 1 and core 2—core 2 and/or core 1-bearing tumor cells or in prophylaxis which, for example, prevents formation of primary tumors or metastases. One preferred objective is treatment of minimal residual disease and of metastases. Another preferred use is inhibition of liver metastasization of core 1 and/or core 2-positive tumor cells. The recognition molecules according to the invention are administered in a suitable formulation, in one go or repeatedly, at suitable intervals and in suitable doses.

Infra and supra, in the meaning of the invention the core 1 antigen is understood to be also core 1 and/or core 2, and core 1-positive cells or tumor cells and/or tissues are understood to be also core 1 and/or core 2-positive cells or tumor cells and/or tissues.

In a preferred embodiment the above-described radioactive recognition molecules according to the invention are combined with an application of non-labeled core 1-specific recognition molecules according to the invention. This helps towards an improvement of the background and more specific binding to the tumor by saturating potential core 1-bearing molecules in the blood. To this end, IgM-derived recognition molecules are preferably used, e.g., the cIgM described in the examples or a humanized form thereof, because they primarily bind to core 1 antigen in blood, thereby reducing the background and serum radioactivity load and increasing the relative tumor targeting, while limiting penetration into tissues and tumors by virtue of the size of the molecules. The procedures and technologies used to this end are well-known to those skilled in the art, and a person skilled in the art will also be able to devise a suitable dose, formulations, route of application, and time of administering said non-labeled recognition molecules.

Also preferred is the use of viral vectors in gene-therapeutic applications wherein specifically the surface of the viruses bears recognition molecules according to the invention.

The invention also relates to methods using the recognition molecules according to the invention, which methods allow identification and/or recovery of core 1-bearing molecules from a large pool of different molecules, which can be used with advantage in applications in tumor treatment, tumor prophylaxis and tumor diagnosis. According to the invention, core 1-bearing molecules are understood to be molecules which bear core 1 and/or core 2 structures and are bound by the recognition molecules of the invention in a specific fashion. According to the invention, core 1-bearing molecules are glycoproteins, glycopeptides and/or glycolipids, as well as cells or other vehicles, such as viruses, bacteria, components of cells, such as exosomes or cell lysates, or liposomes, which contain one or more core 1 structures. The core 1-bearing molecules can be accumulated or isolated from cells or cell lines, culture supernatants, tumor tissues, tumor cells, or body fluids such as blood, blood serum, lymph, urine, spinal fluid or sperm.

Mutatis mutandis, the definitions of terms introduced above also apply to terms in the methods described below.

Core 1-bearing molecules are identified and/or isolated and obtained in a method of the invention by binding to the above-described core 1-specific recognition molecules according to the invention. According to the method of the invention, the above-described core 1-bearing molecules can be obtained from body fluids or from supernatants of cell cultures by means of affinity chromatography. It is possible to combine further purification and/or concentration steps with one or more affinity-chromatographic steps according to per se known methods. Likewise, tumor-associated core 1-bearing molecules can be obtained from tumor cells, tumor tissues or tumor cell lines by upstream insertion of a suitable step according to per se known methods, so that cell-associated core 1-bearing molecules can be put to affinity purification, e.g., by solubilization with suitable detergents or by cleavage using proteolysis or by cell lysis.

In another method of the invention, core 1-bearing molecules or cells are obtained from tissues. To this end, the tissue is digested according to per se known methods in order to provide access to the core 1-bearing molecules or cells, e.g., by means of proteolytic or mechanical methods. Such methods are well-known to those skilled in the art.

As set forth above, core 1-positive cells or cell lines are also isolated or accumulated using said core 1-specific recognition molecules and separated from cells bearing no or low quantities of core 1 structures. The term "isolation or accumulation of cells" is understood to include all measures of separating cells having formed a complex with the recognition molecules of the invention as a result of bearing said core 1 structures. Such methods are well-known to those skilled in the art. In a preferred fashion, FACS or MACS methods are employed to this end. For example, accumulation proceeds via binding of recognition molecules of the invention to the core 1 structure on the cell surface and subsequent selection of thus labeled cells by binding to carrier materials specifically interacting with the recognition molecule, e.g., anti-mouse IgM antibodies coupled to magnetic beads (MAC sorting). Furthermore, the core 1-specific recognition molecules can be coupled covalently to a carrier. Another example is recovery using an FAC sorter which sorts cells bearing fluorescence-labeled recognition molecules. Both of these methods are well-known to those skilled in the art. The core 1-positive cells accumulated in this way can be used in the production of vaccines, e.g., for loading dendritic cells or directly as tumor cell lysate in a vaccine composition. Previous accumulation of core 1-positive cells is to provide higher tumor specificity of vaccination. These methods are well-known to those skilled in the art.

The present invention also relates to methods of producing a diagnostic agent, comprising the steps of the inventive method for the production of core 1-specific recognition molecules according to the invention and, in addition, comprising the step of formulating the recognition molecules in a diagnostically usable form.

According to the invention, the term "diagnostic agent" defines substances and preparations of substances intended to recognize diseases, illness, physical defects or pathological affection by application on or in the human body. Preferably, parts of the human body are understood to be body fluids such as blood, blood serum, lymph, urine, spinal fluid or sperm, or tissue biopsies or samples.

Formulating the diagnostic agent preferably comprises modification of the produced recognition molecules with substances allowing detection of the core 1 antigen and also, in specific embodiments depending on the fine specificity of the recognition molecule according to the invention, of core 2 antigen by definition. Suitable substances are well-known in the art. Based on the selection of a substance, a person skilled in the art will be able to take suitable measures in order to formulate a diagnostic agent.

According to the invention, it is also possible for diagnostic purposes to couple substances to the recognition molecules according to per se known methods, which facilitate detection of core 1 antigens and/or carrier molecules and/or cells thereof, e.g., by biotinylation, fluorescence labeling, radioactive labeling or enzyme linking of recognition molecules.

Another method of tumor diagnostics and prognosis uses recognition molecules of the invention which recognize core 1 antigens and/or carrier molecules thereof in serum of humans. Determination is preferably qualitative, quantitative and/or in time-dependent relative quantities according to per se known methods. According to the invention, the same methods are also used in the follow-up of tumor diseases and to control the course of treatment, including monitoring of immune responses, and for control and dosage of tumor treatments. The techniques used in such methods are per se well-known, e.g., ELISA, Western blot, FACS (fluorescence-activated cell sorting), MACS (magnetic-activated cell sorting), ADCC (antibody-dependent cell cytotoxicity), CDC (complement-dependent cytotoxicity), immunocytochemistry and immunohistochemistry.

The preferred inventive methods of tumor diagnostics and prognosis use core 1-specific recognition molecules of the invention in per se well-known methods to detect the core 1 antigen in serum or in tissue preparations. In these methods, core 1 antigen on carrier molecules, core 1 present in immune complexes on carrier molecules and/or core 1 bound on cells is detected, and the presence of core 1 antigen and/or core 1-bearing molecules is determined qualitatively, quantitatively and/or in relative quantities according to per se known methods. According to the invention, the same methods are employed in the follow-up of tumor diseases and to control the course of treatments. The techniques used in such methods are per se well-known, e.g., ELISA, Western blot, FACS (fluorescence-activated cell sorting), MACS (magnetic-activated cell sorting), ADCC (antibody-dependent cell cytotoxicity), CDC (complement-dependent cytotoxicity), immunocytochemistry and immunohistochemistry.

One preferred embodiment is a tissue rapid test wherein the tissue samples are stained with fluorescence-labeled recognition molecules of the invention in a immunohistological method. In another preferred method the recognition molecule according to the invention, preferably an isotype IgM antibody, is combined with another antibody specifically recognizing the MUC1 antigen, preferably isotype IgG1. The advantage is that, e.g., in gastrointestinal carcinoma diagnostics (e.g., colorectal carcinomas and stomach carcinomas), recognition at an early stage and, at the same time, prognosis with respect to the course of disease and/or risk of liver metastasization is possible, higher levels of core 1 antigen indicating a more unfavorable prognosis as to the course and a probability of liver metastasization increased by several times. In another preferred embodiment the antibodies and recognition molecules are directly labeled with various fluorescent dyes, e.g., Cy3 and Cy5 or Cy3 and FITC. In one embodiment, wherein signal intensification is advantageous, the antibodies and/or recognition molecules are enhanced by labeled secondary antibodies or biotin-streptavidin. Advantageously, different isotypes and/or sequences of species in the constant region of antibodies are used. The techniques and methods used to this end, e.g., of labeling and immunohistology, as well as the selection of suitable formats of recognition molecules are well-known to those skilled in the art. The diagnostic method described above is not restricted to gastrointestinal tumors, but can be used in any tumor disease involving the core 1 antigen.

In another preferred embodiment a serological test is performed, using a sandwich ELISA procedure. This consists of a scavenger antibody, which binds carrier molecules of the core 1 antigen from serum to a solid phase, and a detection antibody which, according to the invention, also includes other recognition molecules of the invention which recognize the core 1 antigen. In this way, it is possible to distinguish which carrier molecule is the one that bears core 1. In a preferred form it is possible to draw conclusions about the origin of the primary tumor. A variety of antibodies recognizing glycoproteins bearing O-glycosylations can be used as scavenger antibodies. A preferred embodiment uses antibodies against the MUC1 epithelial mucin as scavenger antibody, which frequently bears core 1 in tumor cases. In another embodiment, all antigens bearing the core 1 antigen are determined in blood. This is possible because the core 1 antigen is present in a plurality of copies per carrier molecule. According to the invention, a core 1-specific recognition molecule of the invention is used as scavenger antibody, and a labeled core 1-specific recognition molecule of the invention is used as detection antibody, in which case the recognition molecules do not have to be antibodies.

In a preferred embodiment an IgM as recognition molecule is used at least as scavenger or detection antibody. In another preferred embodiment the detection antibody is labeled with biotin, and the system is detected via streptavidin in combination with a suitable detection method. For example, suitable detection methods are POD labeling or fluorescence labeling of streptavidin.

For a serological tumor test, another preferred embodiment of the invention combines the determination of core 1, as described above, with the determination of other serological tumor markers, e.g., PSA, CEA or AFP. One embodiment preferred in this case is determination of MUC1 and core 1 antigen. In a preferred embodiment, MUC1 is immobilized from the serum on a solid phase, using an MUC1-specific antibody, and detected with a second, anti-MUC1-specific antibody as detection antibody, preferably one with improved recognition of the DTR region in glycosylated form, and the core 1 antigen is detected on MUC1 immobilized by means of an anti-MUC1 scavenger antibody, using a recognition molecule according to the invention. This diagnostic test combines early recognition with a prognostic statement as to the course of disease and/or the probability of liver metastasization. The techniques used to this end, e.g., labeling and serology, including the detection methods, are well-known to those skilled in the art. The diagnostic methods described above are not restricted to gastrointestinal tumors, but can be used in any tumor bearing the core 1 antigen. The serological tests described above are used in diagnosis, monitoring the course of a tumor disease, and in the prognosis of core 1 antigen-positive tumors.

In another method according to the invention, the core 1-specific recognition molecules of the invention are used in in vivo diagnostics. To this end, the recognition molecules are labeled using suitable, per se known methods and thus made available for per se known imaging methods in humans, e.g., radioimmunodiagnostics, PET scanning methods or immunofluorescence endoscopy, e.g., by coupling and/or loading with appropriate molecules, e.g., radioactive isotopes such as indium, or fluorescent dyes such as Cy3, Cy2, Cy5 or FITC. In a preferred embodiment, multibodies according to the invention are covalently coupled with a suitable chelating agent (for example, DOTA or DTPA) and, loaded with indium-111, used in in vivo diagnostics. In a preferred embodiment, they are administered intravenously at a dose appropriate to the individual, and the location of the core 1 antigen and of a potential tumor is measured according to per se known methods. The methods and technologies used to this end, including imaging methods, are well-known to those skilled in the art, and a person skilled in the art will also be able to devise a suitable dose and formulations.

In another preferred embodiment, immunoglobulins, preferably IgM and IgG, are radiolabeled as described above and illustrated in more detail in the examples, e.g., with indium-111, and administered locally into the tumor or blood vessels supplying or evacuating the tumor. In one embodiment, this is used to determine the size of the tumor, and in another embodiment, to determine affected lymphatic nodes. The methods and technologies used to this end are well-known to those skilled in the art, and a person skilled in the art will also be able to devise a suitable dose and formulations.

In another embodiment the radioactively labeled recognition molecules are also administered via other routes of application. Preferred routes are intraperitoneal, intranodal or intrarectal and intragastrointestinal, respectively. Intraperitoneal is particularly advantageous in the determination of tumors accessible through the peritoneum and/or metastasizing therein, e.g., ovarian carcinomas and certain gastrointestinal carcinomas. Intrarectal or intragastrointestinal administration is advantageous in some gastrointestinal tumors and in localization and size determination thereof. In some cases, intranodal can be used for direct infiltration of single lymphatic nodes.

In a preferred embodiment the above-described radioactive recognition molecules are combined with an application of non-labeled core 1-specific recognition molecules of the invention for in vivo diagnostic agents. This is to improve the background. To this end, IgM-derived recognition molecules are preferably used because they primarily bind to core 1 antigen in blood, thereby significantly reducing the background, while limiting penetration into tissues and tumors by virtue of the size of the molecules. The methods and technologies used to this end are well-known to those skilled in the art, and a person skilled in the art will also be able to devise a suitable dose, formulations, route of application, and time of administering said non-labeled recognition molecules.

In another preferred embodiment, recognition molecules of the invention, preferably immunoglobulins, multibodies or antibody fragments, more preferably IgM, IgG and multibodies, are labeled with a fluorescent dye and administered in vivo. Preferred routes of application are intrarectal, intragastrointestinal, intraperitoneal, intravenous and into supplying or evacuating blood vessels. A particularly preferred embodiment is used to localize gastrointestinal carcinomas by means of fluorescence endoscopy following application of fluorescence-labeled recognition molecules. In another preferred embodiment a recognition molecule of the invention is combined with at least one antibody to another tumor antigen, preferably anti-MUC1 antibody. In a preferred fashion, different fluorescent dyes are used, allowing differentiation of the recognition molecules and antibodies, thereby combining a prognostic statement with early recognition and a greater number of cases. Preferred fluorescent dyes are those having lower background fluorescence, which are well-known to those skilled in the art. The methods and technologies used to this end, including imaging methods, e.g., fluorescence endoscopy, are well-known to those skilled in the art, and a person skilled in the art will also be able to devise a suitable dose, formulations, route of application, and time of administering said non-labeled recognition molecules.

The invention has several advantages: The core 1-specific recognition molecules of the invention recognize the types of carcinomas in a specific fashion, which is why they can be used with advantage in diagnosis and/or therapy of a large number of tumor patients with different indication. Moreover, the recognition molecules advantageously show virtually no binding on normal tissues. Compared to well-known tumor markers, this is a particular advantage and an outstanding property of the recognition molecules according to the invention. Another advantage is that the recognition molecules recognize the core 1 antigen independently of the carrier. One particular advantage of the recognition molecules of the invention is their high specificity for tumor tissue. In particular, this is due to the high specificity for definite carbohydrate antigens. Namely, non-specific recognition of other carbohydrate structures would increase the risk of non-specific recognition of non-tumor tissue. Furthermore, the recognition molecules of the invention exhibit high affinity. In particular, this presents a way of constructing lower-valent fragments such as IgG and multibodies. The option of having these different formats available is advantageous in the development of therapeutic agents. The core 1 and/or core 2 structures on the cell surface increase the probability of metastase formation, e.g., of liver metastases; by blocking the core 1 and/or core 2 structures with recognition molecules, formation of metastases is reduced or inhibited.

Without intending to be limiting, the invention will be explained in more detail with reference to the examples.

EXAMPLES

1. Preparation of Core 1-Specific Multibodies with Short Linkers

Figure 2:
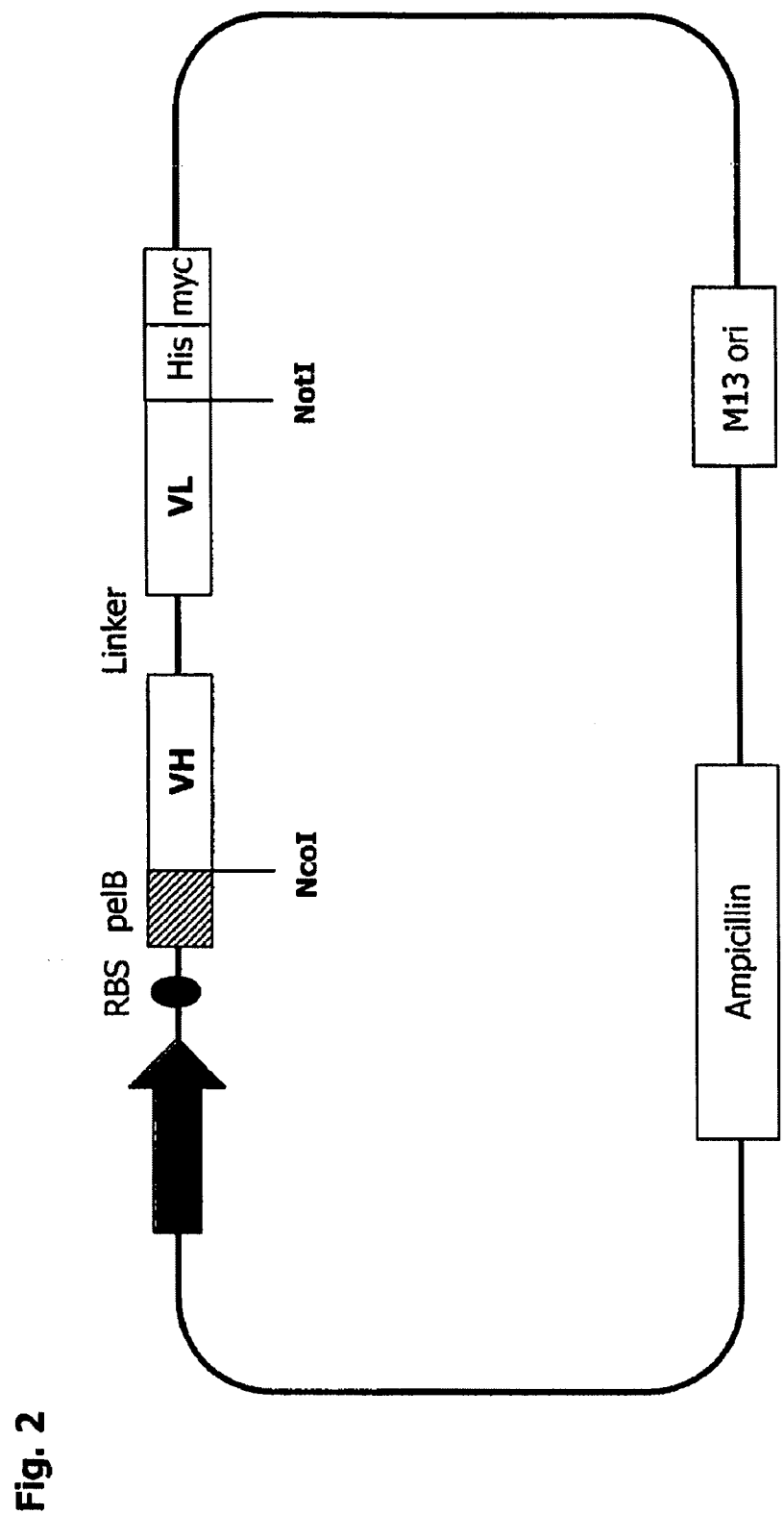

Multibodies having the sequences SEQ ID Nos. 96 to 106 were formed by shortening or deletion of the linker between the $V_H$ and $V_L$ of the single-chain antibody having the sequence SEQ ID NO. 95 (FIG. 1a). To this end, $V_H$ and $V_L$ were amplified with specific primers in such a way that 22 nucleotides at the 3' end of $V_H$ and at the 5' end of $V_L$ formed a complementary region (FIG. 1b, PCR I and PCR II) and subsequently, following purification, the two PCR fragments were linked in an SOE-PCR (FIG. 1b, PCR III). Finally, the PCR fragment was cloned into a prokaryotic expression vector via NcoI/NotI. This vector includes the lacZ promoter, a ribosome binding site (RBS), the M13 origin, the pelB signal sequence for secretion into the periplasm, an ampicillin resistance gene, and a cloning cassette to couple a hexahistidine tag for efficient purification and a c-myc-tag to the C-terminal end of the scFv (FIG. 2).

2. Bacterial Expression and Purification of the Core 1-Specific Multibodies

The antibody fragments from Example 1 were expressed in *Escherichia coli* and purified. To this end, the corresponding plasmid was transformed in electrocompetent *E. coli* by means of electroporation and cultured in 2×TY medium (10 g of yeast extract, 16 g of tryptone, 5 g of NaCl per liter) with 100 μg/ml ampicillin overnight. This culture was diluted 1:100 with 2×TY medium added with 100 μg/ml ampicillin and 0.5% glucose and incubated at 37° C. until an $OD_{600\,nm}$ of about 0.6 was reached. Thereafter, the culture was added with 1 mM IPTG for induction and incubated at 25° C. for another 5 hours. The bacteria were harvested by centrifugation at 4000×g for 20 min, the cell pellet was resuspended in TES buffer (30 mM Tris-HCl, pH 8.0, 20% saccharose, 1 mM EDTA) and incubated on ice for 20 min. Subsequently, 5 mM MgSO$_4$ was added, and the suspension was incubated on ice for another 20 min. The periplasm fraction was obtained by centrifugation at 4000×g for 60 min and dialyzed against binding buffer (50 mM phosphate buffer, pH 8.0, 300 mM NaCl, 10 mM imidazole) at 4° C. overnight. The antibody fragments contained in the periplasm fraction were purified by metal ion affinity chromatography (HiTrap Chelating HP, Amersham Pharmacia Biotech) using the C-terminal His-tag. To this end, the dialyzed fraction was loaded on a column previously equilibrated with binding buffer, and the non-binding proteins were washed from the column with washing buffer (50 mM phosphate buffer, pH 8.0, 300 mM NaCl, 30 mM imidazole). Subsequently, the antibody fragments were eluted with elution buffer (50 mM phosphate buffer, pH 8.0, 300 mM NaCl, 300 mM imidazole). The above purification protocol was used for all core 1-specific antibody fragments having a hexahistidine tag, e.g., the humanized single-chain antibodies from Example 6.

3. Analysis of Core 1-Specific Multibodies in scFv Format with Varying Linker Length in an ELISA Multibodies having the amino acid sequences SEQ ID Nos. 95, 96, 97, 98, 99, 100, 101, 103, 104 and 105 were expressed in *E. coli* as described above and the periplasm fractions obtained. Asialoglycophorin (Sigma), which is a core 1-bearing glycoprotein, was used as antigen in the ELISA. Using stock solutions (1 mg in 1 ml of bidist. H$_2$O) stored in portions at −20° C., a dilution of 5 µg/ml in PBS was produced. 50 µl/well of the above was pipetted in a microtiter plate (NUNCLON-TC Microwell 96 F), and the test plate was incubated at 4° C. overnight. On the next day, the test plate was washed 3 times with PBS/0.2% TWEEN. Subsequently, non-specific binding sites were blocked with 2% BSA in PBS, and 50 µl of each fraction diluted with PBS/1% BSA in different dilution steps was applied and incubated at 37° C. for 2 hours. After three wash steps with PBS/0.2% TWEEN, peroxidase-coupled anti-His-tag antibodies were employed as secondary antibodies to detect the specifically bound antibody constructs. To detect the bound secondary antibody, a color reaction with TMB (3,3',5,5'-tetramethylbenzidine) was performed. After 15 minutes the reaction was quenched by adding 2.5 N H$_2$SO$_4$. Measurement was performed using a microtiter plate photometer with 450 nm filter in dual mode versus 630 nm reference filter. The result is illustrated in FIG. 3. Step-by-step linker length reduction results in increased binding to asialoglycophorin. The best binding properties are seen in the variants having SEQ ID Nos. 104 and 105. These multivalent constructs in dia/triabody format are preferred embodiments of the invention and offer advantages in tumor therapy owing to their improved pharmacokinetic properties.

Figure 4:
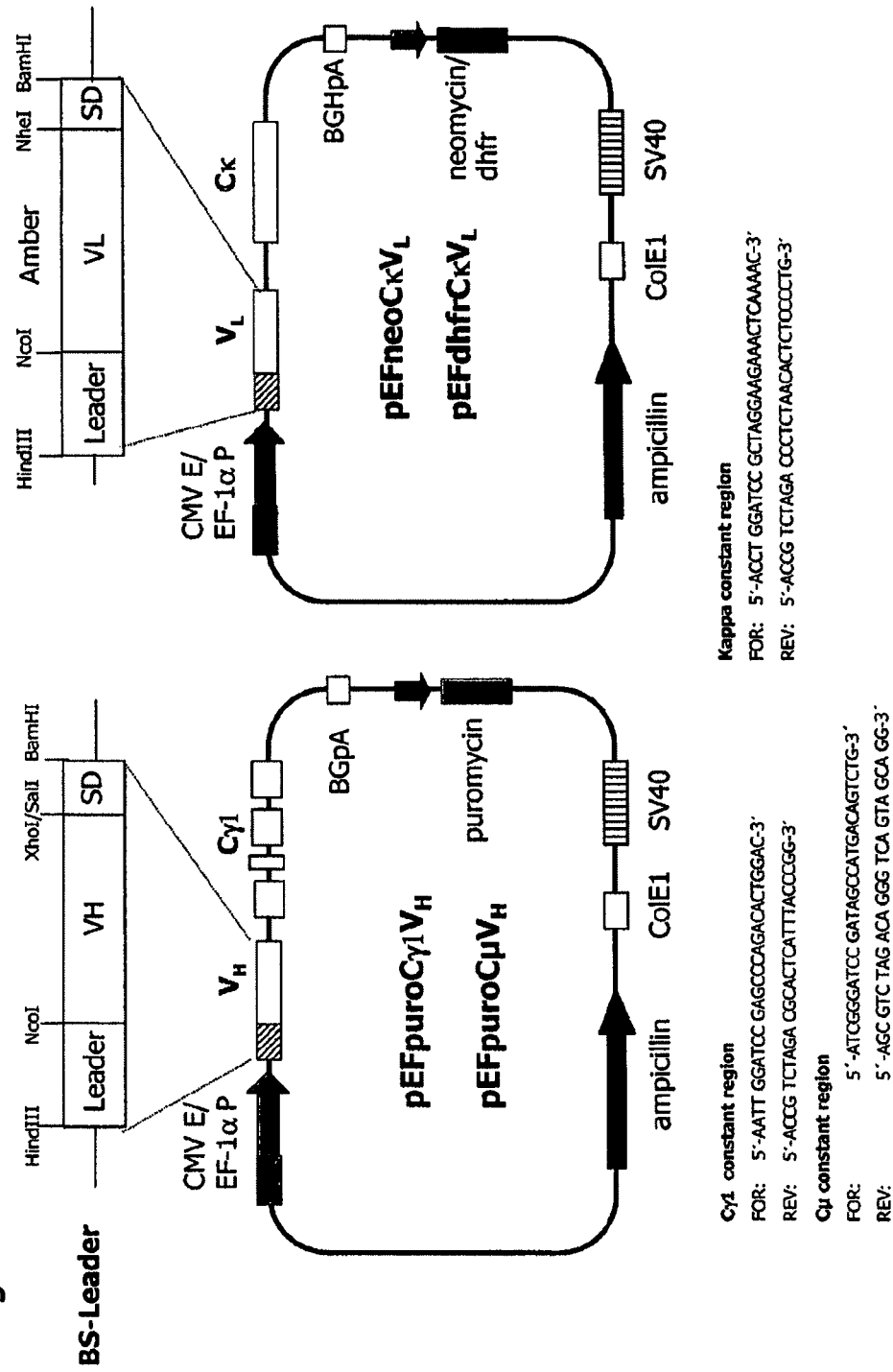

4. Cloning of Vectors to Express Chimeric Core 1-Specific IgG and IgM Antibodies The NcoI/XhoI DNA fragment from the scFv vector, which encodes V$_H$ (FIG. 4), was cloned into the NcoI/SalI-cut BS Leader vector. The BS Leader vector includes a cloning cassette to introduce the T cell receptor signal peptide sequence at the 5' end and a splice donor sequence at the 3' end of the sequences of the variable domains (FIG. 4). The V$_L$ sequence of the corresponding antibody was amplified with specific primers to introduce the NcoI restriction site at the 5' end and the NheI restriction site at the 3' end in the PCR using the scFv sequence as template and, following NcoI/NheI digestion, cloned into the likewise digested BS Leader vector. Thereafter, each HindIII/BamHI fragment from the BS Leader vector was cloned into the corresponding eukaryotic expression vector. These vectors (pEFpuroCγ1V$_H$, pEFpuroCµV$_H$ and pEFneoCκV$_L$) include EF-1α-promoter and HCMV enhancer, SV40 origin, BGH polyadenylation signal, puromycin resistance gene in the vector for the heavy chain and neomycin resistance gene or dehydrofolate reductase gene in the vector for the light chain, as well as the genomic sequences of the human constant γ1 region or µ region for the heavy chain or of the human constant κ region for the light chain (primers for amplification from genomic human DNA and vector map see FIG. 4).

5. Eukaryotic Expression of Core 1-Specific Chimeric IgG and IgM Antibodies in CHO Cells and Purification Thereof To express the chimeric antibodies cIgG-Karo4 consisting of the sequences SEQ ID Nos. 111 and 113 and cIgM-Karo4 consisting of the sequences SEQ ID Nos. 112 and 113, CHOdhfr-cells (ATCC No. CRL-9096) were co-transfected with a mixture of vectors for the heavy and light chains (1:3) by means of electroporation (10$^6$ cells/ml, 500 V, 50 s) and cultured in selection medium (CHO-S-SFM II medium (Life Technologies), HT supplement (Biochrom), 400 µg/ml G418, 5 µg/ml puromycin) for 2 weeks. Following single-cell cloning in a 96-well plate, the supernatants were tested in an ELISA (asialoglycophorin as antigen, anti-human Fcγ1-POD-coupled or anti-human Fc5µ-POD-coupled (Dianova) as secondary antibody), and the clone with the highest antibody production rate was selected (about 0.5 µg/10$^6$ cells/24 h).

For antibody production, the stably transfected CHO cells secreting the chimeric IgG and IgM, respectively, were cultured in spinner flasks in CHO-S-SFM II medium, supplemented with HT supplement, until a cell density of about 1×10$^6$ cells/ml was reached. Following removal of the cells from the cell culture supernatant by centrifugation (400×g, 15 min), the chimeric antibody was purified using a protein A column (HiTrap r-protein A FF, Amersham Pharmacia Biotech) for chimeric IgG or an anti-human Fc5µ antibody affinity column. The purified antibody fraction eluted by sudden pH change was re-buffered in PBS and concentrated using Centriprep centrifuge tubes (cut-off 50 kDa, Millipore).

6. Sequence Adaptation of the Core 1-Specific Antibody Sequences to Human Germ Line Sequences To adapt the core 1-binding antibody sequences to human sequences, a search for homologous sequences was conducted in the data base of human germ line sequences, and humanized core 1-binding sequences were developed using human consensus sequences and findings concerning the canonical structure of human antibodies. The human germ line sequence V$_H$1-46 was used as model for the variable heavy chain, and the sequence of A18 for the variable light chain.

The humanized V$_H$ and V$_L$ sequences SEQ ID Nos. 56 to 79 and 85 to 94, respectively, were produced using a gene assembly PCR (single-overlap extension PCR). The PCR reaction proceeded according to the following scheme: first denaturation at 94° C. for 2 min, followed by 30 cycles of denaturation at 94° C. for 45 s, annealing at 55° C. for 45 and elongation at 73° C. for 1.5 min, and finally, an elongation step at 73° C. for 7 min.

The V$_H$ and V$_L$ chains thus produced were cut using the enzymes NcoI and XhoI or NotI and XhoI and cloned into a cloning vector (pLitmus 28 and pBLUESCRIPT KS, respectively) for sequencing. The proper V$_H$ and V$_L$ chains were subsequently re-amplified to insert a BbsI restriction site at the 3' end of V$_H$ and at the 5' end of V$_L$ in order to link V$_H$ and V$_L$ via the latter using only one alanine as linker. Following ligation, the complete scFv (the ligation products) were amplified using the flanking primers and cloned into a bacterial expression vector.

7. Specificity Analysis of Core 1-Specific Recognition Molecules in an ELISA

Various carbohydrate-PAA conjugates (synthesomes) and glycoproteins were used as antigens: asialoglycophorin (AGP), glycophorin (GP) and asialofetuins (Sigma); PAA (poly[N-(2-hydroxyethyl)acrylamide] conjugates: Galβ1-3GalNAcα1-OC$_3$H$_6$NH-PAA and Galβ1-3GalNAcα1-p-OC$_6$H$_4$NH-PAA as core 1 (α-anomer) conjugates with varying linker lengths, Galβ1-3GalNAcβ1-OC$_3$H$_6$NH-PAA as β-anomer of core 1, Galα1-3GalNAcα1-OC$_3$H$_6$NH-PAA and Galβ1-3GalNAcβ1-OC$_3$H$_6$NH-PAA as additional stereoanomers of core 1, the core 2 structure Galβ1-3(GlcNAcβ1-6)GalNAcα1-OC$_3$H$_6$NH-PAA and derivatives of GalNAcα1-OC$_3$H$_6$NH-PAA, Neu$_5$A cα2-3Galβ1-3GalNAcα1-OC$_3$H$_6$NH-PAA, Galβ1-3(Neu5Acα2-6)-GalNAcα1-OC$_3$H$_6$NH-PAA, GlcNAcβ1-2Galβ1-3GalNAcα1-OC$_3$H$_6$NH-PAA, GlcNAcα1-3Galβ1-3GalNAcα1-OC$_3$H$_6$NH-PAA, GalNAc1-3Galβ1-OC$_3$H$_6$NH-PAA and 3'-O-Su-Galβ1-3GalNAcα1-OC$_3$H$_6$NH-PAA.

Using the respective stock solutions (1 mg in 1 ml of bidist. H$_2$O) stored in portions at −20° C., a dilution of 5 μg/ml in PBS was produced. 50 μl/well of the above was pipetted in a microtiter plate (NUNCLON-TC Microwell 96 F), and the test plate was incubated at 37° C. for 1 hour and at 4° C. overnight. On the next day, the test plate was washed 3 times with PBS/0.2% Tween. Subsequently, non-specific binding sites were blocked with 2% BSA in PBS, and 50 μl of the first antibody was applied (chimeric IgG and IgM, respectively: 0.1 μg/ml, purified, in PBS/0.1% BSA or undiluted culture supernatant of producing CHOdhfr-cells; multibodies: 10 μg/ml in PBS/0.1% BSA). After three wash steps with PBS/0.2% TWEEN, the corresponding secondary antibodies, peroxidase-coupled, were employed (an anti-mouse or anti-human Fcγ1 or μ antibody for complete antibodies, an anti-His-tag antibody for multibodies) to detect the specifically bound antibody constructs. To detect the bound secondary antibody, a color reaction with TMB (3,3',5,5'-tetramethylbenzidine) was performed. After 15 minutes the reaction was quenched by adding 2.5 N H$_2$SO$_4$. Measurement was performed using a microtiter plate photometer with 450 nm filter in dual mode versus 630 nm reference filter.

Figure 5:
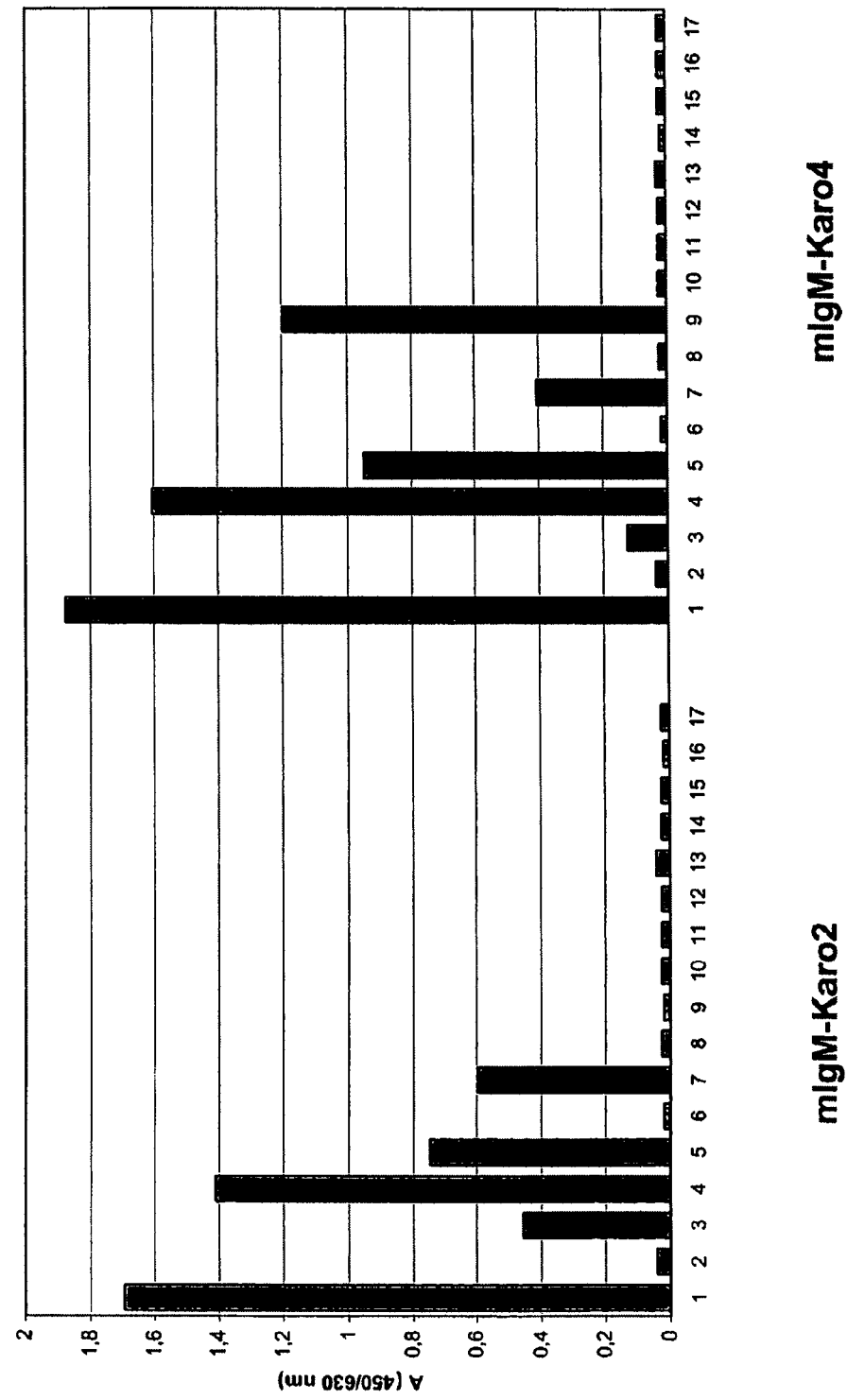
Figure 6:
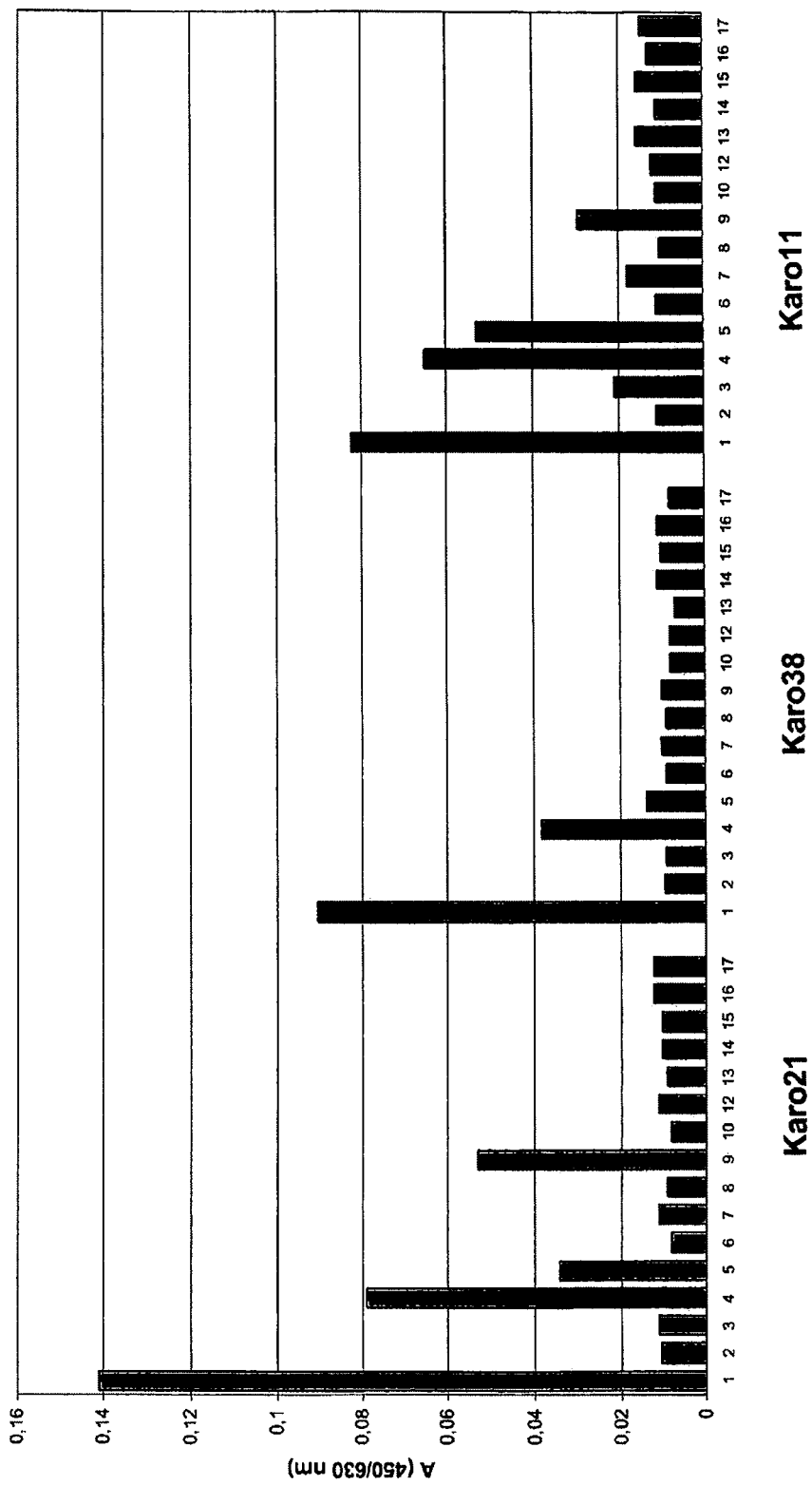
Figure 7B:
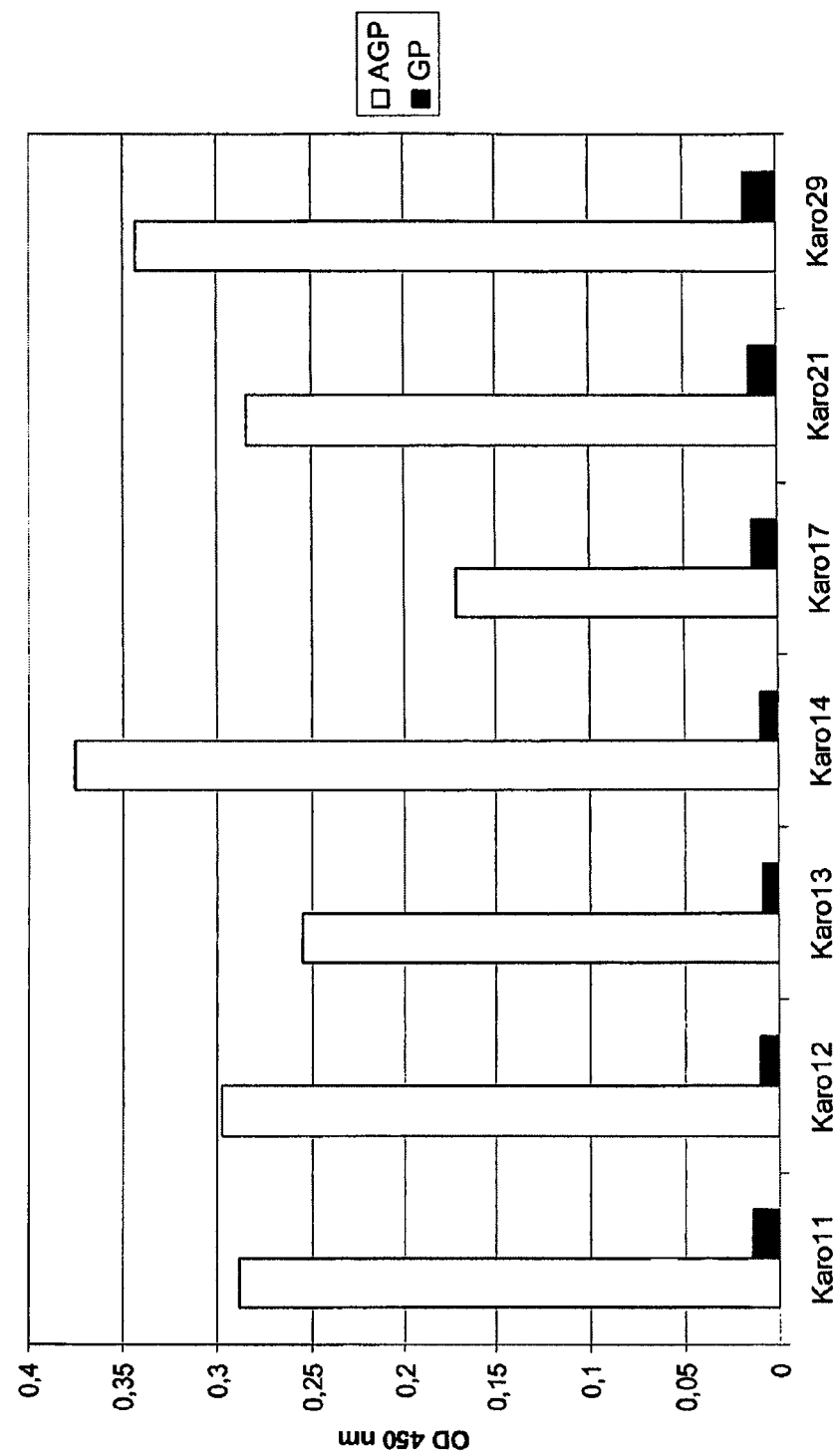
Figure 7C:
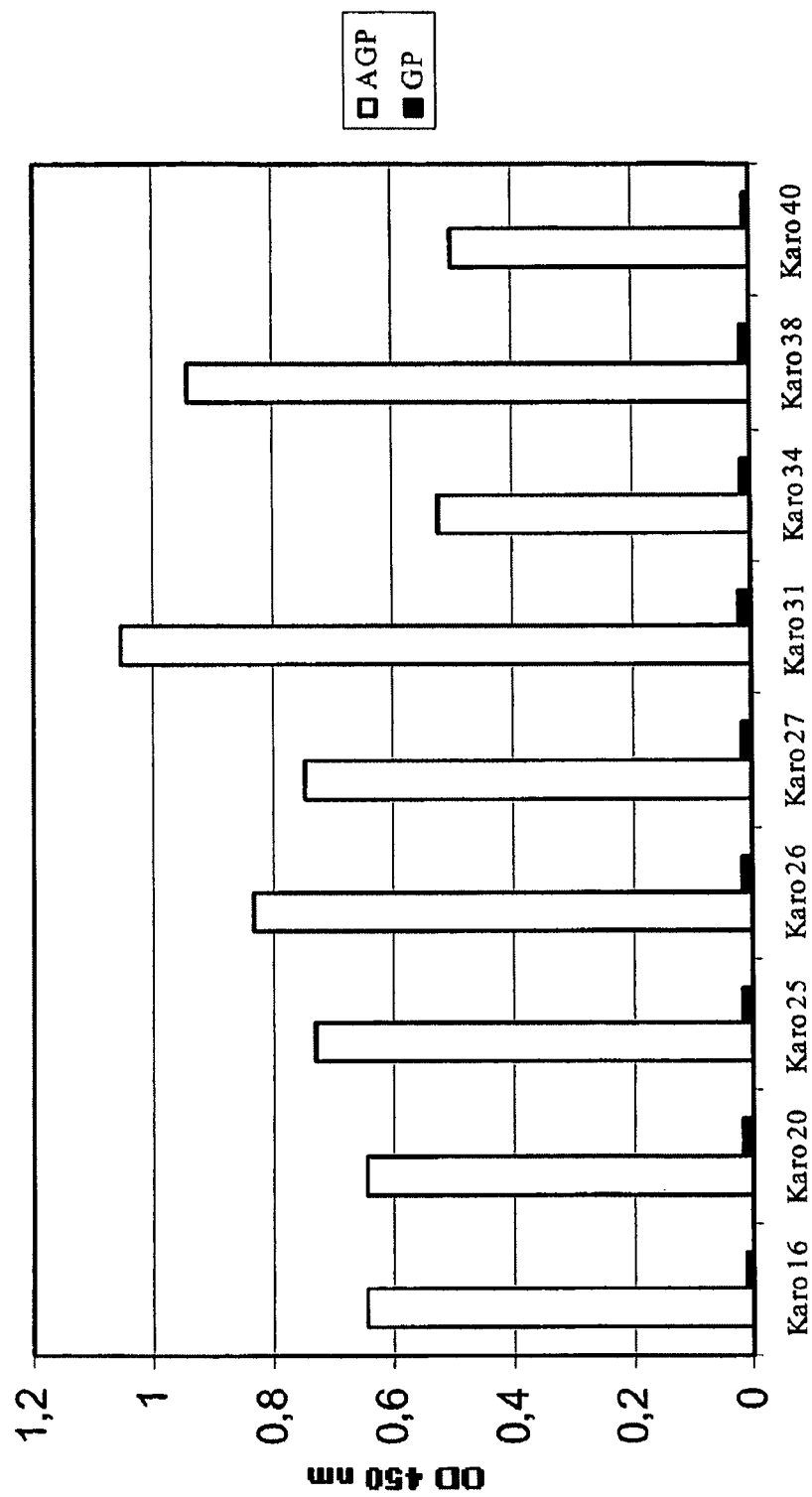
Figure 7D:
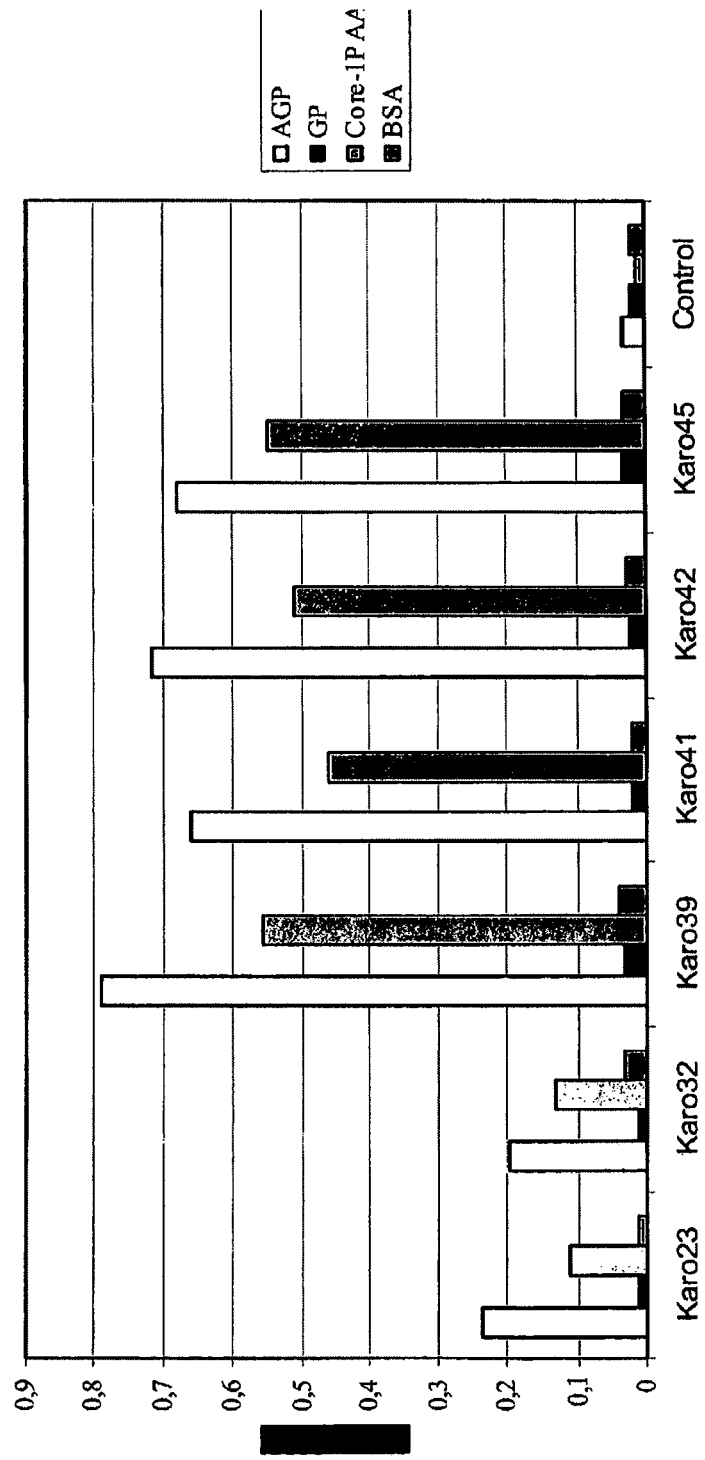
Figure 7E:
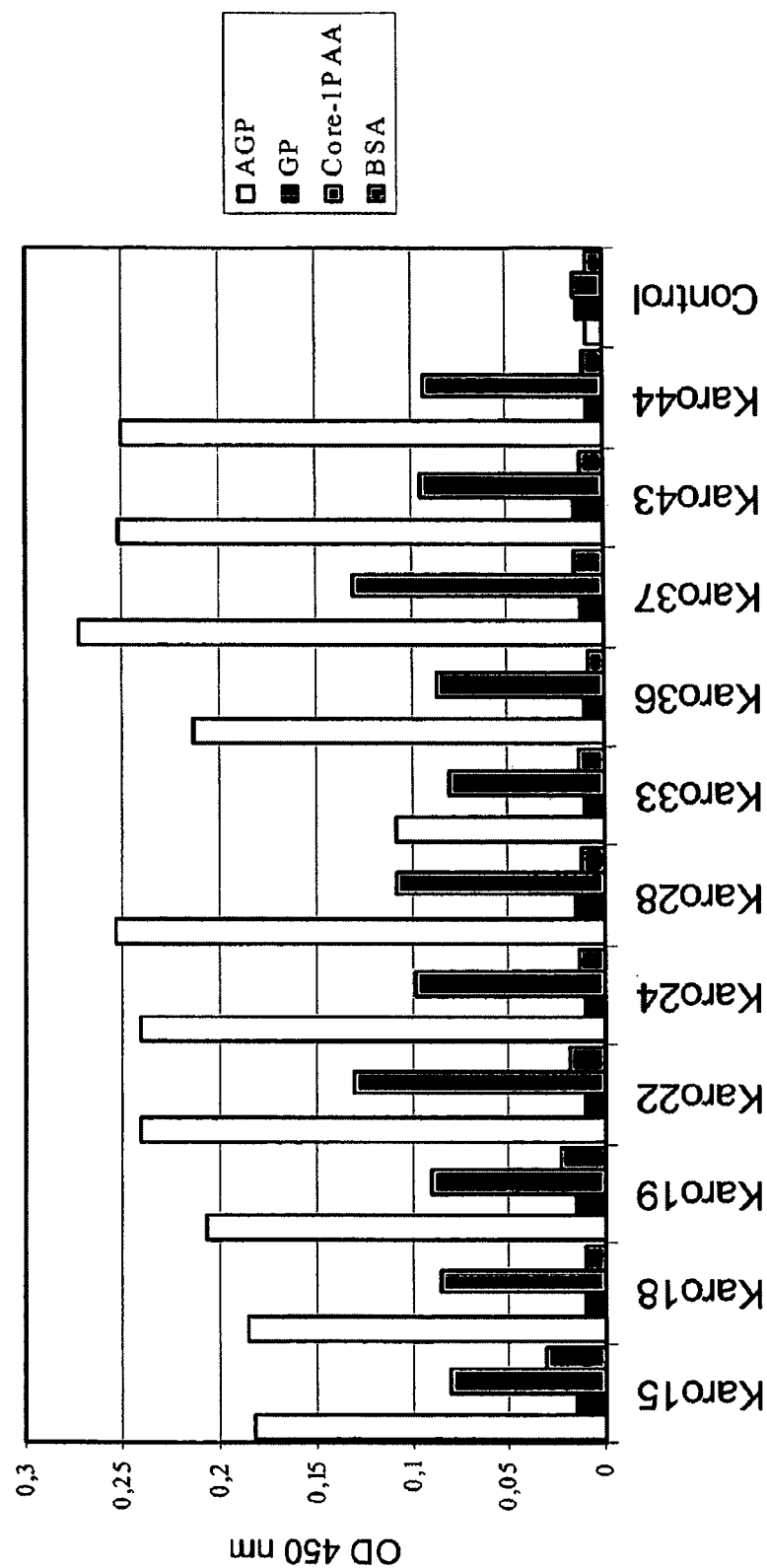

Representative results are illustrated in FIGS. 5 and 6. In FIG. 5, two recognition molecules with varying loop sequences in IgM format are compared. The antibody constructs mIgM-Karo2 (SEQ ID NO. 107 and SEQ ID NO. 109) and mIgM-Karo4 (SEQ ID NO. 108 and SEQ ID NO. 110) bind to the core 1 antigen in a highly specific fashion, preferably to the α-anomer, Galβ1-3GalNAcα, and more weakly to the β-anomer, Galβ1-3GalNAcβ. It is also possible that the recognition molecules of the invention bind the α-anomer Galβ1-3GalNAcα only, or both anomers Galβ1-3GalNAcα and Galβ1-3GalNAcβ in the same way. In addition, mIgM-Karo4 binds the core 2 structure Galβ1-3(GlcNAcβ1-6)GalNAcα. None of the other tested carbohydrate structures, not even structurally closely related structures, are recognized by the binding proteins claimed herein. Being a core 1-bearing glycoprotein, AGP shows a strong signal with both variants, and the asialofetuin glycoprotein—likewise bearing core 1—reacts significantly stronger with the Karo2 variant, this very likely being related to the different core 1 density in the two proteins. FIG. 6 shows the specificity pattern of the humanized recognition molecules, selected in an exemplary fashion, Karo11 (SEQ ID NO. 56 and SEQ ID NO. 90), Karo21 (SEQ ID NO. 59 and SEQ ID NO. 90) and Karo38 (SEQ ID NO. 69 and SEQ ID NO. 90) with varying framework sequences in scFv format and with one amino acid as linker. In this case as well, the same specificity pattern is seen, as described in the definition of core 1-specific binding in the meaning of the invention (see above).

Specific binding of various preferred formats and combinations in ELISA, exemplified on AGP, GP and/or Galβ1-3GalNAcα1-OC$_3$H$_6$NH-PAA, is illustrated in FIGS. 7a through e.

8. Immunohistologic and Immunocytologic Staining

For immunohistologic staining, frozen sections of appropriate tissue samples were air-dried and fixed with 10% formaldehyde in PBS for 15 min. To reduce the endogenic peroxidase activity, the sections were treated with 3% hydrogen peroxide in PBS and, following blocking of non-specific binding sites with pre-absorbed rabbit serum on neuraminidase-treated erythrocytes, incubated with a core 1-specific primary antibody. Subsequently, the preparations were incubated with an appropriate secondary antibody (anti-mouse or anti-human IgG or IgM, POD-coupled). The staining reaction was performed using the peroxidase substrate diaminobenzidine, and counter-staining with hematoxylin.

The exemplary recognition molecule mIgM-Karo4 according to the invention undergoes reaction with only a very small number of structures in normal tissue. However, said structures are located in areas inaccessible to an antibody (Table 3).

TABLE 3

| Reaction of human normal tissue with the core 1-specific mIgM-Karo4 antibody | |
|---|---|
| Type of tissue | Reactivity |
| Epidermis - basal membrane | negative |
| Stomach | |
| Foveola epithelium | negative |
| Fundic glands | negative |
| Corpus glands | negative |
| Colon mucosa | negative |
| Spleen | |
| Splenic trabeculae | negative |
| Reticular cells | negative |
| Lymphocytes | negative |
| Endothelium | negative |
| Prostate | negative |
| Liver | |
| Hepatocytes | negative |
| Kupffer cells | negative |
| Bile tract | negative |
| Lymphatic nodes | |
| Lymphocytes | negative |
| Reticular cells | negative |
| Gall bladder | negative |
| Adrenal gland | |
| Adrenal cortex | negative |
| Adrenal medulla | negative |
| Bladder | negative |
| Heart | negative |
| Pancreas | |
| Glandular ducts | positive |
| Acini | negative |
| Islets of Langerhans | negative |

The recognition molecules as claimed give positive reaction with a variety of carcinomas. The data in table 4 show that core 1-specific recognition molecules recognize a high percentage of tumor patients of one indication, which differs from one indication to the other.

TABLE 4

Reaction of human tumor tissue with the core 1-specific mIgM-Karo4 antibody

| Type of tissue | Reactivity |
|---|---|
| Colon carcinoma | |
| Primary carcinoma | 31/52 |
| Liver metastases | 20/22 |
| Lung carcinoma | |
| Large cell | 3/8 |
| Bronchoalveolar | 1/1 |
| Adenocarcinoma | 6/6 |
| Bladder carcinoma | 5/9 |
| Stomach carcinoma | |
| Intestinal type | 8/8 |
| Diffuse type | 3/3 |
| Prostate carcinoma | 9/9 |
| Mammary carcinoma | |
| Intraductal/ductal | 8/10 |
| Slightly differentiated | 2/5 |
| Mucinous | 1/1 |
| Thyroid carcinoma | 0/10 |
| Adrenal carcinoma | |
| Clear cell | 4/9 |
| Transitional cell | 2/5 |
| Cervical carcinoma | 1/2 |
| Ovarian carcinoma | |
| Adenocarcinoma | 2/2 |
| Endometrioid | 2/2 |
| Teratoma | 2/2 |
| Glioblastoma | 0/3 |

Figure 8:
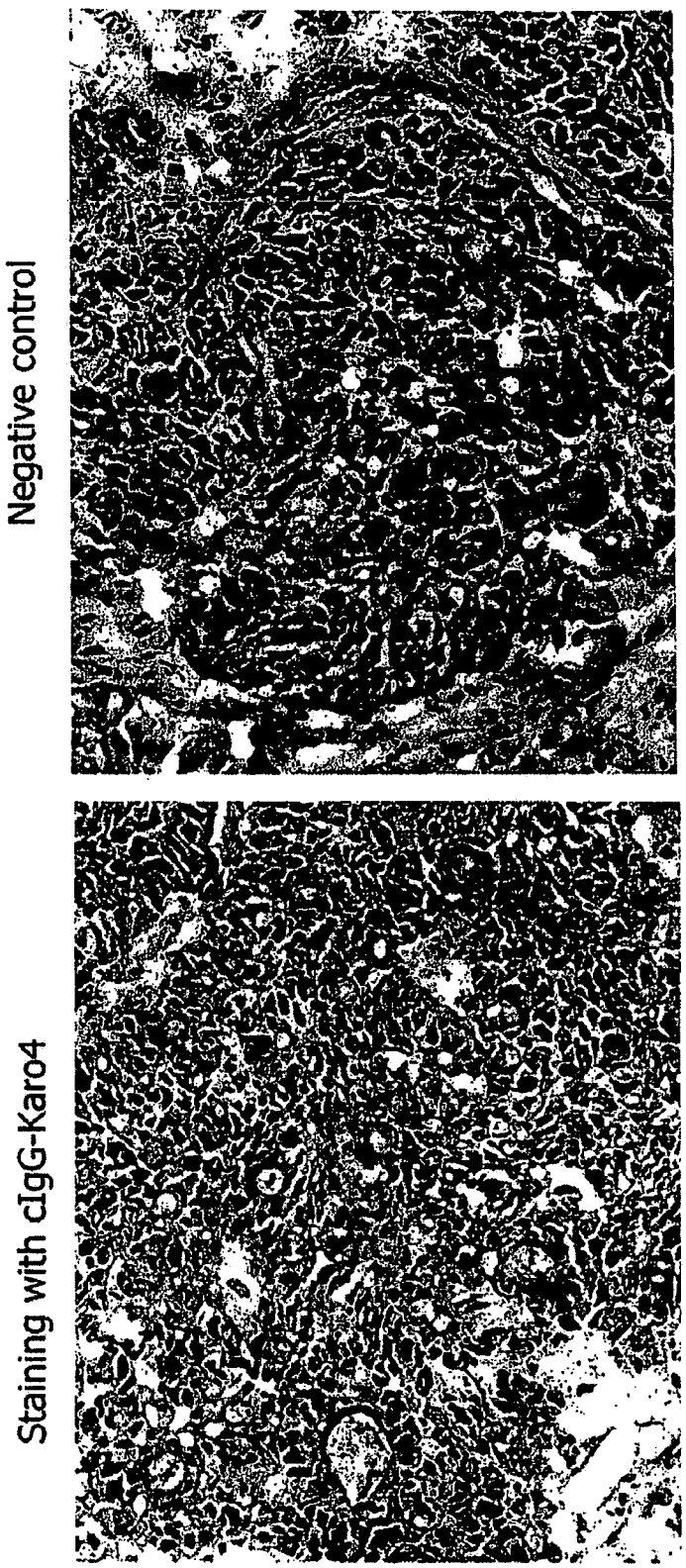

To develop a mouse tumor model, various xenotransplants were investigated. The xenotransplants were human colon carcinoma tissues repeatedly passaged on nude mice. In an exemplary fashion, FIG. 8 shows immunohistochemic staining of a xenotransplant preparation with the core 1-specific cIgG-Karo4 antibody.

Immunofluorescence was used for the immunocytologic stainings. To this end, appropriate cells were slightly dried on microscope slides and fixed with 5% formaldehyde for 10 min. Following blocking of non-specific binding sites with BSA (1% in PBS), the cells were incubated with the primary antibody. This was followed by washing 3 times with PBS and incubation with the appropriate fluorescence-labeled secondary antibody (anti-mouse or anti-human IgG or IgM for complete antibodies; anti-myc-tag or anti-His-tag antibodies for single-chain antibody fragments). After repeated washing with PBS, the cells were embedded in Mowiol.

Various cell lines were tested with core 1-specific recognition molecules in immunofluorescence. A number of tumor cell lines, as well as some leukemia cell lines gave positive reaction (Table 5 and FIG. 9).

TABLE 5

Reactivity of various cell lines with core 1-specific mIgM-Karo1 or mIgM-Karo4 antibodies

| Cell lines | Reactivity |
|---|---|
| KG-1 | positive |
| ZR-75-1 | positive |

TABLE 5-continued

Reactivity of various cell lines with core 1-specific mIgM-Karo1 or mIgM-Karo4 antibodies

| Cell lines | Reactivity |
|---|---|
| T47D | (positive) few cells |
| U266 | negative |
| LN78 | positive |
| HT29 | positive |
| HCT116 | negative |
| HepG2 | negative |
| K562 | negative |
| NM-D4 | positive |

Figure 9:

In an exemplary fashion, FIG. 9 shows fluorescence labeling of KG-1 cells, an acute myeloid leukemia cell line, with various antibody constructs, a murine IgM, and two scFv antibodies with different linker length (SEQ ID NO. 95 with 18 amino acids and SEQ ID NO. 104 with one amino acid as linker). All three constructs show specific staining of the tumor cell line, the monovalent antibody fragment SEQ ID NO. 95 showing the weakest signal.

9. Chelating and Radioactive Labeling of Antibodies and Antibody Fragments

Using conjugation, a chelating agent allowing binding of a radioactive metal was covalently bound to the cIgG-Karo4 antibody and to the multibody of sequence SEQ ID NO. 104, respectively. Commercial products from Macrocyclics (Dallas, USA), p-isothiocyanatobenzyl-diethylenetriaminepentaacetic acid (p-SCN-Bz-DTPA) and p-isothiocyanatobenzyl-1,4,7,10-tetraazacyclododecane-1,4,7,10-tetraacetic acid (p-SCN-Bz-DOTA) were employed as chelating agents. Both chelating agents are suitable for linking to antibodies for radiolabeling thereof [Brechbiel et al., 1986; Kozak et al., 1989; Stimmel et al., 1995].

Conjugation proceeds via reaction of the isothiocyanate group in the chelating agent with a free $\epsilon$-amino group of the amino acid lysine on the antibody, thus forming a covalent N—C bond between chelating agent and antibody.

Initially, the purified antibody or the purified antibody fragment must be re-buffered in coupling buffer, pH 8.7. To this end, ultrafiltration in a filtration cartridge (Centriprep of YM50 (Amicon)) was performed. This was done by repeated dilution with a 10 fold volume and filtration through a membrane of defined pore size using centrifugation. In this way, PBS was replaced by alkaline coupling buffer (0.05 M sodium carbonate, 0.15 M sodium chloride, pH 8.7).

Chelating was performed using the bifunctional chelating agents p-SCN-Bz-DTPA and p-SCN-Bz-DOTA, respectively. For the chelating reaction, the protein (1 to 10 mg/ml) in coupling buffer and a solution of chelating agent of 1 mg/ml in 2% DMSO/water were mixed such that a molar excess of chelating agent was ensured. This was followed by incubation of the mixture at 37° C. for 1 hour. Subsequently, non-bound chelating agent was removed by ultrafiltration in the same vessel (Centriprep YM50 (Amicon)) and, as described above, this was re-buffered to pH 4.2 in a loading buffer (0.15 M sodium acetate, 0.15 M sodium chloride, pH 4.2) required for radioactive labeling. The protein concentration during and after this step was re-adjusted to 1-10 mg/ml using UV measurement at 280 nm.

Conditions for the chelating reaction had to be found, which would allow radiolabeling of the antibody without substantially reducing the bioactivity thereof.

The chelated antibody was loaded with a radioactive metal, thereby producing the radioantibody. The isotopes $^{111}$indium and $^{90}$yttrium were used for loading. Both have comparable chemical and physicochemical properties, being bound as trivalent ions ($^{111}$In$^{3+}$, $^{90}$Y$^{3+}$) by the chelating agent. The antibody labeled with $^{111}$indium is a γ-emitter and is used clinically to find the individual dose for a patient, while $^{90}$yttrium is a β-emitter which is used therapeutically. The half-lives are 67 hours for $^{111}$In and 64 hours for $^{90}$Y.

$^{111}$Indium chloride from the company NEN (Perkin Elmer, Belgium) was used for loading. The radioactive metal is supplied in a solution of hydrochloric acid. First of all, the $^{111}$InCl$_3$ solution was brought to an HCl concentration of 1 M. Subsequently, this was diluted with 0.05 M HCl to a specific activity of 80-320 mCi/ml, and an aliquot thereof was used for incorporation in the chelated antibody, in which case the added volume of HCl-acidic $^{111}$InCl$_3$ solution should be equal to the volume of antibody solution supplied in the coupling buffer of pH 4.2 so as to ensure pH stability. The incubation time was 1 hour at 37° C., with occasional careful mixing.

Subsequently, the filter insert was re-inserted into the filtration cartridge and re-buffered as described above in phosphate buffer, pH 7.2, including a physiological content of sodium chloride, thereby effecting separation of high-molecular weight radiolabeled antibody and unbound $^{111}$InCl$_3$. Quantification of $^{111}$In incorporation in the chelated antibody was performed using thin layer chromatography. The incorporation rate of radioactive metal was 70-99% of the radioactivity employed.

10. Detection of Core 1-Positive, Secretory MUC1 in a Sandwich ELISA

Core 1-positive, secretory MUC1 can be detected in a sandwich ELISA. A MUC1-specific antibody was used as scavenger antibody of MUC1, and a core 1-specific antibody to detect the core 1 antigen. A third enzyme- or fluorescence-coupled antibody must be used to detect the secondary antibody.

The supernatants of two tumor cell lines (K562 and T47D) were analyzed as examples. The results are illustrated in Table 6. 10$^5$ cells per ml of cell culture medium were seeded, cultured for 4 days without replacing the medium, an aliquot was subsequently drawn, and the cell culture supernatant was separated from the cell pellet by centrifugation. 50 μl of undiluted supernatants were used in the ELISA. The anti-MUC1-anti-core 1 sandwich ELISA was carried out by coating the microtiter plate with scavenger antibody (1 μg/ml) in PBS at 4° C. overnight. Three different concentrations of antibody were used for coating (1 μg/ml, 2 μg/ml and 4 μg/ml). The 1 μg/ml coating was found to be the most sensitive in the sandwich ELISA. Subsequently, the coated plates were washed twice with PBS and blocked in 5% BSA, 0.05% TWEEN 20 in PBS for 1.5 hours at room temperature. The blocking buffer was removed, the plates were washed once more with 0.1% TWEEN 20 in PBS (washing buffer), the samples were added and incubated at room temperature for 1.5 hours. Cell culture medium or 2% BSA in washing buffer (dilution buffer for secondary antibody) was used as negative control. Positive control was not available. After washing three times, neuraminidase treatment was performed in the wells intended for that purpose. To this end, a neuraminidase solution (DADE Behring, Germany) was diluted 1:5 in imidazole buffer (0.68 g of imidazole, 0.19 g of CaCl$_2$ and 0.4 g of NaCl in 100 ml of H$_2$O, pH 6.8) and incubated at 50 μl/well for 30 min at 37° C. As a control, the imidazole buffer with no neuraminidase solution was incubated in a corresponding well. Subsequently, the wells were washed three times, and the mIgM-Karo4 antibody for the detection of core 1 antigen was added at a dilution of 1:500 in 2% BSA in washing buffer and incubated at room temperature for another hour. Again, this was washed three times, followed by addition of a peroxidase-coupled anti-mouse IgM(μ) antibody (Dianova) diluted 1:5000 in 2% BSA washing buffer and incubation for 1 hour at room temperature. Finally, the plates were washed twice in washing buffer and once in PBS. The staining reaction was performed in 25 mM citric acid, phosphate buffer, pH 5.0, with 0.04% H$_2$O$_2$ and 0.4 mg/ml o-phenylenediamine (Sigma) in the dark at room temperature. The staining reaction was quenched by adding 2.5 N sulfuric acid (final concentration 0.07 N) and measured in an ELISA Reader at 492 nm with a 620 nm reference filter.

TABLE 6

Analysis of core 1-positive MUC1 in culture supernatants of two cell lines with and with no neuraminidase treatment in a sandwich ELISA

| Cell line | Signal | |
|---|---|---|
| | −NeuAcdase | +NeuAcdase |
| K562 | − | + |
| T47D | + | +++ |

11. Effective Binding of Radiolabeled Core 1-Specific Recognition Molecules in Tumor Cells The core 1-positive tumor cell line NM-D4 [DSMZ deposit No. DSM ACC2605] (cf. Table 5) was used to test the binding capability of radiolabeled recognition molecules in core 1-positive tumor cells. In each double determination, a defined number of cells was placed in a 1.5 ml vessel and incubated with increasing amounts of antibodies. Following washing, the amount of bound antibodies was determined on the basis of the counting rate.

2×10$^6$ cells per batch are required. Following pre-incubation of the cells for one hour on ice, the required amount of cells was placed in reaction vessels, centrifuged (5 min at 1000×g, 25° C.), and the supernatant was removed. Thereafter, this was filled up with PBS/0.1% Tween20/1% BSA to make a volume of 200 μl, subtracting the amount of recognition molecules to be added later. Subsequently, the corresponding $^{111}$In-labeled recognition molecule (see Example 9) was added to make a final volume of 200 μl (about 0.5 to 20 μg, depending on the recognition molecule), and the batch was incubated for one hour at 4-8° C. Following centrifugation (4 min, 1000×g, 25° C.), the supernatant was removed and the cell pellet carefully resuspended in 400 μl of PBST/1% BSA. After another wash, the cell pellet was measured in the vessel on a gamma counter. The specific counting rates were determined in the initial solutions of defined concentration, and the value in cpm/ng was used as a basis of relativizing the measured values of bound antibody. Free binding is obtained from the difference of total amount and amount of bound antibody. These values were plotted in a diagram as ratio of bound/non-bound versus bound amount, the slope in the linear region of the curve was determined, and the abscissa intersection was determined (Scatchard analysis). The abscissa intersection indicates the number of binding sites/cell. The slope of the straight line furnishes the association constant $K_{ass}$ in M$^{-1}$.

Figure 10:
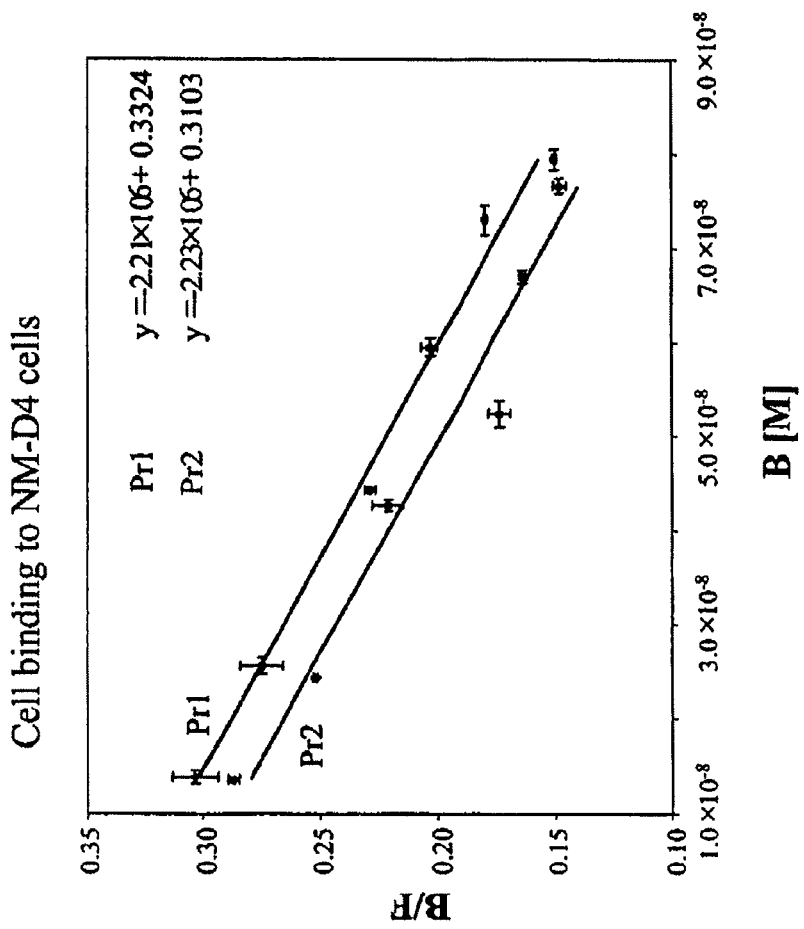

FIG. 10 exemplifies the Scatchard analysis of binding of radiolabeled recognition molecules in scFv format with the sequence SEQ ID NO. 104 and with one amino acid as linker on NM-D4 cells (two different preparations).

Table 7 summarizes the association constants and the number of cell binding sites of different core 1-specific multibodies on NM-D4 cells.

TABLE 7

Cell binding test and Scatchard analysis with
$^{111}$In-labeled recognition molecules on NM-D4 cells.

| Antibody | $K_{ass}$ [M$^{-1}$] | Number of binding sites/cell |
|---|---|---|
| SEQ ID NO. 105 | $1.1 \times 10^7$ | $4.8 \times 10^6$ |
| SEQ ID NO. 104 | $2.1 \times 10^6$ | $8.1 \times 10^6$ |
| SEQ ID NO. 103 | $1.2 \times 10^6$ | $9.2 \times 10^6$ |

12. Accumulation of Radiolabeled Core 1-Specific Recognition Molecules on Core 1-Positive Tumors in an In Vivo Tumor Model ZR-75-1 cells as tumor model were injected subcutaneously in nude mice (Ncr: nu/nu, female). After about 3-4 weeks, the tumor is palpable under the skin. To the tumor-bearing mice (n=4 per point in time) 5 µg of $^{111}$In-labeled multibody (SEQ ID NO. 104 and SEQ ID NO. 105, respectively) in 200 µl was administered into the tail vein. After 24 hours the mice were sacrificed and the radioactivity distribution in the tumor, in serum and in organs was determined. Table 8 shows the specific high accumulation of multibodies in the tumor (in % ID/g tumor, relative to injected dose and tumor weight) compared to serum and organs.

TABLE 8

Biodistribution of $^{111}$In-labeled recognition
molecules in tumor-bearing mice

| | SEQ ID NO. 104 | SEQ ID NO. 105 |
|---|---|---|
| Serum (% ID/ml) | 1.4 ± 0.16 | 1.0 ± 0.24 |
| Tumor (% ID/g) | 10.8 ± 2.88 | 8.1 ± 1.45 |
| Liver (% ID/g) | 3.7 ± 0.15 | 5.3 ± 0.92 |
| Lung (% ID/g) | 1.7 ± 0.11 | 1.9 ± 0.19 |
| Heart (% ID/g) | 1.5 ± 0.06 | 1.9 ± 0.19 |
| Spleen (% ID/g) | 5.4 ± 0.75 | 6.7 ± 1.07 |
| Brain (% ID/g) | 0.1 ± 0.01 | 0.1 ± 0.00 |
| Bone marrow (% ID/g) | 1.0 ± 0.16 | 1.7 ± 0.90 |

13. Therapeutical Study for Reduction of Core 1-Positive Tumors with Radiolabeled Core 1-Specific Recognition Molecules in an In Vivo Tumor Model The therapeutical studies were carried out using the same established ZR-75-1 tumor model as described in the biodistribution studies (see Example 12). To this end, the chelated recognition molecules (see Example 9) were loaded (pH 4.5, 37° C., 30 min; cf. $^{111}$indium incorporation) with $^{90}$yttrium (a β-emitter to destroy the tumor cells), and the stability was controlled using thin layer chromatography. The tumor-bearing mice (about three weeks after subcutaneous injection of ZR-75-1 cells) were given 200 µl into the tail vein. The injection solution included the $^{90}$Y-labeled multibody (up to a maximum of 100 µCi per dose) in Ca/Mg-PBS with 0.2 to 4% fetal calf serum to protect against radiolysis. Control groups received the same injection with no radioactively labeled recognition molecule. Body weight and tumor size were measured twice a week and compared. The relative tumor growth was determined considering the respective tumor size at the beginning of treatment. A second injection was given three weeks after the first treatment. Significant reduction in tumor growth compared to the control group was possible by suitable treatment.

FIGURE LEGENDS

FIG. 1a: Sequences of linkers in various multibody single-chain antibody fragments (SEQ ID NOS: 114-135, respectively, in order of appearance).

FIG. 1b: Cloning diagram for the preparation of single-chain antibody fragments having different linker length (6 His tag is disclosed as SEQ ID NO: 136).

FIG. 2: Vector for cloning and bacterial expression of single-chain antibody fragments.

FIG. 3: Analysis of multibodies in scFv format with varying linker length in ELISA.

Multibodies having the amino acid sequences SEQ ID Nos. 95, 96, 97, 98, 99, 100, 101, 103, 104 and 105 were expressed in E. coli as described above and the periplasm fractions obtained. Asialoglycophorin, which is a core 1-bearing glycoprotein, was used as antigen in the ELISA. Step-by-step linker length reduction results in increased binding to asialoglycophorin. The best binding properties are seen in the variants having SEQ ID Nos. 104 and 105. These multivalent constructs in dia/triabody format are preferred embodiments of the invention.

FIG. 4: Vector system for cloning and eukaryotic expression of chimeric antibodies in IgG1 or IgM format. The figure discloses SEQ ID NOS: 137-142, respectively, in order of appearance.

FIG. 5 and FIG. 6: Specificity analysis in ELISA.

Various glycoproteins and carbohydrate-PAA conjugates were used as antigens. Asialoglycophorin [1]; glycophorin [2]; asialofetuins [3]; Galβ1-3GalNAcα1-OC$_3$H$_6$NH-PAA [4]; Galβ1-3GalNAcα1-p-OC$_6$H$_4$NH-PAA [5]; Galα1-3GalNAcα1-OC$_3$H$_6$NH-PAA [6]; Galβ1-3GalNAcβ1-OC$_3$H$_6$NH-PAA [7]; Galα1-3GalNAcβ1-OC$_3$H$_6$NH-PAA [8]; Galβ1-3(GlcNAcβ1-6)GalNAcα1-OC$_3$H$_6$NH-PAA [9]; GalNAcα1-OC$_3$H$_6$NH-PAA [10]; Neu5Acα2-3Galβ1-3GalNAcα1-OC$_3$H$_6$NH-PAA [11]; Galβ1-3(Neu5Acα2-6)GalNAcα1-OC$_3$H$_6$NH-PAA [12]; GlcNAcβ1-2Galβ1-3GalNAcα1-OC$_3$H$_6$NH-PAA [13]; GlcNAcα1-3Galβ1-3GalNAcα1-OC$_3$H$_6$NH-PAA [14]; GalNAcα1-3Galβ1-OC$_3$H$_6$NH-PAA [15]; and 3'-O-Su-Galβ1-3GalNAcα1-OC$_3$H$_6$NH-PAA [16]. BSA [17] was used as control. In FIG. 5, two antibodies in IgM format with varying CDR sequence composition were used. FIG. 6 shows the specificity pattern of three humanized recognition molecules in scFv format with varying framework sequences.

FIG. 7a-7e: Specific binding of different preferred formats and combinations of recognition molecules of the invention in ELISA, with AGP, GP and/or core 1-PAA (Galβ1-3GalNAcα1-OC$_3$H$_6$NH-PAA) antigens as examples.

FIG. 8: Immunohistochemical staining of xenotransplant preparations.

Human colon carcinoma tissue was transplanted on nude mice and passaged after reaching a specific size. The tumor tissue was embedded and dissected and used in immunohistochemical staining. In a) the tissue was labeled with cIgG-Karo4 as primary antibody and an anti-human Fcγ antibody, POD-coupled, as secondary antibody. Brown staining characterizes core 1-positive structures.

FIG. 9: Fluorescence-labeling of cells of the KG-1 tumor cell line with different core 1-specific recognition molecules.

FIG. 10: Scatchard diagram for analysis of cell binding of radiolabeled core 1-specific recognition molecules. Binding data of multibody SEQ ID NO. 104 with a linker length of one amino acid are illustrated in an exemplary fashion (Pr1 and Pr2 correspond to two different preparations). B: amount bound to cells [M]; F: free binding as difference of total and bound amount of antibody [M]. The corresponding straight-line equation is given at the top, the slope of the straight-line representing the association constant.

| SEQUENCE INFORMATION |
| --- |
| CDR Sequences |

| SEQ ID NO. 1 | NYWLG |
| --- | --- |
| SEQ ID NO. 2 | DIYPGGGYTNYNEKFKG |
| SEQ ID NO. 3 | DIYPGGSYTNYNEKFKG |
| SEQ ID NO. 4 | YDAAGPWFAY |
| SEQ ID NO. 5 | YDAAGPGFAY |
| SEQ ID NO. 6 | YDNHYFDY |
| SEQ ID NO. 7 | RSSQSIVHSNGNTYLE |
| SEQ ID NO. 8 | RSSQSLLHSNGNTYLH |
| SEQ ID NO. 9 | KSSQSLLHSDGKTYLY |
| SEQ ID NO. 10 | KVSNRFS |
| SEQ ID NO. 11 | EVSSRFS |
| SEQ ID NO. 12 | FQGSHVPYT |
| SEQ ID NO. 13 | SQSTHVPYT |

| CDR Sequences (canonical structure variants) |

| SEQ ID NO. 14 | NYWIG |
| --- | --- |
| SEQ ID NO. 15 | NYWMG |
| SEQ ID NO. 16 | NYWWG |
| SEQ ID NO. 17 | NYWVG |
| SEQ ID NO. 18 | DIYPGGDYTNYNEKFKG |
| SEQ ID NO. 19 | DIYPGGNYTNYNEKFKG |
| SEQ ID NO. 20 | DIYTGGGYTNYNEKFKG |
| SEQ ID NO. 21 | DIYTGGDYTNYNEKFKG |
| SEQ ID NO. 22 | DIYTGGNYTNYNEKFKG |
| SEQ ID NO. 23 | DIYTGGSYTNYNEKFKG |
| SEQ ID NO. 24 | DIYAGGGYTNYNEKFKG |
| SEQ ID NO. 25 | DIYAGGDYTNYNEKFKG |
| SEQ ID NO. 26 | DIYAGGNYTNYNEKFKG |
| SEQ ID NO. 27 | DIYAGGSYTNYNEKFKG |
| SEQ ID NO. 28 | RPSQSIVHSNGNTYLE |
| SEQ ID NO. 29 | RSSQSLVHSNGNTYLE |
| SEQ ID NO. 30 | RSSQSIVHSNGNTYFE |
| SEQ ID NO. 31 | RPSQSLVHSNGNTYLE |
| SEQ ID NO. 32 | RPSQSIVHSNGNTYFE |
| SEQ ID NO. 33 | RSSQSLVHSNGNTYFE |
| SEQ ID NO. 34 | RPSQSLLHSNGNTYLH |
| SEQ ID NO. 35 | RSSQSILHSNGNTYLH |
| SEQ ID NO. 36 | RSSQSLLHSNGNTYFH |
| SEQ ID NO. 37 | RPSQSILHSNGNTYLH |
| SEQ ID NO. 38 | RPSQSLLHSNGNTYFH |
| SEQ ID NO. 39 | RSSQSILHSNGNTYFH |
| SEQ ID NO. 40 | KPSQSLLHSDGKTYLY |
| SEQ ID NO. 41 | KSSQSILHSDGKTYLY |
| SEQ ID NO. 42 | KSSQSLLHSDGKTYFY |
| SEQ ID NO. 43 | KPSQSILHSDGKTYLY |
| SEQ ID NO. 44 | KPSQSLLHSDGKTYFY |
| SEQ ID NO. 45 | KSSQSILHSDGKTYFY |

| Variable heavy chains VH |

SEQ ID NO. 46
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSS

SEQ ID NO. 47
QVQLKQSGAELVRPGTSVKISCKASGYTFTNYWLGWVKQRPGHGLEWIGDIYPGGSYTNYN
EKFKGKATLTADTSSSTAYMQLSSLTSEDSAVYFCARYDNHYFDYWGQGTTLTVSS

SEQ ID NO. 48
QVQLKQSGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTTLTVSS

SEQ ID NO. 49
EVKLVESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTSVTVSS

SEQ ID NO. 50
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTTVTVSS

SEQ ID NO. 51
EVKLVESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTTVTVSS

SEQ ID NO. 52
QVQLKQSGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTLVTVSA

SEQ ID NO. 53
QVQLKQSGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTTVTVSS

| SEQUENCE INFORMATION |
| --- |

SEQ ID NO. 54
QVTLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTSVTVSS

SEQ ID NO. 55
QVQLKQSGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTSVTVSS

SEQ ID NO. 56
QVQLVQSGAEVKKPGASVKVSCKASGYTFTNYWLGWVRQAPGQGLEWIGDIYPGGGYTNYN
EKFKGKATLTADTSSSTAYMQLSSLTSEDSAVYFCAYYDAAGPWFAYWGQGTLVTVSS

SEQ ID NO. 57
QVQLVQSGAEVKKPGASVKVSCKASGYTFTNYWLGWVRQAPGQGLEWIGDIYPGGGYTNYN
EKFKGKATLTADTSSSTAYMQLSSLTSEDSAVYYCAYYDAAGPWFAYWGQGTLVTVSS

SEQ ID NO. 58
QVQLVQSGAEVKKPGASVKVSCKASGYTFTNYWLGWVRQAPGQGLEWIGDIYPGGGYTNYN
EKFKGKATLTADTSSSTAYMQLSRLTSEDSAVYFCAYYDAAGPWFAYWGQGTLVTVSS

SEQ ID NO. 59
QVQLVQSGAEVKKPGASVKVSCKASGYTFTNYWLGWVRQAPGQGLEWIGDIYPGGGYTNYN
EKFKGKATLTADTSSSTAYMELSSLTSEDSAVYFCAYYDAAGPWFAYWGQGTLVTVSS

SEQ ID NO. 60
QVQLVQSGAEVKKPGASVKVSCKASGYTFTNYWLGWVKQRPGQGLERIGDIYPGGGYTNYN
EKFKGKATLTADTSSSTAYMQLSSLTSEDSAVYFCAYYDAAGPWFAYWGQGTLVTVSS

SEQ ID NO. 61
QVQLVQSGAEVKKPGASVKVSCKASGYTFTNYWLGWVKQRPGQGLEWIGDIYPGGGYTNYN
EKFKGKATLTADTSSSTAYMQLSSLTSEDSAVYFCAYYDAAGPWFAYWGQGTLVTVSS

SEQ ID NO. 62
QVQLVQSGAEVKKPGASVKVSCKASGYTFTNYWLGWVRQAPGQGLEWIGDIYPGGGYTNYN
EKFKGKATLTADTSTSTAYMELSSLTSEDSAVYFCAYYDAAGPWFAYWGQGTTVTVSS

SEQ ID NO. 63
QVQLVQSGAEVKKPGASVKVSCKASGYTFTNYWLGWVRQAPGQGLEWIGDIYPGGGYTNYN
EKFKGKATLTADTSTSTAYMELSSLRSEDSAVYFCAYYDAAGPWFAYWGQGTLVTVSS

SEQ ID NO. 64
QVQLVQSGAEVKKPGASVKVSCKASGYTFTNYWLGWVRQAPGQGLEWIGDIYPGGGYTNYN
EKFKGKATLTADTSTSTAYMELSSLTSEDSAVYYCAYYDAAGPWFAYWGQGTLVTVSS

SEQ ID NO. 65
QVQLVQSGAEVKKPGASVKVSCKASGYTFTNYWLGWVKQRPGQGLEWIGDIYPGGGYTNYN
EKFKGKATLTADTSTSTAYMELSSLRSEDTAVYFCAYYDAAGPWFAYWGQGTLVTVSS

SEQ ID NO. 66
QVQLVQSGAEVKKPGASVKVSCKASGYTFTNYWLGWVKQRPGQGLEWIGDIYPGGGYTNYN
EKFKGKATLTADTSTSTAYMELSSLRSEDTAVYYCAYYDAAGPWFAYWGQGTTVTVSS

SEQ ID NO. 67
QVQLVQSGAEVKKPGASVKVPCKASGYTFTNYWLGVWKQRPGQGLEWIGDIYPGGGYTNYN
EKFKGKATLTADTSTSTAYMELSSLRSEDTAVYYCAYYDAAGPWFAYWGQGTLVTVSS

SEQ ID NO. 68
QVQLVQSGAEVKKPGASVKVSCKASGYTFTNYWLGWVKQRPGQGLEWIGDIYPGGGYTNYN
EKFKGKATLTADTSTSTAYMELSSLRSEDTAVYYCAYYDAAGPWFAYWGQGTLVTVSS

SEQ ID NO. 69
QVQLVQSGAEVKKPGASVKVSCKASGYTFTNYWLGWVRQAPGQGLEWIGDIYPGGGYTNYN
EKFKGKATLTADTSTSTAYMELSSLRSEDTAVYYCAYYDAAGPWFAYWGQGTLVTVSS

SEQ ID NO. 70
QVQLVQSGAEVKKPGASVKVSCKASGYTFTNYWLGWVRQAPGQGLEWIGDIYPGGGYTNYN
EKFKGKATLTADTSTSTAYMELSSLRSEDTAVYYCAYYDAAGPWFAYWGQGTTVTVSS

SEQ ID NO. 71
QVQLVQSGAEVKKPGASVKVSCKASGYTFTNYWLGWVKQRPGQGLEWIGDIYPGGGYTNYN
EKFKGKATLTADTSTSTAYMELSSLTSEDSAVYYCAYYDAAGPWFAYWGQGTTVTVSS

SEQ ID NO. 72
QVQLVQSGAEVKKPGASVKVSCKASGYTFTNYWLGWVKQRPGQGLEWIGDIYPGGGYTNYN
EKFKGKATLTADTSTSTAYMELSSLRSEDTAVYFCAYYDAAGPWFAYWGQGTTVTVSS

SEQ ID NO. 73
QVQLVQSGAEVKKPGASVKVSCKASGYTFTNYWLGWVRQAPGQGLEWIGDIYPGGGYTNYN
EKFKGKATLTADTSSSTAYMQLSSLTSEDSAVYYCAYYDAAGPWFAYWGQGTTVTVSS

SEQ ID NO. 74
QVQLVQSGAEVKKPGASVKVSCKASGYTFTNYWLGWVRQAPGQGLEWIGDIYPGGGYTNYN
EKFKGKATLTADTSTSTAYMELSSLTSEDSAVYFCAYYDAAGPWFAYWGQGTTVTVSS

SEQ ID NO. 75
QVQLVQSGAEVKKPGASVKVSCKASGYTFTNYWLGWVKQRPGQGLEWIGDIYPGGGYTNYN
EKFKGRVTITADTSTSTAYMELSSLRSEDTAVYFCAYYDAAGPWFAYWGQGTLVTVSS

SEQ ID NO. 76
QVQLVQSGAEVKKPGASVKVSCKASGYTFTNYWLGWVRQAPGQGLEWIGDIYPGGGYTNYN
EKFKGRVTITADTSTSTAYMELSSLRSEDTAVYYCAYYDAAGPWFAYWGQGTLVTVSS

SEQ ID NO. 77
QVQLVQSGAEVKKPGASVKVSCKASGYTFTNYWLGWVRQAPGQGLEWIGDIYPGGGYTNYN
EKFKGRVTITADTSTSTAYMELSSLRSEDTAVYYCAYYDAAGPWFAYWGQGTLVTVSS

SEQ ID NO. 78
QVQLVQSGAEVKKPGASVKVSCKASGYTFTNYWLGWVRQAPGQGLEWMGDIYPGGGYTNYN
EKFKGRVTITADTSTSTAYMELSSLRSEDTAVYYCAYYDAAGPWFAYWGQGTLVTVSS

| SEQUENCE INFORMATION |
|---|

SEQ ID NO. 79
QVQLVQSGAEVKKPGASVKVSCKASGYTFTNYWLGWVRQAPGQGLEWMGDIYPGGGYTNYN
EKFKGRVTMTRDTSTSTVYMELSSLRSEDTAVYYCAYYDAAGPWFAYWGQGTLVTVSS

| Variable light chains |
|---|

SEQ ID NO. 80
DIQMTQTPLSLPVSLGDQASISCRSSQSIVHSNGNTYLEWYLQKPGQSPKLLIYKVSNRFS
GVPDRFSGSGSGTDFTLKISRVEAEDLGVYYCFQGSHVPYTFGGGTKLEIKRA

SEQ ID NO. 81
DIVITQTPLSLPVSLGDQASISCRSSQSLLHSNGNTYLHWYLQKPGQSPKLLIYKVSNRFS
GVPDRFSGSGSGTDFTLKISRVEAEDLGVYFCSQSTHVPYTFGGGTKLEIKRA

SEQ ID NO. 82
DIQMTQTPLSLPVSLGDQASISCRSSQSIVHSNGNTYLEWYLQKPGQSPKLLIYKVSNRFS
GVPDRFSGSGSGTDFTLKISRVEAEDLGVYYCFQGSHVPYTFGGGTKLELKRA

SEQ ID NO. 83
DVLMTQTPLSLPVSLGDQASISCRSSQSIVHSNGNTYLEWYLQKPGQSPKLLIYKVSNRFS
GVPDRFSGSGSGTDFTLKISRVEAEDLGVYYCFQGSHVPYTFGGGTKLEIKRA

SEQ ID NO. 84
DVLMTQTPLSLPVSLGDQASISCRSSQSIVHSNGNTYLEWYLQKPGQSPKLLIYKVSNRFS
GVPDRFSGSGSGTDFTLKISRVEAEDLGVYYCFQGSHVPYTFGGGTKLELKRA

SEQ ID NO. 85
DIQMTQSPLSLPVTPGEPASISCRSSQSIVHSNGNTYLEWYLQKPGQSPKLLIYKVSNRFS
GVPDRFSGSGSGTDFTLKISRVEAEDVGVYYCFQGSHVPYTFGGGTKVEIKRA

SEQ ID NO. 86
DIQMTQSPLSLPVTPGEPASISCRSSQSIVHSNGNTYLEWYLQKPGQSPKLLIYKVSNRFS
GVPDRFSGSGSGTDFTLKISRVEAEDVGVYYCFQGSHVPYTFGQGTKVEIKRA

SEQ ID NO. 87
DIQMTQSPLSLPVTPGEPASISCRSSQSIVHSNGNTYLEWYLQKPGQSPQLLIYKVSNRFS
GVPDRFSGSGSGTDFTLKISRVEAEDVGVYYCFQGSHVPYTFGGGTKVEIKRA

SEQ ID NO. 88
DIQMTQSPLSLPVTPGEPASISCRSSQSIVHSNGNTYLEWYLQKPGQSPQLLIYKVSNRFS
GVPDRFSGSGSGTDFTLKISRVEAEDVGVYYCFQGSHVPYTFGQGTKVEIKRA

SEQ ID NO. 89
DIVMTQSPLSLPVTPGEPASISCRSSQSIVHSNGNTYLEWYLQKPGQSPKLLIYKVSNRFS
GVPDRFSGSGSGTDFTLKISRVEAEDVGVYYCFQGSHVPYTFGGGTKVEIKRA

SEQ ID NO. 90
DIVMTQSPLSLPVTPGEPASISCRSSQSIVHSNGNTYLEWYLQKPGQSPKLLIYKVSNRFS
GVPDRFSGSGSGTDFTLKISRVEAEDVGVYYCFQGSHVPYTFGQGTKVEIKRA

SEQ ID NO. 91
DIVMTQSPLSLPVTPGEPASISCRSSQSIVHSNGNTYLEWYLQKPGQSPQLLIYKVSNRFS
GVPDRFSGSGSGTDFTLKISRVEAEDVGVYYCFQGSHVPYTFGGGTKVEIKRA

SEQ ID NO. 92
DIVMTQSPLSLPVTPGEPASISCRSSQSIVHSNGNTYLEWYLQKPGQSPQLLIYKVSNRFS
GVPDRFSGSGSGTDFTLKISRVEAEDVGVYYCFQGSHVPYTFGQGTKVEIKRA

SEQ ID NO. 93
DIVMTQTPLSLPVTPGQPASISCRSSQSIVHSNGNTYLEWYLQKPGQSPQLLIYKVSNRFS
GVPDRFSGSGSGTDFTLKISRVEAEDVGVYYCFQGSHVPYTFGQGTKVEIKRA

SEQ ID NO. 94
DIVMTQTPLSLSVTPGQPASISCRSSQSIVHSNGNTYLEWYLQKPGQSPQLLIYKVSNRFS
GVPDRFSGSGSGTDFTLKISRVEAEDVGVYYCFQGSHVPYTFGQGTKVEIKRA

| VH/VL pairs Mouse antibody | |
|---|---|
| Karo1 | SEQ ID NO. 46 |
|  | SEQ ID NO. 80 |
| Karo2 | SEQ ID NO. 47 |
|  | SEQ ID NO. 81 |
| Karo3 | SEQ ID NO. 48 |
|  | SEQ ID NO. 80 |
| Karo4 | SEQ ID NO. 50 |
|  | SEQ ID NO. 80 |
| Karo5 | SEQ ID NO. 53 |
|  | SEQ ID NO. 82 |
| Karo6 | SEQ ID NO. 52 |
|  | SEQ ID NO. 83 |
| Karo7 | SEQ ID NO. 55 |
|  | SEQ ID NO. 83 |
| Karo8 | SEQ ID NO. 54 |
|  | SEQ ID NO. 80 |
| Karo9 | SEQ ID NO. 51 |
|  | SEQ ID NO. 83 |

| SEQUENCE INFORMATION | |
|---|---|
| Karo10 | SEQ ID NO. 49 |
|  | SEQ ID NO. 80 |

| humanized sequences | |
|---|---|
| Karo11 | SEQ ID NO. 56 |
|  | SEQ ID NO. 90 |
| Karo12 | SEQ ID NO. 57 |
|  | SEQ ID NO. 90 |
| Karo13 | SEQ ID NO. 57 |
|  | SEQ ID NO. 86 |
| Karo14 | SEQ ID NO. 58 |
|  | SEQ ID NO. 87 |
| Karo15 | SEQ ID NO. 56 |
|  | SEQ ID NO. 91 |
| Karo16 | SEQ ID NO. 59 |
|  | SEQ ID NO. 91 |
| Karo17 | SEQ ID NO. 60 |
|  | SEQ ID NO. 87 |
| Karo18 | SEQ ID NO. 61 |
|  | SEQ ID NO. 90 |
| Karo19 | SEQ ID NO. 56 |
|  | SEQ ID NO. 88 |
| Karo20 | SEQ ID NO. 56 |
|  | SEQ ID NO. 85 |
| Karo21 | SEQ ID NO. 59 |
|  | SEQ ID NO. 90 |
| Karo22 | SEQ ID NO. 62 |
|  | SEQ ID NO. 90 |
| Karo23 | SEQ ID NO. 59 |
|  | SEQ ID NO. 86 |
| Karo24 | SEQ ID NO. 74 |
|  | SEQ ID NO. 92 |
| Karo25 | SEQ ID NO. 63 |
|  | SEQ ID NO. 87 |
| Karo26 | SEQ ID NO. 74 |
|  | SEQ ID NO. 87 |
| Karo27 | SEQ ID NO. 74 |
|  | SEQ ID NO. 89 |
| Karo28 | SEQ ID NO. 74 |
|  | SEQ ID NO. 85 |
| Karo29 | SEQ ID NO. 64 |
|  | SEQ ID NO. 86 |
| Karo30 | SEQ ID NO. 74 |
|  | SEQ ID NO. 86 |
| Karo31 | SEQ ID NO. 63 |
|  | SEQ ID NO. 86 |
| Karo32 | SEQ ID NO. 65 |
|  | SEQ ID NO. 85 |
| Karo33 | SEQ ID NO. 65 |
|  | SEQ ID NO. 86 |
| Karo34 | SEQ ID NO. 66 |
|  | SEQ ID NO. 85 |
| Karo35 | SEQ ID NO. 67 |
|  | SEQ ID NO. 87 |
| Karo36 | SEQ ID NO. 68 |
|  | SEQ ID NO. 86 |
| Karo37 | SEQ ID NO. 72 |
|  | SEQ ID NO. 88 |
| Karo38 | SEQ ID NO. 69 |
|  | SEQ ID NO. 90 |
| Karo39 | SEQ ID NO. 70 |
|  | SEQ ID NO. 90 |
| Karo40 | SEQ ID NO. 69 |
|  | SEQ ID NO. 92 |
| Karo41 | SEQ ID NO. 73 |
|  | SEQ ID NO. 86 |
| Karo42 | SEQ ID NO. 69 |
|  | SEQ ID NO. 89 |
| Karo43 | SEQ ID NO. 71 |
|  | SEQ ID NO. 92 |

| SEQUENCE INFORMATION | |
|---|---|
| Karo44 | SEQ ID NO. 56 |
| | SEQ ID NO. 86 |
| Karo45 | SEQ ID NO. 65 |
| | SEQ ID NO. 92 |
| Various single-chain Fv formats | |

```
                                                      SEQ ID NO. 95
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSASS
GGGGSGGGGSGGSARDIQMTQTPLSLPVSLGDQASISCRSSQSIVHSNGNTYLEWYLQKPG
QSPKLLIYKVSNRFSGVPDRFSGSGSGTDFTLKISRVEAEDLGVYYCFQGSHVPYTFGGGT
KLEIKRAAAHHHHHHGAAEQKLISEEDLNGAA
                                                      SEQ ID NO. 96
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSASS
GSGSSADIQMTQTPLSLPVSLGDQASISCRSSQSIVHSNGNTYLEWYLQKPGQSPKLLIYK
VSNRFSGVPDRFSGSGSGTDFTLKISRVEAEDLGVYYCFQGSHVPYTFGGGTKLEIKRAAA
HHHHHHGAAEQKLISEEDLNGAA
                                                      SEQ ID NO. 97
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSASS
GGSSADIQMTQTPLSLPVSLGDQASISCRSSQSIVHSNGNTYLEWYLQKPGQSPKLLIYKV
SNRFSGVPDRFSGSGSGTDFTLKISRVEAEDLGVYYCFQGSHVPYTFGGGTKLEIKRAAAH
HHHHHGAAEQKLISEEDLNGAA
                                                      SEQ ID NO. 98
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSASS
GSSADIQMTQTPLSLPVSLGDQASISCRSSQSIVHSNGNTYLEWYLQKPGQSPKLLIYKVS
NRFSGVPDRFSGSGSGTDFTLKISRVEAEDLGVYYCFQGSHVPYTFGGGTKLEIKRAAAHH
HHHHGAAEQKLISEEDLNGAA
                                                      SEQ ID NO. 99
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSASS
SSADIQMTQTPLSLPVSLGDQASISCRSSQSIVHSNGNTYLEWYLQKPGQSPKLLIYKVSN
RFSGVPDRFSGSGSGTDFTLKISRVEAEDLGVYYCFQGSHVPYTFGGGTKLEIKRAAAHHH
HHHGAAEQKLISEEDLNGAA
                                                      SEQ ID NO. 100
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSASS
SADIQMTQTPLSLPVSLGDQASISCRSSQSIVHSNGNTYLEWYLQKPGQSPKLLIYKVSNR
FSGVPDRFSGSGSGTDFTLKISRVEAEDLGVYYCFQGSHVPYTFGGGTKLEIKRAAAHHHH
HHGAAEQKLISEEDLNGAA
                                                      SEQ ID NO. 101
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSASS
ADIQMTQTPLSLPVSLGDQASISCRSSQSIVHSNGNTYLEWYLQKPGQSPKLLIYKVSNRF
SGVPDRFSGSGSGTDFTLKISRVEAEDLGVYYCFQGSHVPYTFGGGTKLEIKRAAAHHHHH
HGAAEQKLISEEDLNGAA
                                                      SEQ ID NO. 102
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSASA
DIQMTQTPLSLPVSLGDQASISCRSSQSIVHSNGNTYLEWYLQKPGQSPKLLIYKVSNRFS
GVPDRFSGSGSGTDFTLKISRVEAEDLGVYYCFQGSHVPYTFGGGTKLEIKRAAAHHHHHH
GAAEQKLISEEDLNGAA
                                                      SEQ ID NO. 103
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSAAD
IQMTQTPLSLPVSLGDQASISCRSSQSIVHSNGNTYLEWYLQKPGQSPKLLIYKVSNRFSG
VPDRFSGSGSGTDFTLKISRVEAEDLGVYYCFQGSHVPYTFGGGTKLEIKRAAAHHHHHHG
AAEQKLISEEDLNGAA
                                                      SEQ ID NO. 104
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSADI
QMTQTPLSLPVSLGDQASISCRSSQSIVHSNGNTYLEWYLQKPGQSPKLLIYKVSNRFSGV
PDRFSGSGSGTDFTLKISRVEAEDLGVYYCFQGSHVPYTFGGGTKLEIKRAAAHHHHHHGA
AEQKLISEEDLNGAA
                                                      SEQ ID NO. 105
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSSDIQ
MTQTPLSLPVSLGDQASISCRSSQSIVHSNGNTYLEWYLQKPGQSPKLLIYKVSNRFSGVP
DRFSGSGSGTDFTLKISRVEAEDLGVYYCFQGSHVPYTFGGGTKLEIKRAAAHHHHHHGAA
EQKLISEEDLNGAA
                                                      SEQ ID NO. 106
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPGFAYWGQGTTVTVSDIQM
TQTPLSLPVSLGDQASISCRSSQSIVHSNGNTYLEWYLQKPGQSPKLLIYKVSNRFSGVPD
```

SEQUENCE INFORMATION

```
RFSGSGSGTDFTLKISRVEAEDLGVYYCFQGSHVPYTFGGGTKLEIKRAAAHHHHHGAAE
QKLISEEDLNGAA
```

Murine Antibodies

SEQ ID NO. 107
```
DIVITQTPLSLPVSLGDQASISCRSSQSLLHSNGNTYLHWYLQKPGQSPKLLIYKVSNRFS
GVPDRFSGSGSGTDFTLKISRVEAEDLGVYFCSQSTHVPYTFGGGTKLEIKRADAAPTVSI
FPPSSEQLTSGGASVVCFLNNFYPKDINVKWKIDGSERQNGVLNSWTDQDSKDSTYSMSST
LTLTKDEYERHNSYTCEATHKTSTSPIVKSFNRNEC
```

SEQ ID NO. 108
```
DIQMTQTPLSLPVSLGDQASISCRSSQSIVHSNGNTYLEWYLQKPGQSPKLLIYKVSNRFS
GVPDRFSGSGSGTDFTLKISRVEAEDLGVYYCFQGSHVPYTFGGGTKLEIKRADAAPTVSI
FPPSSEQLTSGGASVVCFLNNFYPKDINVKWKIDGSERQNGVLNSWTDQDSKDSTYSMSST
LTLTKDEYERHNSYTCEATHKTSTSPIVKSFNRNEC
```

SEQ ID NO. 109
```
QVQLKQSGAELVRPGTSVKISCKISGYTFTNYWLGWVKQRPGHGLEWIGDIYPGGSYTNYN
EKFKGKATLTADTSSSTAYMQLSSLTSEDSAVYFCARYDNHYFDYWGQGTTLTVSESQSFP
NVFPLVSCESPLSDKNLVAMGCLARDFLPSTISFTWNYQNNTEVIQGIRTFPTLRTGGKYL
ATSQVLLSPKSILEGSDEYLVCKIHYGGKNRDLHVPIPAVAEMNPNVNVFVPPRDGFSGPA
PRKSKLICEATNFTPKPITVSWLKDGKLVESGFTTDPVTIENKGSTPQTYKVISTLTISEI
DWLNLNVYTCRVDHRGLTFLKNVSSTCAASPSTDILTFTIPPSFADIFLSKSANLTCLVSN
LATYETLNISWASQSGEPLETKIKIMESHPNGTFSAKGVASVCVEDWNNRKEFVCTVTHRD
LPSPQKKFISKPNEVHKHPPAVYLLPPAREQLNLRESATVTCLVKGFSPADISVQWLQRGQ
LLPQEKYVTSAPMPEPGAPGFYFTHSILTVTEEEWNSGETYTCVVGHEALPHLVTERTVDK
STGKPTLYNVSLIMSDTGGTCY
```

SEQ ID NO. 110
```
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTTVTVSESQS
FPNVFPLVSCESPLSDKNLVAMGCLARDFLPSTISFTWNYQNNTEVIQGIRTFPTLRTGGK
YLATSQVLLSPKSILEGSDEYLVCKIHYGGKNRDLHVPIPAVAEMNPNVNVFVPPRDGFSG
PAPRKSKLICEATNFTPKPITVSWLKDGKLVESGFTTDPVTIENKGSTPQTYKVISTLTIS
EIDWLNLNVYTCRVDHRGLTFLKNVSSTCAASPSTDILTFTIPPSFADIFLSKSANLTCLV
SNLATYETLNISWASQSGEPLETKIKIMESHPNGTFSAKGVASVCVEDWNNRKEFVCTVTH
RDLPSPQKKFISKPNEVHKHPPAVYLLPPAREQLNLRESATVTCLVKGFSPADISVQWLQR
GQLLPQEKYVTSAPMPEPGAPGFYFTHSILTVTEEEWNSGETYTCVVGHEALPHLVTERTV
DKSTGKPTLYNVSLIMSDTGGTCY
```

| | |
|---|---|
| mIgM-Karo2 | SEQ ID NO. 109 |
| | SEQ ID NO. 107 |
| mIgM-Karo4 | SEQ ID NO. 110 |
| | SEQ ID NO. 108 |

Chimeric antibodies (mouse/human)

SEQ ID NO. 111
```
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTTVTVSGSTK
GPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCS
VMHEALHNHYTQKSLSLSPGK
```

SEQ ID NO. 112
```
QVQLKESGAELVRPGTSVKISCKASGYTFTNYWLGWVKQRPGHGLEWIGDIYPGGGYTNYN
EKFKGKATLTADTSSSTAYMQLSSLTSEDSAVYFCAYYDAAGPWFAYWGQGTTVTVSGSAS
APTLFPLVSCENSPDTSSVAVGCLAQDFLPDSITLSWKYKNNSDISSTRGFPSVLRGGKY
AATSQVLLSPKDVMQGTDEHVVCKVQHPNGNKEKNVPLPVIAELPPKVSVFVPPRDGFFGN
PRKSKLICQATGFSPRQIQVSWLREGKQVGSGVTTDQVQAEAKESGPTTYKVTSTLTIKES
DWLGQSMFTCRVDHRGLTFQQNASSMCVPDQDTAIRVFAIPPSFASIFLTKSTKLTCLVTD
LTTYDSVTISWTRQNGEAVKTHTNISESHPNATFSAVGEASICEDDWNSGERFTCTVTHTD
LPSPLKQTISRPKGVALHRPDVYLLPPAREQLNLRESATITCLVTGFSPADVFVQWMQRGQ
PLSPEKYVTSAPMPEPQAPGRYFAHSILTVSEEEWNTGETYTCVVAHEALPNRVTERTVDK
STGKPTLYNVSLVMSDTAGTCY
```

-continued

| SEQUENCE INFORMATION |
|---|
| SEQ ID NO. 113 |
| DIQMTQTPLSLPVSLGDQASISCRSSQSIVHSNGNTYLEWYLQKPGQSPKLLIYKVSNRFS |
| GVPDRFSGSGSGTDFTLKISRVEAEDLGVYYCFQGSHVPYTFGGGTKLEIKRTVAAPSVFI |
| FPPSDEQLKSGTASVVCLLNNFYPREAKVQWKVDNALQSGNSQESVTEQDSKDSTYSLSST |
| LTLSKADYEKHKVYACEVTHQGLSSPVTKSFNRGEC |

| Chimeric antibodies | | |
|---|---|---|
| cIgG-Karo4 | SEQ ID NO. 111 | |
| | SEQ ID NO. 113 | |
| cIgM-Karo4 | SEQ ID NO. 112 | |
| | SEQ ID NO. 113 | |

We claim the following:

1. A method for the diagnosis, follow-up, or treatment of a cancer disease in a subject comprising: administering to the subject a recombinant recognition molecule which comprises a variable heavy chain and a variable light chain and which specifically binds to core 1 antigen, wherein the variable heavy chain comprises (i) a CDRH1 region that comprises the amino acid sequence of SEQ ID NO: 1, or a variant thereof having at least 70% homology with SEQ ID NO: 1; (ii) a CDRH2 region that comprises the amino acid sequence of SEQ ID NO: 2 or SEQ ID NO: 3, or a variant thereof having at least 70% homology to SEQ ID NO: 2 or SEQ ID NO: 3; and (iii) a CDRH3 region that comprises the amino acid sequence of SEQ ID NO: 4, SEQ ID NO: 5, or SEQ ID NO: 6, or a variant thereof having at least 70% homology to SEQ ID NO: 4, SEQ ID NO: 5, or SEQ ID NO: 6; and the variable light chain comprises (i) a CDRL1 region that comprises the amino acid sequence of SEQ ID NO: 7, SEQ ID NO: 8, or SEQ ID NO: 9, or a variant thereof having at least 70% homology to SEQ ID NO: 7, SEQ ID NO: 8, or SEQ ID NO: 9; (ii) a CDRL2 region that comprises the amino acid sequence of SEQ ID NO: 10 or SEQ ID NO: 11, or a variant thereof having at least 70% homology to SEQ ID NO: 10 or SEQ ID NO: 11; and a CDRL3 region that comprises the amino acid sequence of SEQ ID NO: 12 or SEQ ID NO: 13, or a variant thereof having at least 70% homology to SEQ ID NO: 12 or SEQ ID NO: 13.

2. The method of claim 1 wherein the cancer disease comprises tumors.

3. The method of claim 1 wherein the cancer disease comprises metastases.

4. The method of claim 1, wherein the cancer disease is mammary carcinoma, cervical carcinoma, ovarian carcinoma, colon carcinoma, gastrointestinal carcinoma, pancreas carcinoma, stomach carcinoma, lung carcinoma, prostate carcinoma, small intestine cancer, renal cell carcinoma, or liver metastases.

5. The method of claim 1, wherein the CDRH1 region comprises the amino acid sequence of SEQ ID NO: 1.

6. The method of claim 1, wherein the CDRH1 region variant has I, M, W, or V substituted for L at position 4 of SEQ ID NO: 1.

7. The method of claim 1, wherein the CDRH2 region comprises the amino acid sequence of SEQ ID NO: 2 or SEQ ID NO: 3.

8. The method of claim 1, wherein the CDRH2 region variant is selected from (a) a variant that has T or A substituted for P at position 4 of SEQ ID NO: 2 or 3; (b) a variant that has D or N substituted for G or S at position 7 of SEQ ID NO: 2 or 3; and (c) a variant that has T or A substituted for P at position 4 and D or N substituted for G or S at position 7 of SEQ ID NO: 2 or 3.

9. The method of claim 1, wherein the recombinant recognition molecule comprises a CDRH3 region that comprises the amino acid sequence of SEQ ID NO: 4, SEQ ID NO: 5, or SEQ ID NO: 6.

10. The method of claim 1, wherein the CDRL1 region comprises the amino acid sequence of SEQ ID NO: 7, SEQ ID NO: 8, or SEQ ID NO: 9.

11. The method of claim 1, wherein the CDRL1 region variant is selected from (a) a variant that has P substituted for S at position 2 of SEQ ID NO: 7, 8 or 9; (b) a variant that has F substituted for L at position 15 of SEQ ID NO: 7, 8 or 9; and (c) a variant that has P substituted for S at position 2 of SEQ ID NO: 7, 8 or 9 and F substituted for L at position 15 of SEQ ID NO: 7, 8 or 9.

12. The method of claim 1, wherein the CDRL2 region comprises the amino acid sequence of SEQ ID NO: 10 or SEQ ID NO: 11.

13. The method of claim 1, wherein the CDRL3 region comprises the amino acid sequence of SEQ ID NO: 12 or SEQ ID NO: 13.

14. The method of claim 1, wherein the recombinant recognition molecule comprises an FRH1 region comprising the following sequence, the amino acid position corresponding to the numbering according to Kabat, 1 Q or E
2 V
3 Q, K or T
4 L
5 K or V
6 E or Q
7 S
8 G
9 A
10 E
11 L or V
12 V or K
13 R or K
14 P
15 G
16 T or A
17 S
18 V
19 K
20 I or V
21 S or P
22 C
23 K
24 A, V, S or T
25 S
26 G
27 Y, F, S or D
28 T
29 F,L or I
30 T.

15. The method of claim 1, wherein the recombinant recognition molecule comprises an FRH2 region comprising the following sequence, the amino acid position corresponding to the numbering according to Kabat, 36 W
37 V
38 K or R
39 Q
40 R or A 41 P
42 G
43 H or Q
44 G
45 L
46 E
47 W or R
48 I or M
49 G.

16. The method of claim 1, wherein the recombinant recognition molecule comprises an FRH3 region comprising the following sequence, the amino acid position corresponding to the numbering according to Kabat,
66 K or R
67 A or V
68 T
69 L or M
70 T
71 A, L or T
72 D
73 T
74 S
75 S or T
76 S
77 T
78 A
79 Y
80 M
81 Q or E
82 L
82a S
82b S or R
82c L
83 T or R
84 S
85 E
86 D
87 S or T
88 A
89 V
90 Y
91 F or Y
92 C
93 A
94 Y, K or R.

17. The method of claim 1, wherein the recombinant recognition molecule comprises an FRH4 region comprising the following sequence, the amino acid position corresponding to the numbering according to Kabat,
103 W
104 G
105 Q
106 G
107 T
108 T, S or L
109 V or L
110 T
111 V
112 S
113 S or A.

18. The method of claim 1, wherein the recombinant recognition molecule comprises an FRL1 region comprising the following sequence, the amino acid position corresponding to the numbering according to Kabat,
1 D
2 I, V or L
3 Q or L
4 M
5 T
6 Q
7 T or S
8 P
9 L
10 S
11 L
12 P
13 V
14 S or T
15 L or P
16 G
17 D or E
18 Q or P
19 A
20 S
21 I
22 S
23 C.

19. The method of claim 1, wherein the recombinant recognition molecule comprises an FRL2 region comprising the following sequence, the amino acid position corresponding to the numbering according to Kabat,
35 W
36 Y
37 L
38 Q
39 K
40 P
41 G
42 Q
43 S
44 P
45 K or Q
46 L
47 L
48 I or V
49 Y.

20. The method of claim 1, wherein the recombinant recognition molecule comprises an FRL3 region comprising the following sequence, the amino acid position corresponding to the numbering according to Kabat,
57 G
58 V
59 P
60 D
61 R
62 F
63 S
64 G
65 S
66 G
67 S
68 G
69 T
70 D
70 F
72 T
73 L
74 K
75 I
76 S
77 R
78 V
79 E
80 A 81 E
82 D
83 L or V
84 G
85 V
86 Y
87 Y
88 C.

21. The method of claim 1, wherein the recombinant recognition molecule comprises an FRL4 region comprising the following sequence, the amino acid position corresponding to the numbering according to Kabat,
98 F
99 G
100 G or Q
101 G
102 T
103 K
104 L
105 E
106 I or L
106a K
107 R
108 A.

22. A molecule for tumor recognition comprising a variable heavy chain and a variable light chain and which specifically binds to core 1 antigen, wherein the variable heavy chain comprises (i) a CDRH1 region that comprises the amino acid sequence of SEQ ID NO: 1, or a variant thereof having at least 70% homology with SEQ ID NO: 1; (ii) a CDRH2 region that comprises the amino acid sequence of SEQ ID NO: 2 or SEQ ID NO: 3, or a variant thereof having at least 70% homology to SEQ ID NO: 2 or SEQ ID NO: 3; and (iii) a CDRH3 region that comprises the amino acid sequence of SEQ ID NO: 4, SEQ ID NO: 5, or SEQ ID NO: 6, or a variant thereof having at least 70% homology to SEQ ID NO: 4, SEQ ID NO: 5, or SEQ ID NO: 6; and the variable light chain comprises (i) a CDRL1 region that comprises the amino acid sequence of SEQ ID NO: 7, SEQ ID NO: 8, or SEQ ID NO: 9, or a variant thereof having at least 70% homology to SEQ ID NO: 7, SEQ ID NO: 8, or SEQ ID NO: 9; (ii) a CDRL2 region that comprises the amino acid sequence of SEQ ID NO: 10 or SEQ ID NO: 11, or a variant thereof having at least 70% homology to SEQ ID NO: 10 or SEQ ID NO: 11; and a CDRL3 region that comprises the amino acid sequence of SEQ ID NO: 12 or SEQ ID NO: 13 or a variant thereof having at least 70% homology to SEQ ID NO: 12 or SEQ ID NO: 13.

\* \* \* \* \*